(12) United States Patent
Hall et al.

(10) Patent No.: US 11,541,154 B2
(45) Date of Patent: *Jan. 3, 2023

(54) ELECTROSPUN MATERIAL COVERED MEDICAL APPLIANCES AND METHODS OF MANUFACTURE

(71) Applicant: Merit Medical Systems, Inc., South Jordan, UT (US)

(72) Inventors: John William Hall, North Salt Lake, UT (US); Bart Dolmatch, Dallas, TX (US); Zeke Eller, Dallas, TX (US); Robert S. Kellar, Flagstaff, AZ (US); Rachel Lynn Simmons, Bountiful, UT (US); Wayne L. Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/827,790

(22) Filed: Mar. 14, 2013

(65) Prior Publication Data

US 2014/0079758 A1    Mar. 20, 2014

Related U.S. Application Data

(60) Provisional application No. 61/703,037, filed on Sep. 19, 2012.

(51) Int. Cl.

| | | |
|---|---|---|
| *A61K 9/70* | (2006.01) | |
| *A61F 2/82* | (2013.01) | |
| *A61L 27/34* | (2006.01) | |
| *A61L 27/56* | (2006.01) | |
| *A61L 31/14* | (2006.01) | |
| *A61L 31/04* | (2006.01) | |
| *D01D 5/00* | (2006.01) | |
| *D01F 6/12* | (2006.01) | |
| *A61L 27/16* | (2006.01) | |
| *A61L 31/10* | (2006.01) | |
| *D04H 1/728* | (2012.01) | |
| *D04H 3/073* | (2012.01) | |
| *B05D 1/00* | (2006.01) | |
| *A61L 2/16* | (2006.01) | |
| *A61F 2/30* | (2006.01) | |
| *A61F 2/07* | (2013.01) | |

(52) U.S. Cl.
CPC ............. *A61L 31/148* (2013.01); *A61F 2/82* (2013.01); *A61K 9/70* (2013.01); *A61L 27/16* (2013.01); *A61L 27/34* (2013.01); *A61L 27/56* (2013.01); *A61L 31/048* (2013.01); *A61L 31/10* (2013.01); *A61L 31/146* (2013.01); *B05D 1/007* (2013.01); *D01D 5/0076* (2013.01); *D01F 6/12* (2013.01); *D04H 1/728* (2013.01); *D04H 3/073* (2013.01); *A61F 2/07* (2013.01); *A61F 2002/30003* (2013.01); *A61F 2002/3006* (2013.01); *A61F 2002/30062* (2013.01); *A61F 2002/30067* (2013.01); *A61F 2002/30072* (2013.01)

(58) Field of Classification Search
CPC ........................................................ A61K 9/70
See application file for complete search history.

(56) References Cited

U.S. PATENT DOCUMENTS

| | | |
|---|---|---|
| 2,772,444 A | 12/1956 | Barrows et al. |
| 3,047,444 A | 7/1962 | Harwood |
| 3,203,365 A | 8/1965 | Bowe et al. |
| 4,043,331 A | 8/1977 | Martin et al. |
| 4,044,404 A | 8/1977 | Martin et al. |
| 4,096,227 A | 6/1978 | Gore |
| 4,127,706 A | 11/1978 | Martin et al. |
| 4,223,101 A | 9/1980 | Fine et al. |
| 4,323,525 A | 4/1982 | Bornat |
| 4,345,414 A | 8/1982 | Bornat et al. |
| 4,552,707 A | 11/1985 | How |
| 4,689,186 A | 8/1987 | Bornat |
| 5,167,890 A | 12/1992 | Sasshofer et al. |
| 5,236,447 A | 8/1993 | Kubo |
| 5,328,946 A | 7/1994 | Tuminello et al. |
| 5,344,297 A | 9/1994 | Hills |
| 5,509,902 A | 4/1996 | Raulerson |
| 5,512,051 A | 4/1996 | Wang et al. |
| 5,552,100 A | 9/1996 | Shannon et al. |
| 5,562,986 A | 10/1996 | Yamamoto et al. |
| 5,665,428 A | 9/1997 | Cha et al. |
| 5,700,572 A | 12/1997 | Klatt et al. |
| 5,702,658 A | 12/1997 | Pellegrin et al. |
| 5,741,333 A | 4/1998 | Frid |
| 5,810,870 A | 9/1998 | Myers et al. |
| 5,941,910 A | 8/1999 | Schindler et al. |
| 6,010,529 A | 1/2000 | Herweck et al. |
| 6,075,180 A | 6/2000 | Sharber et al. |
| 6,106,913 A | 8/2000 | Scardino |
| 6,165,212 A | 12/2000 | Dereume et al. |

(Continued)

FOREIGN PATENT DOCUMENTS

| | | |
|---|---|---|
| CN | 101584612 | 11/2009 |
| EP | 0457456 | 11/1991 |
| EP | 1605014 | 12/2005 |
| EP | 2363516 | 9/2011 |
| GB | 1577221 | 10/1980 |

(Continued)

OTHER PUBLICATIONS

Arras et al. Electrospinning of aligned fibers with adjustable orientation using auxiliary electrodes Jun. 2012.*

(Continued)

*Primary Examiner* — Sarah Alawadi
(74) *Attorney, Agent, or Firm* — Dorsey & Whitney LLP

(57) ABSTRACT

A medical appliance or prosthesis may comprise one or more layers of electrospun nanofibers, including electrospun polymers. The electrospun material may comprise layers including layers of polytetrafluoroethylene (PTFE). Electrospun nanofiber mats of certain porosities may permit tissue ingrowth into or attachment to the prosthesis.

18 Claims, 16 Drawing Sheets

(56) References Cited

U.S. PATENT DOCUMENTS

| | | |
|---|---|---|
| 6,238,430 B1 | 5/2001 | Klumb |
| 6,306,424 B1 | 10/2001 | Vyakarnam |
| 6,436,135 B1 | 8/2002 | Goldfarb |
| 6,498,207 B1 | 12/2002 | Hoshikawa et al. |
| 6,517,571 B1 | 2/2003 | Brauker et al. |
| 6,679,913 B2 | 1/2004 | Homsy |
| 7,115,220 B2 | 10/2006 | Dubson et al. |
| 7,118,698 B2 | 10/2006 | Armantrout et al. |
| 7,244,272 B2 | 7/2007 | Dubson et al. |
| 7,316,754 B2 | 1/2008 | Ide et al. |
| 7,413,575 B2 | 8/2008 | Phaneuf et al. |
| 7,416,559 B2 | 8/2008 | Shalaby |
| 7,485,141 B2 | 2/2009 | Majercak et al. |
| 7,498,079 B1 | 3/2009 | Donckers |
| 7,524,527 B2 | 4/2009 | Stenzel |
| 7,556,634 B2 | 7/2009 | Lee et al. |
| 7,582,240 B2 | 9/2009 | Marin et al. |
| 7,655,175 B2 | 2/2010 | Michael et al. |
| 7,799,261 B2 | 9/2010 | Orr et al. |
| 7,857,608 B2 | 12/2010 | Fabbricante et al. |
| 7,914,568 B2 * | 3/2011 | Cully ................ A61F 2/07 623/1.13 |
| 7,947,069 B2 | 5/2011 | Sanders |
| 7,981,353 B2 | 7/2011 | Mitchell et al. |
| 8,052,744 B2 | 11/2011 | Girton |
| 8,178,030 B2 | 5/2012 | Anneaux et al. |
| 8,257,640 B2 | 9/2012 | Anneaux et al. |
| 8,262,979 B2 | 9/2012 | Anneaux et al. |
| 8,637,109 B2 | 1/2014 | Grewe et al. |
| 8,691,543 B2 | 4/2014 | Gaudette et al. |
| 8,771,582 B2 | 7/2014 | Phaneuf et al. |
| 9,034,031 B2 | 5/2015 | Anneaux |
| 9,198,999 B2 | 12/2015 | Hall |
| 9,655,710 B2 | 5/2017 | Eller |
| 9,775,933 B2 | 10/2017 | Knisley et al. |
| 9,856,588 B2 | 1/2018 | Anneaux |
| 10,010,395 B2 | 7/2018 | Puckett |
| 10,028,852 B2 | 7/2018 | Hall |
| 10,154,918 B2 | 12/2018 | Haselby et al. |
| 10,405,963 B2 | 9/2019 | McAlpine |
| 10,675,850 B2 | 6/2020 | Hall et al. |
| 2001/0034549 A1 | 10/2001 | Bartholf et al. |
| 2001/0039446 A1 | 11/2001 | Edwin et al. |
| 2001/0049551 A1 | 12/2001 | Tseng et al. |
| 2001/0053929 A1 | 12/2001 | Vonesh et al. |
| 2002/0077693 A1 | 6/2002 | Barclay |
| 2002/0082675 A1 * | 6/2002 | Myers ................ A61F 2/07 623/1.13 |
| 2002/0084178 A1 | 7/2002 | Dubson |
| 2002/0090725 A1 | 7/2002 | Simpson et al. |
| 2002/0198588 A1 | 12/2002 | Armstrong |
| 2003/0040772 A1 | 2/2003 | Hyodoh et al. |
| 2003/0050711 A1 | 3/2003 | Laurencin |
| 2003/0074049 A1 | 4/2003 | Hoganson |
| 2003/0100944 A1 | 5/2003 | Laksin et al. |
| 2003/0114917 A1 * | 6/2003 | Holloway et al. ............ 623/1.13 |
| 2003/0139797 A1 | 7/2003 | Johnson |
| 2003/0195611 A1 | 10/2003 | Greenhalgh et al. |
| 2003/0211135 A1 | 11/2003 | Greenhalgh et al. |
| 2004/0016260 A1 | 1/2004 | Kobayashi et al. |
| 2004/0030377 A1 | 2/2004 | Dubson et al. |
| 2004/0033364 A1 | 2/2004 | Spiridigliozzi et al. |
| 2004/0038038 A1 | 2/2004 | Yeung |
| 2004/0051201 A1 | 3/2004 | Greenhalgh et al. |
| 2004/0054397 A1 | 3/2004 | Smith et al. |
| 2004/0167606 A1 | 8/2004 | Chouinard |
| 2004/0219345 A1 | 11/2004 | Armantrout et al. |
| 2005/0053782 A1 | 3/2005 | Sen et al. |
| 2005/0137675 A1 | 6/2005 | Dubson et al. |
| 2005/0187605 A1 | 8/2005 | Greenhalgh et al. |
| 2005/0244453 A1 | 11/2005 | Stucke et al. |
| 2005/0244639 A1 | 11/2005 | Marin et al. |
| 2005/0278018 A1 | 12/2005 | Jensen |
| 2006/0200232 A1 | 9/2006 | Phaneuf et al. |
| 2006/0228435 A1 * | 10/2006 | Andrady ................ B82Y 30/00 425/174.8 R |
| 2006/0233990 A1 * | 10/2006 | Humphrey ............... A61L 27/16 428/36.9 |
| 2007/0023131 A1 | 2/2007 | Farnsworth et al. |
| 2007/0026036 A1 | 2/2007 | Falotico et al. |
| 2007/0031607 A1 | 2/2007 | Dubson et al. |
| 2007/0043428 A1 | 2/2007 | Jennings et al. |
| 2007/0087027 A1 | 4/2007 | Greenhalgh et al. |
| 2007/0123973 A1 | 5/2007 | Roth |
| 2007/0142771 A1 | 6/2007 | Durcan |
| 2007/0207179 A1 * | 9/2007 | Andersen et al. ............ 424/423 |
| 2007/0207186 A1 | 9/2007 | Scanlon et al. |
| 2007/0244569 A1 | 10/2007 | Weber et al. |
| 2007/0269481 A1 | 11/2007 | Li et al. |
| 2007/0276477 A1 | 11/2007 | Lee et al. |
| 2008/0021545 A1 | 1/2008 | Reneker et al. |
| 2008/0029617 A1 | 2/2008 | Marshall et al. |
| 2008/0118541 A1 | 5/2008 | Pacetti |
| 2008/0119943 A1 | 5/2008 | Armstrong et al. |
| 2008/0199506 A1 | 8/2008 | Horres et al. |
| 2008/0208323 A1 | 8/2008 | El-Kurdi et al. |
| 2008/0208325 A1 | 8/2008 | Helmus et al. |
| 2008/0234812 A1 | 9/2008 | Pacetti |
| 2008/0242171 A1 | 10/2008 | Huang et al. |
| 2008/0281406 A1 | 11/2008 | Addonizio et al. |
| 2008/0286321 A1 | 11/2008 | Reneker et al. |
| 2008/0288044 A1 | 11/2008 | Osborne |
| 2008/0305143 A1 | 12/2008 | Chen et al. |
| 2008/0319535 A1 | 12/2008 | Craven et al. |
| 2009/0012607 A1 | 1/2009 | Kim et al. |
| 2009/0018643 A1 | 1/2009 | Hashi et al. |
| 2009/0030499 A1 | 1/2009 | Bebb et al. |
| 2009/0082846 A1 | 3/2009 | Chobotov |
| 2009/0127748 A1 | 5/2009 | Takahashi |
| 2009/0136651 A1 | 5/2009 | Larsen et al. |
| 2009/0160099 A1 | 6/2009 | Huang |
| 2009/0163994 A1 | 6/2009 | Quigley et al. |
| 2009/0227944 A1 | 9/2009 | Weber |
| 2009/0232920 A1 | 9/2009 | Lozano et al. |
| 2009/0248131 A1 | 10/2009 | Greenan |
| 2009/0248144 A1 | 10/2009 | Bahler et al. |
| 2009/0269429 A1 | 10/2009 | Lozano et al. |
| 2009/0280325 A1 | 11/2009 | Lozano et al. |
| 2009/0319034 A1 | 12/2009 | Sowinski |
| 2010/0013126 A1 | 1/2010 | Ishaque et al. |
| 2010/0042198 A1 | 2/2010 | Burton |
| 2010/0042199 A1 | 2/2010 | Burton |
| 2010/0063574 A1 | 3/2010 | Bogert |
| 2010/0076401 A1 | 3/2010 | Von Oepen et al. |
| 2010/0076543 A1 | 3/2010 | Melsheimer et al. |
| 2010/0093093 A1 | 4/2010 | Leong et al. |
| 2010/0129675 A1 | 5/2010 | Young |
| 2010/0190254 A1 | 7/2010 | Chian et al. |
| 2010/0233115 A1 * | 9/2010 | Patel ................ A61L 15/26 424/78.08 |
| 2010/0280590 A1 | 11/2010 | Sun et al. |
| 2010/0304205 A1 | 12/2010 | Jo et al. |
| 2010/0323052 A1 | 12/2010 | Orr et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0060276 A1 | 3/2011 | Schaeffer et al. |
| 2011/0087318 A1 | 4/2011 | Daugherty et al. |
| 2011/0089603 A1 | 4/2011 | Fabbricane et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2011/0263456 A1 | 10/2011 | Hartig |
| 2011/0295200 A1 | 12/2011 | Speck et al. |
| 2011/0301696 A1 | 12/2011 | Mangiardi |
| 2012/0114722 A1 * | 5/2012 | Ballard ................ D01D 5/0007 424/409 |
| 2012/0201988 A1 | 8/2012 | Hansen et al. |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |

(56) References Cited

U.S. PATENT DOCUMENTS

| | | | |
|---|---|---|---|
| 2013/0053948 A1* | 2/2013 | Anneaux | A61L 31/06 623/1.42 |
| 2013/0059497 A1 | 3/2013 | Anneaux et al. | |
| 2013/0079700 A1 | 3/2013 | Ballard et al. | |
| 2013/0231733 A1 | 9/2013 | Knisley et al. | |
| 2013/0238086 A1 | 9/2013 | Ballard et al. | |
| 2013/0268062 A1 | 10/2013 | Puckett et al. | |
| 2013/0316103 A1 | 11/2013 | Anneaux et al. | |
| 2014/0012304 A1 | 1/2014 | Lampropoulos et al. | |
| 2014/0079758 A1 | 3/2014 | Hall et al. | |
| 2014/0081386 A1* | 3/2014 | Haselby | A61F 2/07 623/1.46 |
| 2015/0081000 A1 | 3/2015 | Hossainy | |
| 2015/0134051 A1 | 5/2015 | Donadio et al. | |
| 2015/0320542 A1 | 11/2015 | Gabriele et al. | |
| 2016/0250048 A1 | 9/2016 | Hall et al. | |
| 2016/0331528 A1 | 11/2016 | Parker | |
| 2017/0360993 A1 | 10/2017 | Argentine et al. | |
| 2018/0064565 A1 | 3/2018 | MacTaggart | |
| 2019/0008665 A1 | 1/2019 | Hall et al. | |
| 2019/0060528 A1 | 2/2019 | Skender et al. | |
| 2019/0076276 A1 | 3/2019 | Longo | |
| 2019/0110911 A1 | 4/2019 | Nae | |
| 2020/0015987 A1 | 1/2020 | Einav | |
| 2021/0290416 A1 | 9/2021 | Hall et al. | |
| 2022/0047783 A1 | 2/2022 | Hall et al. | |
| 2022/0048285 A1 | 2/2022 | Hall et al. | |

FOREIGN PATENT DOCUMENTS

| | | |
|---|---|---|
| JP | 5140476 | 5/1975 |
| JP | 2007519491 | 7/2007 |
| JP | 2007531833 | 11/2007 |
| JP | 2009232882 | 10/2009 |
| JP | 2010517625 | 5/2010 |
| JP | 2010540190 | 12/2010 |
| KR | 20100077913 | 7/2010 |
| KR | 20100108382 | 10/2010 |
| KR | 1020100108382 | 10/2010 |
| WO | 199800090 | 1/1998 |
| WO | 2003051233 | 6/2003 |
| WO | 2004090206 | 10/2004 |
| WO | WO2005/018600 | 3/2005 |
| WO | 2005074547 | 8/2005 |
| WO | 2005098100 | 10/2005 |
| WO | 2006123340 | 11/2006 |
| WO | WO2007075256 | 7/2007 |
| WO | 2008097592 | 8/2008 |
| WO | 2009046372 | 4/2009 |
| WO | WO2009/127170 | 10/2009 |
| WO | WO2009146280 | 12/2009 |
| WO | 2010083530 | 7/2010 |
| WO | WO2010132636 | 11/2010 |
| WO | 2011017698 | 2/2011 |
| WO | 2012103501 | 8/2012 |
| WO | WO2012103501 | 8/2012 |
| WO | 2012122485 A3 | 3/2013 |
| WO | 2013109528 | 7/2013 |

OTHER PUBLICATIONS

U.S. Appl. No. 13/742,077, filed Jan. 15, 2013, Hall et al.
U.S. Appl. No. 13/742,025, filed Jan. 15, 2013, Hall et al.
International Search Report and Written Opinion dated Apr. 26, 2013 for PCT/US2013/021554.
U.S. Appl. No. 14/204,446, filed Mar. 11, 2014, Hall et al.
U.S. Appl. No. 14/207,344, filed Mar. 12, 2014, Mower et al.
Office Action dated Mar. 3, 2014 for U.S. Appl. No. 13/742,025.
Office Action dated May 9, 2014 for U.S. Appl. No. 13/360,444.
Office Action dated Jul. 2, 2014 for U.S. Appl. No. 14/044,050.
International Search Report and Written Opinion dated Jun. 26, 2014 for PCT/US2014/024868.
International Search Report and Written Opinion dated Jul. 1, 2014 for PCT/US2014/023416.
Restriction Requirement dated Jun. 21, 2013 for U.S. Appl. No. 13/360,444.
Restriction Requirement dated Sep. 26, 2013 for U.S. Appl. No. 13/742,025.
International Search Report and Written Opinion dated Sep. 6, 2013 for PCT/US2013/046245.
U.S. Appl. No. 13/360,444, filed Jan. 27, 2012, Eller et al.
U.S. Appl. No. 13/787,327, filed Mar. 6, 2013, Hall et al.
International Search Report and Written Opinion dated May 23, 2012 for PCT/US2012/023006.
U.S. Appl. No. 13/826,618, filed Mar. 14, 2013, Hall et al.
U.S. Appl. No. 13/829,452, filed Mar. 14, 2013, Hall et al.
International Report on Patentability dated Jul. 22, 2014 for PCT/US2013/021554.
Office Action dated Aug. 29, 2014 for U.S. Appl. No. 14/152,590.
Office Action dated Oct. 10, 2014 for U.S. Appl. No. 13/742,025.
Extended European Search Report dated Jun. 25, 2015 for EP12739348.6.
International Preliminary Report dated Apr. 2, 2015 for PCT/US2013/060812.
International Preliminary Report dated Jul. 30, 2013 for PCT/US2012/023006.
Office Action dated Jan. 13, 2015 for U.S. Appl. No. 13/827,790.
Office Action dated Jul. 29, 2015 for U.S. Appl. No. 14/152,626.
Office Action dated Aug. 10, 2015 for U.S. Appl. No. 14/044,050.
European Search Report dated Feb. 12, 2016 for EP13813055.4.
Office Action dated Jan. 12, 2016 for U.S. Appl. No. 14/152,590.
Office Action dated Jan. 22, 2016 for U.S. Appl. No. 14/152,626.
Office Action dated Feb. 22, 2016 for U.S. Appl. No. 13/742,077.
Office Action dated Nov. 2, 2015 for U.S. Appl. No. 13/742,077.
Office Action dated Nov. 20, 2015 for U.S. Appl. No. 13/826,618.
Office Action dated Dec. 18, 2015 for U.S. Appl. No. 14/081,504.
Notice of Allowance dated Jul. 11, 2016 for U.S. Appl. No. 13/826,618.
Office Action dated Jun. 8, 2016 for U.S. Appl. No. 14/044,050.
Office Action dated Jun. 9, 2016 for U.S. Appl. No. 14/152,626.
Office Action dated Jun. 30, 2016 for U.S. Appl. No. 14/081,715.
Extended European Search Report dated Mar. 30, 2016 for EP13838578.6.
International Search Report and Written Opinion dated Dec. 5, 2013 for PCT/US2013/060812.
Office Action dated Jan. 23, 2017 for U.S. Appl. No. 14/081,715.
Office Action dated Oct. 6, 2016 for U.S. Appl. No. 13/360,444.
Office Action dated Oct. 6, 2016 for U.S. Appl. No. 13/742,025.
Office Action dated Oct. 26, 2016 for U.S. Appl. No. 13/742,077.
Office Action dated Nov. 17, 2016 for U.S. Appl. No. 13/829,493.
Office Action dated Nov. 18, 2016 for U.S. Appl. No. 13/826,618.
Office Action dated Sep. 9, 2016 for U.S. Appl. No. 14/081,504.
Office Action dated Sep. 9, 2016 for U.S. Appl. No. 14/207,344.
Office Action dated Sep. 23, 2016 for U.S. Appl. No. 14/152,590.
Notice of Allowance dated Jan. 25, 2017 for U.S. Appl. No. 14/152,626.
Office Action dated Mar. 15, 2017 for U.S. Appl. No. 14/207,344.
Office Action dated May 19, 2017 for U.S. Appl. No. 13/742,025.
Office Action dated Jun. 19, 2017 for U.S. Appl. No. 14/081,504.
Office Action dated Jun. 29, 2017 for U.S. Appl. No. 14/081,715.
Office Action dated Mar. 31, 2017 for U.S. Appl. No. 14/204,466.
Office Action dated Apr. 7, 2017 for U.S. Appl. No. 13/826,618.
Office Action dated Apr. 27, 2017 for U.S. Appl. No. 13/742,077.
Office Action dated Jun. 23, 2017 for U.S. Appl. No. 13/829,493.
Office Action dated Jul. 12, 2017 for U.S. Appl. No. 15/053,232.
Office Action dated Sep. 11, 2017 for U.S. Appl. No. 14/832,422.
Notice of Allowance dated Oct. 4, 2017 for U.S. Appl. No. 14/204,466.
Office Action dated Sep. 28, 2017 for U.S. Appl. No. 14/207,344.
Office Action dated Oct. 20, 2017 for U.S. Appl. No. 13/826,618.
Office Action dated Nov. 17, 2017 for U.S. Appl. No. 13/360,444.
Office Action dated Nov. 21, 2017 for U.S. Appl. No. 14/152,590.
Office Action dated Dec. 29, 2017 for U.S. Appl. No. 14/081,504.
European Search Report dated Mar. 30, 2016 for EP13838784.0.
Notice of Allowance dated Apr. 3, 2018 for U.S. Appl. No. 14/081,504.

(56) References Cited

OTHER PUBLICATIONS

Notice of Allowance dated May 9, 2018 for U.S. Appl. No. 15/053,232.
Office Action dated Jan. 16, 2018 for U.S. Appl. No. 14/081,715.
Office Action dated Feb. 16, 2018 for U.S. Appl. No. 13/742,077.
Office Action dated May 11, 2018 for U.S. Appl. No. 14/832,422.
European Search Report dated Aug. 19, 2014 for EP12755426.9.
Office Action dated Jun. 15, 2018 for U.S. Appl. No. 14/207,344.
Office Action dated Jun. 28, 2018 for U.S. Appl. No. 14/081,715.
Office Action dated Jul. 26, 2018 for U.S. Appl. No. 14/152,590.
Office Action dated Aug. 6, 2018 for U.S. Appl. No. 13/360,444.
European Search Report dated Dec. 6, 2018 for EP13813055.4.
Office Action dated Jan. 17, 2019 for U.S. Appl. No. 14/832,422.
Office Action dated Jan. 25, 2019 for U.S. Appl. No. 14/207,344.
Office Action dated Feb. 8, 2019 for U.S. Appl. No. 14/081,715.
EP Examination Report dated May 28, 2019 for EP12755426.9.
Office Action dated Jul. 11, 2019 for U.S. Appl. No. 14/081,715.
Office Action dated Aug. 7, 2019 for U.S. Appl. No. 15/806,020.
Office Action dated Aug. 22, 2019 for U.S. Appl. No. 14/207,344.
Board Decision on Appeal dated Nov. 23, 2018 for U.S. Appl. No. 14/044,050.
Office Action dated Jan. 2, 2009 for U.S. Appl. No. 13/360,444.
Office Action dated Jan. 2, 2019 for U.S. Appl. No. 14/152,590.
Office Action dated Jan. 10, 2019 for U.S. Appl. No. 13/826,618.
Notice of Allowance dated Jan. 30, 2020 for U.S. Appl. No. 14/152,590.
Notice of Allowance dated Feb. 6, 2020 for U.S. Appl. No. 13/360,444.
Notice of Allowance dated Oct. 9, 2019 for U.S. Appl. No. 13/826,618.
Office Action dated Oct. 7, 2019 for U.S. Appl. No. 13/360,444.
Office Action dated Oct. 7, 2019 for U.S. Appl. No. 14/152,590.
Office Action dated Apr. 29, 2020 for U.S. Appl. No. 14/207,344.
Office Action dated May 1, 2020 for U.S. Appl. No. 16/035,334.
European Search Report dated Jun. 16, 2014 for EP14160501.4.
International Search Report and Written Opinion dated Sep. 17, 2013 for PCT/US2013/060172.
Notice of Allowance dated Aug. 7, 2020 for U.S. Appl. No. 14/207,344.
Office Action dated Jul. 30, 2020 for U.S. Appl. No. 15/806,020.
Notice of Allowance dated Mar. 13, 2020 for U.S. Appl. No. 14/832,422.
Office Action dated Feb. 20, 2020 for U.S. Appl. No. 15/806,020.
Office Action dated Mar. 25, 2020 for U.S. Appl. No. 14/081,715.
European Search Report dated Feb. 3, 2021 for EP20191283.9.
Notice of Allowance dated Feb. 24, 2021 for U.S. Appl. No. 16/035,334.
Yasuda, et al., Contact Angle of Water on Polymer Surfaces, Am Chem, Langmuir, vol. 10 No. 7, 1994.
Office Action dated Dec. 24, 2021 for U.S. Appl. No. 16/877,259.

* cited by examiner

ELECTROSPUN MATERIAL COVERED MEDICAL APPLIANCES AND METHODS OF MANUFACTURE

RELATED APPLICATIONS

This application claims priority to U.S. Provisional Application No. 61/703,037 filed on Sep. 19, 2012 titled "Electrospun Material Covered Medical Appliances and Methods of Manufacture," which is hereby incorporated by reference in its entirety.

TECHNICAL FIELD

The present disclosure relates generally to medical devices. More specifically, the present disclosure relates to medical appliances or other prostheses, particularly those made of, constructed from, or covered or coated with electrospun materials including polymers such as polytetrafluoroethylene (PTFE).

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
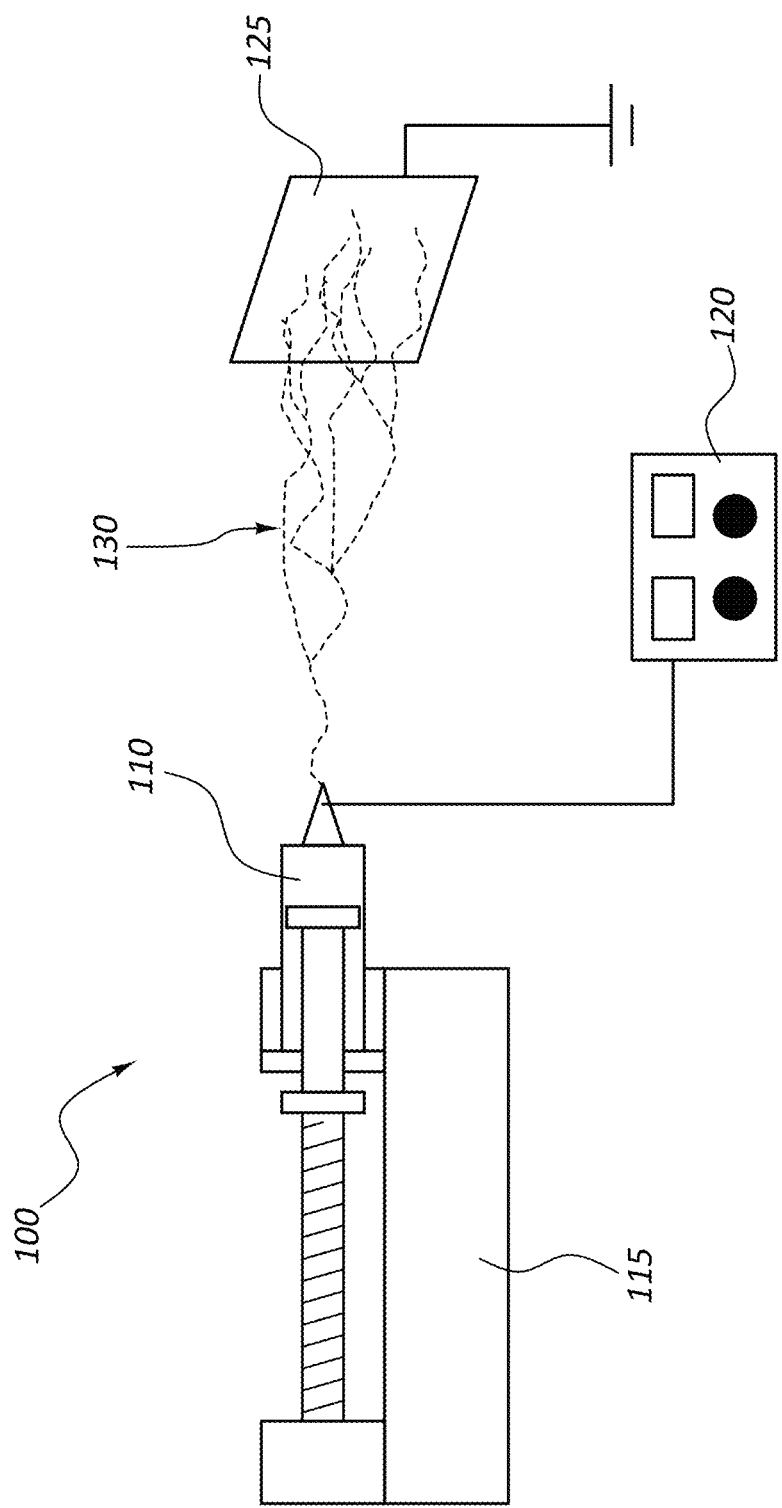
FIG. 1 is a schematic illustration of one embodiment of an electrospinning apparatus.

Medical appliances may be deployed in various body lumens for a variety of purposes. Stents may be deployed, for example, in the central venous system for a variety of therapeutic purposes including the treatment of occlusions within the lumens of that system. The current disclosure may be applicable to stents or other medical appliances designed for the central venous (CV) system, peripheral vascular (PV) stents, abdominal aortic aneurism (AAA) stents, bronchial stents, esophageal stents, biliary stents, coronary stents, gastrointestinal stents, neuro stents, thoracic aortic endographs, or any other stent or stent graft. Further, the present disclosure may be equally applicable to other prostheses such as grafts. Any medical appliance comprised of materials herein described may be configured for use or implantation within various areas of the body, including vascular, cranial, thoracic, pulmonary, esophageal, abdominal, or ocular application. Examples of medical appliances within the scope of this disclosure include, but are not limited to, stents, vascular grafts, stent grafts, cardiovascular patches, reconstructive tissue patches, hernia patches, general surgical patches, heart valves, sutures, dental reconstructive tissues, medical device coverings and coatings, gastrointestinal devices, blood filters, artificial organs, ocular implants, and pulmonary devices, including pulmonary stents. For convenience, many of the specific examples included below reference stents. Notwithstanding any of the particular medical appliances referenced in the examples or disclosure below, the disclosure and examples may apply analogously to any prosthesis or other medical appliance.

As used herein, the term "stent" refers to a medical appliance configured for use within a bodily structure, such as within a body lumen. A stent may comprise a scaffolding or support structure, such as a frame, and/or a covering. Thus, as used herein, "stent" refers to both covered and uncovered scaffolding structures.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a stent or another medical appliance. The proximal end of an appliance is defined as the end closest to the practitioner when the appliance is disposed within a deployment device that is being used by the practitioner. The distal end is the end opposite the proximal end, along the longitudinal direction of the appliance, or the end furthest from the practitioner. It is understood that, as used in the art, these terms may have different meanings once the appliance is deployed (i.e., the "proximal" end may refer to the end closest to the head or heart of the patient depending on application). For consistency, as used herein, the ends labeled "proximal" and "distal" prior to deployment remain the same regardless of whether the appliance is deployed. The longitudinal direction of a stent is the direction along the axis of a generally tubular stent. In embodiments where a stent or another appliance is composed of a metal wire structure coupled to one or more layers of a film or sheet-like components, such as a polymer layer, the metal structure is referred to as the "scaffolding" or "frame" and the polymer layer as the "covering" or "coating." The terms "covering" or "coating" may refer to a single layer of polymer, multiple layers of the same polymer, or layers comprising distinct polymers used in combination. Furthermore, as used herein, the terms "covering" and "coating" refer only to a layer or layers that are coupled to a portion of the scaffold; neither term requires that the entire scaffold be "covered" or "coated." In other words, medical appliances wherein a portion of the scaffold may be covered and a portion remain bare are within the scope of this disclosure. Finally, any disclosure recited in connection with coverings or coatings may analogously be applied to medical devices comprising one or more "covering" layers with no associated frame or other structure. For example, a hernia patch comprising any of the materials described herein as "coatings" or "coverings" is within the scope of this disclosure regardless of whether the patch further comprises a frame or other structure.

Medical device coverings may comprise multilayered constructs, comprised of two or more layers which may be serially applied. Further, multilayered constructs may comprise nonhomogeneous layers, meaning adjacent layers have differing properties. Thus, as used herein, each layer of a multilayered construct may comprise a distinct layer, either due to the distinct application of the layers or due to differing properties between layers.

Additionally, as used herein, "tissue ingrowth" and "cellular penetration" refer to any presence or penetration of a biological or bodily material into a component of a medical appliance. For example, the presence of body tissues (e.g., collagen, cells, and so on) within an opening or pore of a layer or component of a medical appliance comprises tissue ingrowth into that component. Further, as used herein, "attachment" of tissue to a component of a medical appliance refers to any bonding or adherence of a tissue to the appliance, including indirect bonds. For example, tissue of some kind (e.g., collagen) may become attached to a stent covering (including attachment via tissue ingrowth) and another layer of biologic material (such as endothelial cells) may, in turn, adhere to the first tissue. In such instances, the second biologic material (endothelial cells in the example) and the tissue (collagen in the example) are "attached" to the stent covering.

Furthermore, through the present disclosure, certain fibrous materials (such as electrospun materials) may be referred to as inhibiting or promoting certain biological responses. These relative terms are intended to reference the characteristics of the fibrous materials with respect to non-fibrous materials or coatings. Examples of non-fibrous coatings include non-fibrous polytetrafluoroethylene (PTFE) sheets, other similarly formed polymers, and the like. Mats or other structures comprised of serially deposited fibers, such as microfibers and/or nanofibers are also examples of fibrous materials within the scope of this disclosure.

Serially deposited fiber mats or lattices refer to structures composed at least partially of fibers successively deposited on a collector, on a substrate, on a base material, and/or on previously deposited fibers. In some instances the fibers may be randomly disposed, while in other embodiments the alignment or orientation of the fibers may be somewhat controlled or follow a general trend or pattern. Regardless of any pattern or degree of fiber alignment, because the fibers are deposited on the collector, substrate, base material, and/or previously deposited fibers, the fibers are not woven, but rather serially deposited. Because such fibers are configured to create a variety of structures, as used herein, the terms "mat" and "lattice" are intended to be broadly construed as referring to any such structure, including tubes, spheres, sheets, and so on. Furthermore, the term "membrane" as used herein refers to any structure comprising serially deposited fibers having a thickness which is smaller than at least one other dimension of the membrane. Examples of membranes include, but are not limited to, serially deposited fiber mats or lattices forming sheets, strips, tubes, spheres, covers, layers, and so forth. Examples of serially deposited fibers include electrospun fibers and rotational spun fibers. Expanded PTFE does not comprise serially deposited fibers as used herein.

Lumens within the circulatory system are generally lined with a single layer (monolayer) of endothelial cells. This lining of endothelial cells makes up the endothelium. The endothelium acts as an interface between blood flowing through the lumens of the circulatory system and the inner walls of the lumens. The endothelium, among other functions, reduces or prevents turbulent blood flow within the lumen. The endothelium plays a role in many aspects of vascular biology, including atherosclerosis, creating a selective barrier around the lumen, blood clotting, inflammation, angiogenesis, vasoconstriction, and vasodilation.

A therapeutic medical appliance that includes a covering of porous or semi-porous material may permit the formation of an endothelial layer onto the porous surface of the blood contact side of the medical device. Formation of an endothelial layer on a surface, or endothelialization, may increase the biocompatibility of an implanted device. For example, a stent that permits the formation of the endothelium on the inside diameter (blood contacting surface) of the stent may further promote healing at the therapeutic region and/or have longer term viability. For example, a stent coated with endothelial cells may be more consistent with the surrounding body lumens, thereby resulting in less turbulent blood flow or a decreased risk of thrombosis, or the formation of blood clots. A stent that permits the formation of an endothelial layer on the inside surface of the stent may therefore be particularly biocompatible, resulting in less trauma at the point of application, fewer side effects, and/or longer term device viability. Medical appliances including a covering of porous or semi-porous material may be configured to inhibit or reduce inflammatory responses by the body toward the tissue contacting side of the medical appliance, for example. Mechanisms such as an inflammatory response by the body toward the medical appliance may stimulate, aggravate, or encourage negative outcomes, such as neointimal hyperplasia. For example, a device configured to permit tissue ingrowth and/or the growth or attachment of endothelial cells onto the blood contacting side of the device may reduce the likelihood of negative flow characteristics and blood clotting. Similarly, a device so configured may mitigate the body's inflammatory response toward the material on, for example, the tissue or non-blood contacting side of the device. By modulating the evoked inflammatory response, negative outcomes such as the presence of bioactive inflammatory macrophages and foreign body giant cells may be reduced. This may aid in minimizing the chemical chain of responses that may encourage fibrous capsule formation surrounding the device and events stimulating neointimal hyperplasia.

Electrospun materials, such as those described herein, may be used to comprise portions of medical appliances, such as stents, patches, grafts, and so forth. The present disclosure is applicable to any implantable medical appliance, notwithstanding any specific examples included below. In other words, though particular medical appliances, such as stents or patches, may be referenced in the disclosure and examples below, the disclosure is also analogously applicable to other medical appliances, such as those that comprise a covering or layer of polymeric material.

In some embodiments, electrospun nanofibers (and/or microfibers) may be configured to permit interaction with nanoscale (and/or microscale) body structures, such as endothelial cells. Electrospinning refers generally to processes involving the expulsion of flowable material from one or more orifices, the material forming fibers that are subsequently deposited on a collector, and wherein there is an electrostatic charge between any of the collector, the material, and the orifice. Examples of flowable materials include dispersions, solutions, suspensions, liquids, molten or semi-molten material, and other fluid or semi-fluid materials.

For example, one embodiment of an electrospinning process comprises loading a polymer solution or dispersion into a syringe coupled to a syringe pump. The material is forced out of the syringe by the pump in the presence of an electric field. The material forced from the syringe may elongate into fibers that are then deposited on a grounded collection apparatus. The system may be configured such that the material forced from the syringe is electrostatically charged, and thus attracted to the grounded collector. Exemplary methods and systems for electrospinning medical devices can be found in U.S. patent application Ser. No. 13/360,444, filed on Jan. 27, 2012 and titled "Electrospun PTFE Coated Stent and Method of Use," which is hereby incorporated by reference in its entirety.

Electrospinning may be configured to create mats, tubes, or other structures comprised of elongate fibers, including nanofibers (i.e., fibers that are smaller than 1 micron in diameter) or microfibers (i.e., fibers that are between 1 micron and 1 millimeter in diameter). In some instances the fibers may be randomly disposed, while in other embodiments the alignment or orientation of the fibers may be somewhat controlled or follow a general trend or pattern. Regardless of any pattern or degree of fiber alignment, as the fibers are deposited on a collector or on previously deposited fibers, the fibers are not woven, but rather are serially deposited on the collector or other fibers. Because electrospinning may be configured to create a variety of structures, as used herein, the terms "mat" and "non-woven mat or material" are intended to be broadly construed as referring to any such electrospun structure, including tubes, spheres, and so on.

The present disclosure relates to medical appliances that may have, in certain embodiments, metal scaffolding covered with at least one layer of electrospun material, such as electrospun PTFE. Additionally, the present disclosure relates to medical appliances formed of electrospun materials that may not have scaffolding structures or have scaffolding structures that are not made of metal. It will be appreciated that, though particular structures and coverings are described below, any feature of the scaffolding or covering described below may be combined with any other disclosed feature without departing from the scope of the current disclosure.

Figure 2:
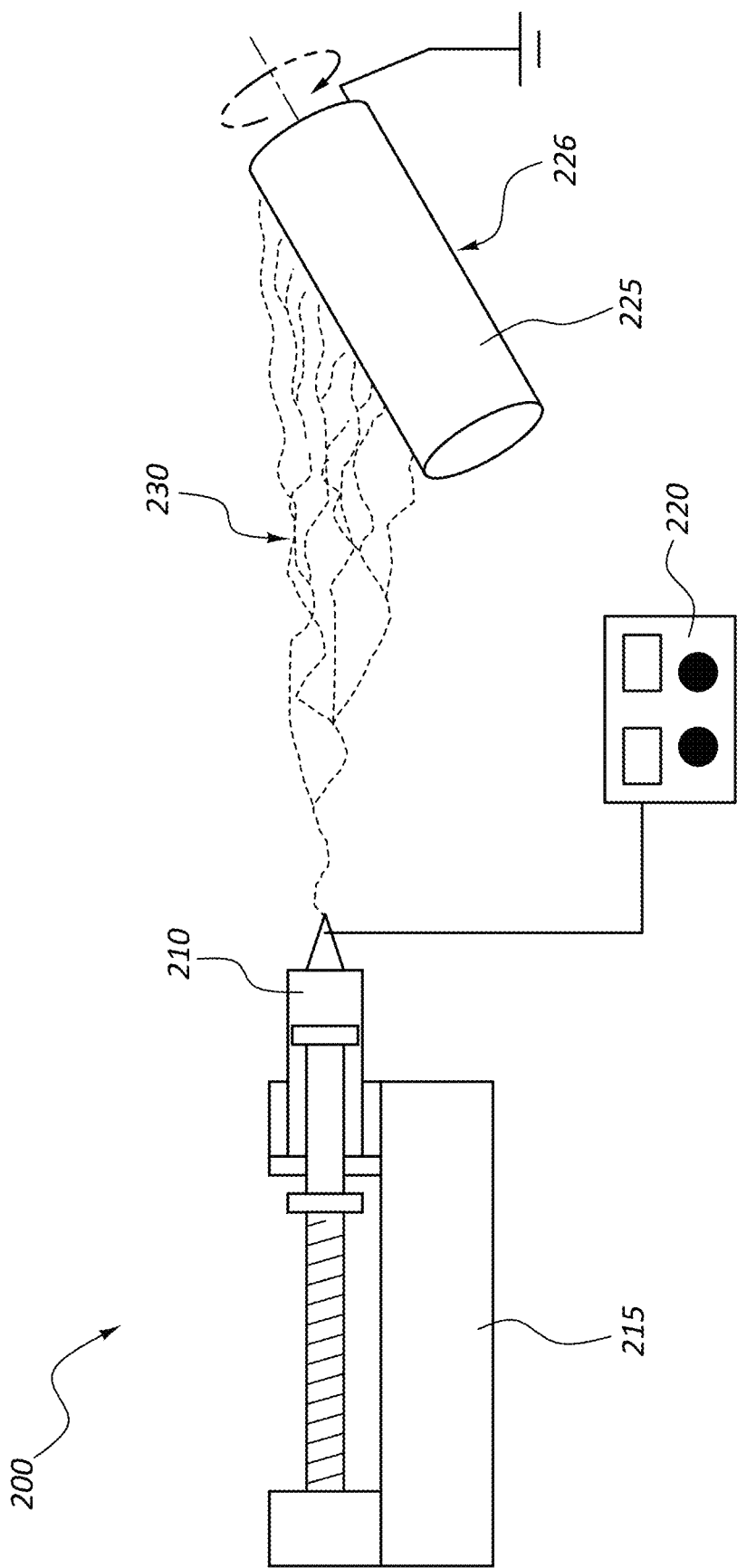
FIG. 2 is a schematic illustration of another embodiment of an electrospinning apparatus.
Figure 3A:
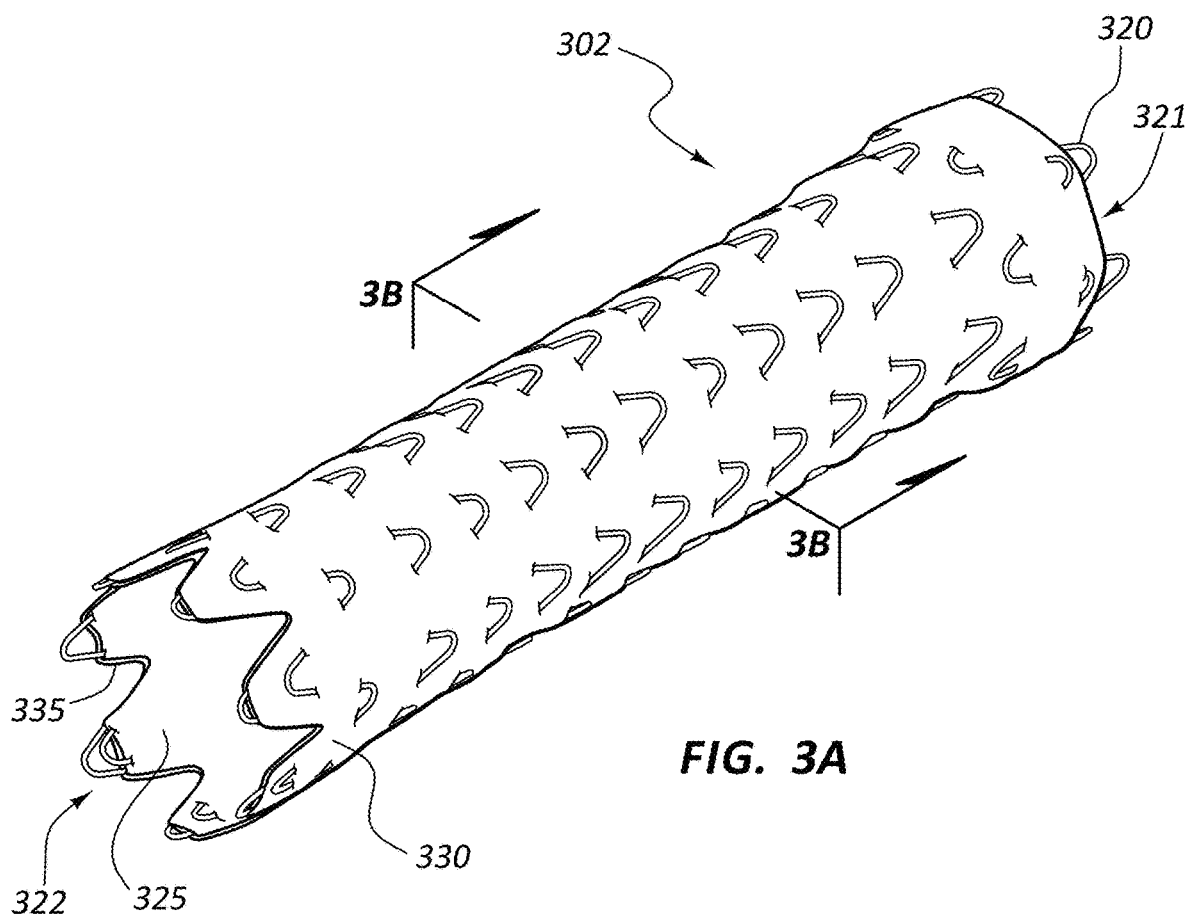
FIG. 3A is a perspective view of a covered stent.
Figure 3B:
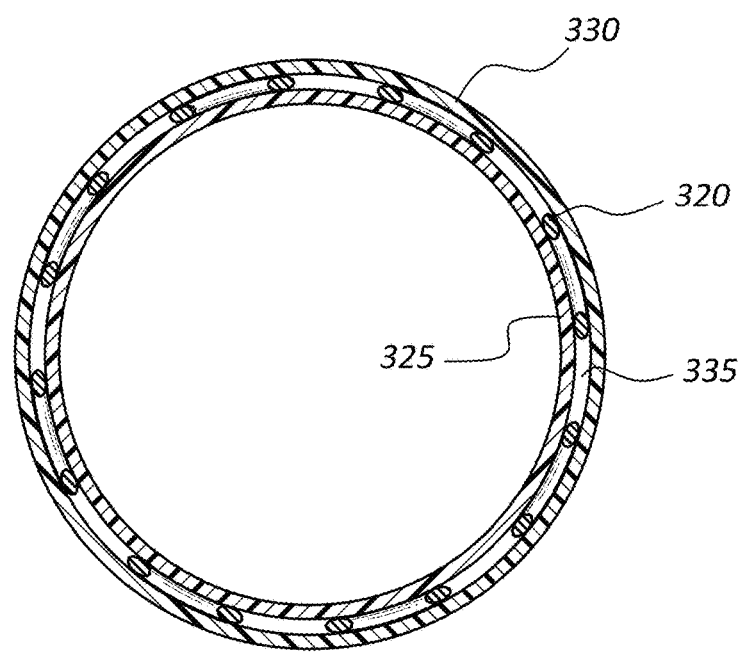
FIG. 3B is a cross-sectional view of the covered stent of FIG. 3A taken through line 3B-3B.

FIGS. 1 and 2 schematically illustrate certain embodiments of electrospinning apparatuses. FIGS. 3A and 3B illustrate an embodiment of a covered medical appliance. FIGS. 4A-4E illustrate certain steps in a process of manufacturing a multi-layered construct of electrospun materials. FIG. 5 illustrates an embodiment of a medical appliance that includes cuffs at each end of a stent. FIGS. 6-10 illustrate aspects of frames configured for use in connection with medical appliances. Finally, FIGS. 11A-12H are scanning electron micrographs (SEMs) of exemplary electrospun materials. Again, regardless of whether a medical appliance illustrated in any particular figure is illustrated with a particular covering or coating, or without any covering or coating at all, any embodiment of a medical appliance may be configured with any of the combinations of coverings or coatings shown or described herein.

Again, electrospinning generally references to processes configured to deposit fibers (including microfibers and nanofibers) on a collection apparatus in the presence of an electric field. Variations in the material to be electrospun (including density, viscosity, composition, and so forth) as well as variations in the electric field or other parameters of the electrospinning apparatus may be used to control or affect the deposition of fibers on the collector.

Membranes composed of electrospun PTFE or other materials may have a microstructure composed of numerous fibers crossing each other at various and random points. The electrospinning process may be configured to control the thickness of the mat, the density of the fiber pattern, the thickness of the fibers, the permeability of the mat, and so forth. In some instances, a thicker mat may tend to be less permeable, due to successive layers of fibers occluding the pores and openings of layers below.

FIG. 1 illustrates an electrospinning apparatus 100. This Figure, as well as FIG. 2, discussed below, is intended to schematically illustrate the operation of an electrospinning apparatus, and is not meant to limit the particular structure, shape, or arrangement of any electrospinning apparatus components within the scope of this disclosure. The illustrated apparatus 100 comprises a syringe 110 coupled to a syringe pump 115. In other embodiments, other pumps or devices may be configured to expel material from an orifice. A high voltage source 120 may be in communication with the syringe 110. Material to be electrospun may be discharged from the syringe 110 through operation of the syringe pump 115, and deposited on a collector 125. In the illustrated embodiment, the collector is grounded, thus creating an electrostatic potential between the high voltage source (and components in communication therewith) and the collector 125. Material discharged from the syringe 110 may form fibers 130 that are subsequently deposited on the collector 125. In some embodiments, the fibers 130 may be charged with respect to the grounded collector 125, and thus attracted to the collector 125 by electrostatic forces.

In one exemplary procedure, the syringe 110 may be loaded with a polymer dispersion and the syringe pump 115 configured to disburse the material at a constant rate. In one exemplary procedure this rate was set at 0.1 ml of material per minute. The syringe 110 was configured with a metal tip that was connected to the positive lead of the high voltage source 120. The collector 125 was placed about 7 inches from the syringe tip, and grounded. The voltage differential contributed in forcing the material from the syringe 110 to the collector 125 in nanoscale fibers.

The apparatus 100 may be utilized to create a mat of electrospun fibers deposited on the collector 125. In the illustrated embodiment, the collector 125 comprises a flat plate. In other embodiments, the collector may comprise other shapes, such as rods, spheres, curved surfaces, and so forth. Thus, in some embodiments, the collector 125 may be configured such that structures such as rods, tubes, or spheres of electrospun fibers are created.

In some embodiments, the apparatus 100 may be utilized to create a mat of electrospun fibers by first filling the syringe 110 with a flowable material. In some instances polymer dispersions, including aqueous dispersions or polymer solutions, may be used. The syringe pump 115 may then be operated such that the dispersion, or other flowable material, is forced out of the syringe 110. Molecules, including polymer chains, may tend to disentangle and/or align as the material is forced through an orifice of the syringe 110. In some embodiments the orifice of the syringe 110 may comprise a cannula configured with a quick connection, such as a luer connection, allowing for rapid exchange of various cannula sizes.

As the dispersion is expelled from the syringe 110, the stream or jet of material may elongate, forming a relatively small diameter fiber of material. Further, in some embodiments, the material may be electrically charged with respect to the collector 125. Thus, the material may be drawn to the collector 125 by electrostatic forces. The electrostatic forces may tend to stretch and/or elongate the material as the fibers 130 begin to form. The electrostatic forces may further affect the deposition of the fibers 130 on the collector 125. In some embodiments, the strength of the electrostatic field may be varied in connection with controlling the deposition of fibers 130 on the collector 125.

Additionally, certain components of the dispersion, such as the dispersion medium or solvent, may partially or fully evaporate as the material is drawn into the fibers 130. In embodiments utilizing flowable materials that have no solvent, such as molten material, there may be no evaporation as the material is drawn into the fibers 130.

Thus, the fibers 130 eventually contact, and are deposited on, the collector 125. The electrostatic forces, as well as the inertia of the material discharged from the syringe 110 and/or other forces such as drag on the fibers 130, may interact as the fibers 130 are deposited, causing the fibers 130 to be disposed in random patterns on the collector 125. In some embodiments, air currents may be introduced (for example through the use of fans) to partially control the deposition of the fibers 130 on the collector 125.

In embodiments utilizing certain flowable materials, the fibers 130 may then be removed from the collector 125 and sintered, or sintered and then removed. For example, sintering may be applicable to PTFE fibers, including PTFE fibers electrospun from a dispersion. The sintering process may set or bond the structure of the mat and remove any remaining water or other dispersion medium or solvent.

In some embodiments, the mat may be treated at a first temperature to remove solvents and a second temperature to sinter the mat. For example, a PTFE mat spun from an aqueous dispersion may be first treated at a temperature below the sintering temperature of PTFE in order to remove any remaining water. For example, the mat may be heated to about 200 degrees C. to remove any remaining water in the mat. Further, other materials such as solvents or fiberizing agents may be evaporated or otherwise driven off at this stage. In some embodiments—as further detailed below—a PTFE dispersion may be mixed with polyethylene oxide (PEO) prior to electrospinning the mat. Treating the spun mat at temperatures such as 200 degrees C. may force off remaining PEO as well as water. In some embodiments the PTFE mat may then be sintered at about 385 degrees C. In other embodiments, PTFE sintering may be completed at temperatures from about 360 degrees C. to about 400 degrees C., and/or at temperatures in excess of the crystalline melting point of the PTFE (about 342 degrees C.). In other instances the mat may only be heated to the sintering temperature, removing the remaining water and/or PEO while simultaneously sintering the PTFE. Additionally or alternatively, in some embodiments solvents or other materials may be removed by rinsing the mat.

Sintering may set the structure of the mat even if the temperature at which the material is sintered is not sufficient to cause cross-linking of the polymer chains. PTFE sintering may create solid, void-free, PTFE fibers.

The distance between the syringe 110 and the collector 125 may impact the diameter of the fibers 130 and/or the deposition of the fibers 130 on the collector 125. In some embodiments, variations to the degree of the electrostatic potential between these components may also impact the fiber diameter in connection with the distance between components.

Processes such as the exemplary process described above may be utilized to create structures comprised of small diameter fibers, including nanofibers. The fiber mat may then be incorporated into a medical appliance configured for implantation in the human body. Some such structures, including nanofiber structures, may be configured to permit tissue ingrowth and/or endothelial growth or attachment on the mat. For example, the mat may be configured with openings within the fibers or similar structures configured to permit interaction with tissue and/or cells. As further detailed below, the percent porosity of a fiber mat, the thickness of the mat, and the diameter of the fibers comprising the mat may each be configured to create a fiber mat with desired properties, including mats that tend to permit or resist tissue ingrowth and/or endothelial growth or attachment.

A number of variables may be controlled to affect the properties of an electrospun mat. Some of these variables include the strength of the electrostatic charge; the viscosity of the solution, dispersion, or other flowable material; the temperature of the syringe 110; introduced air currents; the thickness of the mat; and so on. In the case of fibers electrospun from molten material, the melt flow index (MFI) of the material may also impact the nature of the spun mat. In some embodiments, materials with an MFI of from about 1 g/10 min to about 5000 g/10 min, including from about 200 g/10 min to about 1500 g/10 min and from about 10 g/10 min to about 30 g/10 min, may tend to form fibers when spun.

In other embodiments an electrospun mat may be configured to resist tissue ingrowth into or through the mat. In such embodiments, the mat may be configured with very small pores, or essentially no pores at all, thus preventing tissue ingrowth into or through the mat. Certain medical appliances may be constructed partially of electrospun materials configured to permit tissue ingrowth and/or endothelial growth or attachment and partially of electrospun materials configured to resist tissue ingrowth and/or attachment. Characteristics of the electrospun fiber mat, such as porosity and average pore size, may be controlled during the electrospinning process to create certain mats that permit tissue ingrowth and/or endothelial growth or attachment and other mats that resist or are impermeable to tissue ingrowth and/or attachment.

In some embodiments, a PTFE dispersion may be used to electrospin a mat or another structure comprised of PTFE nanofibers. Furthermore, in some exemplary embodiments PEO may be added to the PTFE dispersion prior to electrospinning the material. The PEO may be added as a fiberizing agent, to aid in the formation of PTFE fibers within the dispersion or during the process of electrospinning the material. In some instances the PEO may more readily dissolve in the PTFE dispersion if the PEO is first mixed with water. In some examples this increased solubility may reduce the time needed to dissolve PEO in a PTFE dispersion from as long as multiple days to as little as 30 minutes. After the material is electrospun onto a collector, the material may then be sintered as further described below. In some instances the sintering process will tend to set or harden the structure of the PTFE. Furthermore, as described above, sintering may also eliminate the water and PEO, resulting in a mat of substantially pure PTFE. Additionally, as also described above, the mat may first be heat treated at a temperature below the sintering temperature of the PTFE, in order to remove water and/or PEO from the mat. In some embodiments this step may be completed at about 200 degrees C.

The water, PEO, and PTFE amounts may be controlled to optimize the viscosity, PEO/PTFE ratio, or other properties of the mixture. In some instances adding water to the PEO before mixing with the PTFE dispersion may aid in reducing the number of solid chunks or gels in the mixture, lower the preparation time for the mixtures, and reduce the time needed for the combined mixture to solubilize.

In one exemplary process, a 60 wt % PTFE water dispersion was mixed with PEO and water as follows. First, 5 ml of water was added to 1.4 g of PEO. The water and PEO were mixed until the PEO was fully dissolved and the solution created a thick gel. 30 ml of 60 wt % PTFE was then added to the PEO/water mixture. The combined solution was then allowed to sit or mix in a non-agitating jar roller until the solution achieved homogeneity. In other examples, the water, PEO, and PTFE amounts may be controlled to optimize the viscosity, PEO/PTFE ratio, or other properties of the mixture. In some instances adding water to the PEO before mixing with the PTFE dispersion may aid in reducing the number of large solid chunks in the mixture, lower the preparation time for the mixtures, and reduce the time needed for the combined mixture to solubilize. In other embodiments each of these materials, or sub-combinations thereof, may be placed in a jar roller for about three to about five days, after which time the mixture may be filtered through a 5 micron filter. Filtration may remove and/or break up any chunks or gels in the mixture. Other filters, for example 1 micron filters, may likewise be used.

A variety of materials may be electrospun to form structures for use in medical appliances. Exemplary materials that may be electrospun for use in implantable appliances include PTFE, fluorinated ethylene propylene (FEP), Dacron or polyethylene terephthalate (PET), polyurethanes, polycarbonate polyurethanes, polypropylene, Pebax, polyethylene, biological polymers (such as collagen, fibrin, and elastin), and ceramics.

Furthermore, additives or active agents may be integrated with the electrospun materials, including instances where the additives are directly electrospun with other materials. Such additives may include radiopaque materials such as bismuth oxide, antimicrobial agents such as silver sulfadiazine, antiseptics such as chlorhexidine or silver, and anticoagulants such as heparin. Organic additives or components may include fibrin and/or collagen. In some embodiments, a layer of drugs or other additives may be added to an electrospun appliance during manufacture. Additionally, some appliances may be constructed with a combination of synthetic components, organic components, and/or active ingredients including drugs, including embodiments wherein an appliance is comprised of alternating layers of these materials. Moreover, in some embodiments a medical appliance may consist of layers of electrospun materials configured to control the release of a drug or another active layer disposed between such layers. Active layers or ingredients such as drugs or other active agents may be configured to reduce or otherwise modify or influence the biological response of the body to the implantation of the medical appliance.

Additionally, in some embodiments the material supplied to the syringe 110 may be continuously supplied (for example by a feed line), including embodiments where the syringe 110 is pressurized or supplied by a pressurized source. Additionally, other discharge mechanisms (such as a pump) may be used to discharge material to be electrospun. Further, in some embodiments the material may be heated near or above its melting point prior to electrospinning, including embodiments wherein the material is melted and not dispersed in a solvent. Thus, in some embodiments, electrospinning molten material does not include the use of solvents; therefore there is no need to remove solvents from the mat at a later step in the process. In some instances the material may be supplied to the syringe or other reservoir as pellets that are heated and melted within the reservoir.

Another schematic embodiment of an electrospinning apparatus is shown in FIG. 2. It shows an apparatus 200, analogous to that shown in FIG. 1. It will be appreciated by one of skill in the art having the benefit of this disclosure that analogous components of the two apparatuses may be interchangeable and that disclosure provided in connection with each embodiment may be applicable to the other and vice versa.

FIG. 2 is a schematic diagram of an electrospinning apparatus 200 comprising a syringe 210 coupled to a syringe pump 215. A high voltage source 220 may be in communication with the syringe 210. Material to be electrospun may be discharged from the syringe 210 through operation of the syringe pump 215, and deposited on a collector 225. As with the embodiment of FIG. 1, in the embodiment of FIG. 2, the collector is grounded, thus creating an electrostatic potential between the high voltage source 220 (and components in communication therewith) and the collector 225. Material discharged from the syringe 210 may form fibers 230 that are subsequently deposited on the collector 225. Again, in some embodiments, the fibers 230 may be charged with respect to the grounded collector 225, and thus attracted to the collector 225 by electrostatic forces.

As compared to the apparatus 100 of FIG. 1, in the embodiment of FIG. 2 the collector 225 comprises a rotating mandrel 226 as opposed to a flat plate. In other embodiments, other shapes or types of collectors may be used. Thus, any collection device or apparatus is within the scope of this disclosure, regardless of the particular size, shape, or orientation of the collector. In some embodiments, a collector may comprise multiple elements, such as multiple cylinders or plates. In still other embodiments, the collector may comprise a rotating belt (not shown), configured to facilitate electrospinning of a continuous sheet of material.

In the embodiment of FIG. 2, the collector 225 comprises a mandrel 226 that may be configured to rotate about its longitudinal axis. In embodiments wherein such a mandrel is configured to rotate during the electrospinning process, the system may be configured to produce a seamless tube of electrospun material on the mandrel 226. Additionally, some embodiments may comprise more than one mandrel for use in connection with the electrospinning system. In the illustrated embodiment, the mandrel 226 is disposed horizontally. In another exemplary embodiment, the mandrel 226 may be disposed vertically. In some embodiments, the rotational speed of the mandrel 226 may affect the degree to which fibers deposited thereon tend to be aligned.

In addition to horizontal mandrels, further embodiments may comprise mandrels disposed in any relative position. Mandrels mounted in any disposition may be configured as stationary collection devices or configured to rotate. Additionally, combinations of mandrels in a variety of positions may be used simultaneously. Furthermore, in some embodiments one or more mandrels may be configured for use in connection with a vacuum system. For example, openings in the surface of the mandrel, such a micro-porous mandrel, may tend to draw fibers toward the mandrel in instances where the interior of the mandrel has lower pressure than the exterior of the mandrel. Additionally, in some embodiments fans or other devices may be configured to create air currents to direct or otherwise influence the deposition of fibers on the mandrel.

In embodiments wherein the mandrel 226 is configured to rotate, the spinning motion of each mandrel 226 may tend to deposit the fibers 230 around the entire surface of the mandrel 226. Thus, as the fibers 230 are deposited on the mandrel 226, a seamless tube of nanofiber material may form on the mandrel 226. The density of the fibers 230, the thickness of the mat, and other characteristics may be controlled by such variables as the distance from the syringe 210 to the mandrel 226, the magnitude of the electrostatic charge, the rotational speed of the mandrel 226, the orientation of the mandrel 226, the characteristics of the solution being spun, and so forth. In some instances, mats of electrospun material formed on a spinning mandrel 226 may thus comprise a tubular membrane having no seam and substantially isotropic properties. In some instances the collection mandrel 226 may rotate at rates between about 1 RPM and about 10,000 RPM during the electrospinning process, including rates from about 1500 RPM to about 5000 RPM or at about 5000 RPM for more aligned fibers and from about 50 RPM to about 500 RPM or at about 250 RPM for more random fiber orientation.

Furthermore, controlling the rotational speed of the mandrel 226 may influence both the density of the mat formed on the mandrel 226 and the general alignment of the fibers 230 in the mat. For instance, in some embodiments utilizing vertical mandrels, the faster the mandrel 226 is spinning the more the fibers 230 may tend to be deposited in-line with other fibers 230. Further, the relative density of the fibers 230, for example, as measured by percent porosity, may be controlled in part by the rotational speed of the mandrel 226.

As further detailed in connection with FIGS. 4A-4E, once the fibers 230 are electrospun onto the mandrel 226 the fibers 230 may be sintered. In some embodiments a scaffolding structure, such as a stent wire, may also be on the mandrel 226, and the fibers 230 electrospun directly onto the mandrel 226 and scaffolding structure.

In addition to mandrels, some systems may be configured to form a continuous sheet of electrospun material, including mats from about 1 meter to about 9 meters wide, such as mats of about 3 meters wide. Also mats from about 1 foot wide to about 1 meter wide (as well as larger or smaller mats) may be formed. In some instances, a sintering oven may be positioned such that as the mat moves away from the electrospinning apparatus (for example, on the belt) the mat enters the oven and is sintered. The sintered mat may then be collected onto a spool. Further, in some embodiments, the entire spool may then be cut into smaller widths, forming strips of material. For example, strips from about 0.1 inch wide to about 2 inches wide may be formed. Additionally, smaller strips, for example about 0.1 inch wide, or larger strips, for example about 12 inches wide, may be formed. Such strips may be utilized for the construction of tubular appliances by wrapping the strips around a mandrel. The strips may overlap and/or may be wound such that the tube formed does not have a distinct seam along the length of the tube. In some instances, the mat may be wound in multiple layers around the mandrel. Further, the mat formed may be relatively thin, or film-like. The thickness of the covering formed on the mandrel (and other characteristics such as porosity) may be controlled by the number of layers of film wound onto the mandrel. Film layers of differing materials may also be added to create a covering with particular properties. For example, Kapton and/or FEP may be added to increase strength in some instances.

In some embodiments, electrospun tubular medical devices, such as stents, may comprise one or multiple bifurcations or branches. Thus, medical devices that comprise a single lumen that splits or bifurcates into two or more lumens are within the scope of this disclosure. Likewise, medical appliances comprising a main lumen with one or multiple branch lumens extending from the wall of the main lumen are within the scope of this disclosure. For example, a thoracic stent—configured for deployment within the aorta—may comprise a main lumen configured to be disposed in the aorta and branch lumens configured to extend into side branch vessels originating at the aorta. Similarly, in some embodiments such stents may alternatively be configured with access holes in the main lumen configured to allow access (possibly for additional stent placement) and flow from the main vessel to any branch vessels extending therefrom.

In some embodiments, a bifurcated medical appliance may be manufactured by first creating a bifurcated mandrel in which the bifurcated mandrel portions are removable from the portion of the mandrel coinciding with the main lumen. The leg or branch portions of the mandrel may be splayed 180 degrees apart with a common axis of rotation. Thus, in some embodiments, the entire mandrel may form a T-shape. The entire mandrel may then be rotated about the axis of the leg portions and electrospun fibers collected on the leg portions of the mandrel. The mandrel may then be oriented to rotate about the axis of the main lumen portion of the mandrel, and any unwanted fibers disposed while spinning on the bifurcated leg portions may be wiped off. The mandrel may then be rotated about the axis of the main lumen portion and fibers collected on the main lumen portion of the mandrel. The entire mandrel may then be placed in an oven and sintered. The mandrel portions associated with the bifurcated legs may then be removed from the leg or branch portions of the appliance, and the single lumen mandrel portion subsequently removed from the spun appliance. The appliance may then be placed on or within a frame structure, such as a stent frame. A dip, spray, or film coating (such as of FEP or PTFE) may then be applied over the construct to create an impervious layer and/or to further bond the frame to the spun portion of the appliance.

In any of the exemplary embodiments or methods disclosed herein, in instances where the nanofibers are formed of PTFE, the sintering temperature may be from about 360 degrees C. to about 400 degrees C., including at temperatures of about 385 degrees C. or at temperatures above the crystalline melting temperature of the PTFE, or about 342 degrees C. Similarly, for other materials, sintering may be done at or above the crystalline melting temperature of other spun polymers. Again, either prior to or as part of the sintering process, heat treating may be configured to remove PEO and/or water, in instances where the PTFE or other polymer was combined with such elements prior to spinning the mat.

FIGS. 3A and 3B illustrate an exemplary medical appliance: a stent 302. The stent 302 comprises a scaffolding structure 320 and a covering comprising an inner layer 325, an outer layer 330, and a tie layer 335. In other embodiments, a stent covering may have more or fewer layers than the illustrated embodiment, including embodiments with only one covering layer. Again, disclosure recited herein with respect to specific medical appliances, such as stents, may also be applicable to other medical appliances.

The cover of the stent 302 of FIG. 3A comprises a flat end 321 and a scalloped end 322. At the flat end 321 of the illustrated embodiment, the cover of the stent 302 is cut substantially perpendicular to the longitudinal axis of the stent 302. At the scalloped end 322, the cover of the stent 302 comprises cut away, or scalloped, portions at the end of the stent 302. Scalloped ends may be configured to reduce infolding of the stent cover at the ends. For example, in some instances, a stent may have a larger diameter than a vessel in which it is deployed. Thus, the vessel may partially compress the stent radially. In some instances this radial compression may create folds or wrinkles in flat cut stent covers. These folds may then impede blood flow or lead to clotting within the vessel. Scalloped ends may reduce the occurrence of infolding at the end of a radially compressed stent. It is within the scope of this disclosure to use either type of end on any end of any stent.

Membranes composed of electrospun mats may have a microstructure composed of many fibers crossing each other at various and random points. The electrospinning process may control the thickness of this structure and thereby the relative permeability of the mat. As more and more fibers are electrospun onto a mat, the mat may both increase in thickness and decrease in permeability (due to successive layers of strands occluding the pores and openings of layers below). Certain details of this microstructure are shown in FIGS. 11A-12H, which are discussed in more detail below.

Mats produced in connection with the present disclosure may be described by three general parameters: percent porosity, mat thickness, and fiber diameter. Each of these parameters may impact the nature of the mat, including the tendency of the mat to permit tissue ingrowth and/or endothelial attachment or the tendency of the mat to resist tissue ingrowth or endothelial attachment. Each of these parameters may be optimized with respect to each other to create a mat having particular characteristics.

Percent porosity refers to the percent of open space to closed space (or space filled by fibers) in a fiber mat. Thus, the more open the mat is, the higher the percent porosity measurement. In some instances, percent porosity may be determined by first obtaining an image, such as an SEM, of an electrospun material. The image may then be converted to a "binary image," or an image showing only black and white portions, for example. The binary image may then be analyzed and the percent porosity determined by comparing the relative numbers of each type of binary pixel. For example, an image may be converted to a black and white image wherein black portions represent gaps or holes in the electrospun mat while white portions represent the fibers of the mat. Percent porosity may then be determined by dividing the number of black pixels by the number of total pixels in the image. In some instances, a code or script may be configured to make these analyses and calculations.

In some embodiments, percent porosities from about 30% to about 80% may be configured to permit tissue ingrowth into the layer and/or permit endothelial growth or attachment on the layer, including mats of about 40% to about 60%, mats of about 45% to about 50%, or mats of about 50% porosity. Less open layers may be configured to resist such ingrowth and/or attachment. Because the fibers comprising the mat are deposited in successive layers, the second parameter, mat thickness, may be related to porosity. In other words, the thicker the mat, the more layers of fibers and the less porous the mat may be. In some embodiments, mats from about 20 micrometers to about 100 micrometers may be configured for use in connection with the present disclosure, including mats from about 40 micrometers to about 80 micrometers. Finally, the third parameter, fiber diameter, may be a measurement of the average fiber diameter of a sample in some instances. In some embodiments fiber diameters from about 50 nanometers to about 3 micrometers may be used in connection with the present disclosure. Notwithstanding these or other specific ranges included herein, it is within the scope of this disclosure to configure a mat with any combination of values for the given parameters.

In some embodiments the "average pore size" of the mat may be used as an alternative or additional measurement of the properties of the mat. The complex and random microstructure of electrospun mats presents a challenge to the direct measurement of the average pore size of the mat. Average pore size can be indirectly determined by measuring the permeability of the mat to fluids using known testing techniques and instruments. Once the permeability is determined, that measurement may be used to determine an "effective" pore size of the electrospun mat. As used herein, the "pore size" of an electrospun mat refers to the pore size of a membrane that corresponds to the permeability of the electrospun mat when measured using ASTM standard F316 for the permeability measurement. This standard is described in ASTM publication F316, "Standard Test Methods for Pore Size Characteristics of Membrane Filters by Bubble Point and Mean Flow Pore Test," which is incorporated herein by reference. In some instances this test can be used as a quality control after configuring a mat based on the three parameters (percent porosity, thickness, and fiber diameter) discussed above.

In some applications it may be desirable to create a medical appliance such as stent 302 with an outer layer 330 that is substantially impermeable. Such an impermeable outer layer 330 may decrease the incidence of lumen tissue surrounding the stent 302 growing into or attaching to the stent 302. This may be desirable in applications where the stent 302 is used to treat stenosis or other occlusions; an impermeable outer layer 330 may prevent tissue from growing into or through the material toward or into the lumen of the stent 302 and reblocking or restricting the body lumen. In some embodiments a substantially impermeable outer layer 330 may be produced by using electrospun mats with a percent porosity from about 0% to about 50%, including about 25%; a thickness from about 20 micrometers to about 100 micrometers, including from about 40 micrometers to about 80 micrometers; and fiber diameters from about 50 nanometers to about 3 micrometers.

Additionally, or alternatively, a substantially impermeable mat may have an average pore size of about 0 microns to about 1.5 microns. In other embodiments, an impermeable layer may have an average pore size of less than about 0.5 micron. In yet other embodiments, an impermeable layer may have an average pore size of less than about 1 micron. In some embodiments, the impermeable layer may be a layer other than the outer layer, such as a tie layer, an intermediate layer, or an inner layer.

In one example, a medical appliance such as stent 302 may be covered with an electrospun PTFE inner layer 325 and an electrospun PTFE outer layer 330. The outer layer 330 may be configured to be substantially impermeable to tissue ingrowth and/or attachment. In other embodiments the impermeability of the stent 302 may be provided by a tie layer 335 disposed between the outer layer 330 and the inner layer 325. For example, a substantially impermeable layer may be formed of FEP that is applied, for example, as a film, spray, or dip coating between electrospun layers of PTFE. Furthermore, FEP may be electrospun with a small average pore size to create a substantially impermeable layer. In some embodiments both the outer layer 330 and the tie layer 335 may be configured to be substantially impermeable.

Dip coatings may be applied by dipping a portion of a layer or construct in a polymer dispersion. For example, a PTFE layer may be dip coated on a construct by adding 20 ml of water to 50 ml of a 60 wt % PTFE dispersion to thin the dispersion. A fiber mat may then be dipped in the solution to coat the mat. The dip coat may then be sintered at 385 degrees C. for 15 minutes. Other concentrations of PTFE dispersions for dip coatings are also within the scope of this disclosure.

Further, an FEP layer may be dip coated on a construct by adding 20 ml of water to 50 ml of a 55 wt % dispersion to thin the dispersion. A fiber mat may then be dipped in the solution to coat the mat. The dip coat may then be cooked, for example, at 325 degrees C. for 15 minutes. Other concentrations of FEP dispersions for dip coatings are also within the scope of this disclosure. Additionally, polymer dispersions may be sprayed or otherwise applied onto a surface (such as a fiber mat) to coat the surface. Such coatings may be heat treated after application.

In some embodiments, more or less water, for example from about 10 ml to about 50 ml, may be added to similar amounts and concentrations of the dip dispersions above to thin the dispersions. Additionally, substances other than, or in addition to, water may be used to thin a dispersion for dip coating. For example, a surfactant or a solvent may be used. In some such cases the surfactant or solvent may later be removed from the construct, including embodiments where it is allowed to evaporate when the coat is sintered or cooked. Alcohols, glycols, ethers, and so forth may be so utilized.

In some embodiments it may be desirable to create a medical appliance such as stent 302 with an outer layer 330 that is more porous. A porous outer layer 330 may permit healing and the integration of the prosthesis into the body. For instance, tissue of the surrounding lumen may grow into the porous outer diameter or attach to the outer diameter layer. This tissue ingrowth may permit, modulate, and/or influence healing at the therapy site. In some embodiments a porous outer layer 330 may be formed of electrospun PTFE.

In certain embodiments a relatively porous inner layer 325 may be desirable. This layer may or may not be used in conjunction with a substantially impermeable outer layer 330. A relatively porous inner layer 325 may permit tissue ingrowth and/or endothelial attachment or growth on the inside diameter of the stent 302 that may be desirable for any combination of the following: healing, biocompatibility, prevention of thrombosis, and/or reducing turbulent blood flow within the stent. In some embodiments the inner layer 325 may be comprised of a mat, such as an electrospun PTFE mat, having a percent porosity of about 40% to about 80%, including about 50%; a thickness of about 20 micrometers to about 100 micrometers, including from about 40 micrometers to about 80 micrometers; and fiber diameters from about 50 nanometers to about 3 micrometers.

Additionally, or alternatively, the mat may be comprised of an electrospun mat, such as PTFE, with an average pore size of about 1 micron to about 12 microns, such as from about 2 microns to about 8 microns, about 3 microns to about 5 microns, or about 3.5 microns to about 4.5 microns.

FIG. 3B illustrates a cross-sectional view of the stent 302 of FIG. 3A, again comprising a scaffolding structure 320 and covering comprising an inner layer 325, an outer layer 330, and a tie layer 335. Though in the illustration of FIG. 3B the tie layer 335 is shown at the same "level" as the scaffolding structure 320, the tie layer 335 may be above or below the scaffolding structure 320 in some embodiments. Further, as shown in FIG. 3B, each layer of the covering may be disposed so that there are no voids between layers.

In some embodiments the tie layer 335 may be configured to promote bonding between the outer layer 330 and the inner layer 325. In other embodiments the tie layer 335 may further be configured to provide certain properties to the stent 302 as a whole, such as stiffness or tensile strength. The tie layer 335 may thus be configured as a reinforcing layer. In some embodiments, expanded PTFE may be configured as a reinforcing layer. ePTFE may be anisotropic, having differing properties in differing directions. For example, ePTFE may tend to resist creep in the direction the ePTFE membrane was expanded. A reinforcing layer of ePTFE may be oriented to increase strength, resist creep, or impart other properties in a particular direction. ePTFE may be oriented such that the expanded direction is aligned with an axial direction of a medical device, a transverse direction, a radial direction, at any angle to any of these directions, and so forth. Similarly, multiple layers of ePTFE may be disposed to increase strength, resist creep, or impart other properties in multiple directions. The reinforcing layer may or may not be impermeable.

Additionally, in embodiments where both the inner layer 325 and the outer layer 330 are porous in nature, the tie layer 335 may be configured to create an impermeable layer between the two porous layers. In such embodiments the stent 302 may permit tissue ingrowth, tissue attachment, and/or healing on both the inner and outer surfaces of the stent 302 while still preventing tissue outside of the stent 302 from growing into the lumen and occluding the lumen. Thus, the tie layer 335 may be configured to create a mid-layer portion of a construct, the tie layer 335 configured to inhibit tissue ingrowth into the layer or to be impervious to tissue migration into or through the layer or to substantially inhibit tissue migration.

Furthermore, the tie layer 335 may be configured to be impervious or substantially impervious to fluid migration across the tie layer 335. Specifically, constructions comprising one or more porous layers may allow fluid to cross the porous layer. In the case of a medical appliance configured to control blood flow, such as a graft, a porous layer may allow blood to leak across the layer or may allow certain smaller components of the blood to cross the layer while containing larger components, effectively filtering the blood. In some instances this filtration or ultrafiltration may allow components such as plasma to cross the barrier while containing red blood cells, leading to seroma. Thus, a fluid impermeable tie layer may be configured to contain fluid within a medical device also comprised of porous layers. In some devices, a tie layer may be both fluid impermeable and impervious to tissue ingrowth, or may be configured with either of these properties independent of the other. Constructs wherein any layer (other than, or in addition to, a tie layer) is configured to be fluid impermeable and/or impervious to tissue ingrowth are also within the scope of this disclosure. Thus, disclosure recited herein in connection with fluid impermeable and/or tissue impervious tie layers may be analogously applied to impermeable layers at various locations within a construct.

The tie layer (or any impermeable/impervious layer) may include any thermoplastic and may or may not be electrospun. In one embodiment, the tie layer may be ePTFE. In another it may be electrospun PTFE. In other embodiments it may be FEP, including electrospun FEP and FEP applied as a film or dip coating. Furthermore, the tie layer may include any of the following polymers or any other thermoplastic: dextran, alginates, chitosan, guar gum compounds, starch, polyvinylpyridine compounds, cellulosic compounds, cellulose ether, hydrolyzed polyacrylamides, polyacrylates, polycarboxylates, polyvinyl alcohol, polyethylene oxide, polyethylene glycol, polyethylene imine, polyvinylpyrrolidone, polyacrylic acid, poly(methacrylic acid), poly(itaconic acid), poly(2-hydroxyethyl acrylate), poly(2-(dimethylamino)ethyl methacrylate-co-acrylamide), poly(N-isopropylacrylamide), poly(2-acrylamido-2-methyl-l-propanesulfonic acid), poly(methoxyethylene), poly(vinyl alcohol), poly(vinyl alcohol) 12% acetyl, poly(2,4-dimethyl-6-triazinylethylene), poly(3morpholinylethylene), poly(N-l,2,4-triazolyethylene), poly(vinyl sulfoxide), poly (vinyl amine), poly(N-vinyl pyrrolidone-co-vinyl acetate), poly(g-glutamic acid), poly(Npropanoyliminoethylene), poly(4-amino-sulfo-aniline), poly[N-(p-sulphophenyl) amino-3-hydroxymethyl-1,4phenyleneimino-l,4-phenylene], isopropyl cellulose, hydroxyethyl, hydroxylpropyl cellulose, cellulose acetate, cellulose nitrate, alginic ammonium salts, i-carrageenan, N-[(3'-hydroxy-2',3'-dicarboxy) ethyl]chitosan, konjac glocomannan, pullulan, xanthan gum, poly(allyammonium chloride), poly(allyammonium phosphate), poly(diallydimethylammonium chloride), poly(benzyltrimethylammonium chloride), poly(dimethyldodecyl(2-acrylamidoethyly) ammonium bromide), poly(4-N-butylpyridiniumethylene iodine), poly(2-N-methylpridiniummethylene iodine), poly(N methylpryidinium-2,5-diylethenylene), polyethylene glycol polymers and copolymers, cellulose ethyl ether, cellulose ethyl hydroxyethyl ether, cellulose methyl hydroxyethyl ether, poly(l-glycerol methacrylate), poly(2-ethyl-2-oxazoline), poly(2-hydroxyethyl methacrylate/methacrylic acid) 90:10, poly(2-hydroxypropyl methacrylate), poly(2-methacryloxyethyltrimethylammonium bromide), poly(2-vinyl1-methylpyridinium bromide), poly(2-vinylpyridine N-oxide), poly(2-vinylpyridine), poly(3-chloro-2-hydroxypropyl 2-methacryloxyethyldimethylammonium chloride), poly (4vinylpyridine N-oxide), poly(4-vinylpyridine), poly(acrylamide/2-methacryloxyethyltrimethylammonium bromide) 80:20, poly(acrylamide/acrylic acid), poly(allylamine hydrochloride), poly(butadiene/maleic acid), poly(diallyldimethylammonium chloride), poly(ethyl acrylate/acrylic acid), poly(ethylene glycol)bis(2-aminoethyl), poly(ethylene glycol)monomethyl ether, poly(ethylene glycol)bisphenol A diglycidyl ether adduct, poly(ethylene oxide-bpropylene oxide), poly(ethylene/acrylic acid) 92:8, poly(llysine hydrobromide), poly(l-lysine hydrobromide), poly(maleic acid), poly(n-butyl acrylate/2methacryloxyethyltrimethylammonium bromide), poly(Niso-propylacrylamide), poly (N-vinylpyrrolidone/2dimethylaminoethyl methacrylate), dimethyl sulfatequaternary, poly(N-vinylpyrrolidone/vinyl acetate), poly(oxyethylene) sorbitan monolaurate (Tween 20®), poly(styrenesulfonic acid), poly(vinyl alcohol), N-methyl-4(4'formylstyryl)pyridinium, methosulfate acetal, poly(vinyl methyl ether), poly(vinylamine) hydrochloride, poly(vinylphosphonic acid), poly(vinylsulfonic acid) sodium salt, and polyaniline.

Regardless of the material, the tie layer 335 may or may not be electrospun. Further, in certain embodiments the stent 302 may include two or more tie layers 335. The tie layer 335 may be formed in any manner known in the art and attached to the inner 325 and outer 330 layers in any manner known in the art. For example, the tie layer 335 may comprise a sheet of material that is wrapped around the inner layer 325 or a tube of material that is slipped over the inner layer 325 that is then heat shrunk or otherwise bonded to the inner 325 and outer 330 layers. Further, in embodiments where the tie layer is electrospun, it may be electrospun directly onto the inner layer 325, the scaffolding structure 320, or both. In some instances the tie layer 335 may be melted after the stent 302 is constructed to bond the tie layer 335 to adjacent layers of the stent covering.

Furthermore, the tie layer may be configured to change the overall properties of the medical appliance. For example, in some instances a cover or construct comprised solely of electrospun PTFE (of the desired pore size) may not have desired tensile or burst strength. A tie layer comprised of a relatively stronger material may be used to reinforce the PTFE inner layer, the PTFE outer layer, or both. For example, in some instances FEP layers may be used to increase the material strength of the cover. Again, as discussed above, the tie layer may also be configured as a portion of the construct configured to be impervious to tissue ingrowth or migration.

Further, one or more layers of electrospun PTFE may be used in connection with a scaffolding structure other than that shown herein. In other words, the disclosure above relating to covers, layers, tie layers, and related components is applicable to any type of scaffolding structure as well as to stents or grafts with no separate scaffolding structure at all.

FIGS. 4A-4E illustrate certain steps in a process of manufacturing a multilayer construct for use in connection with a medical appliance. More specifically, these Figures illustrate a process of creating a stent covered with electrospun material. Again, this disclosure is equally relevant to all medical appliances that may comprise a cover or multilayered construct, including grafts, patches, stents, and so on. Additionally, as suggested in the additional examples disclosed below, the illustrated steps may be optional in some instances or augmented by additional steps in others.

Figure 4A:
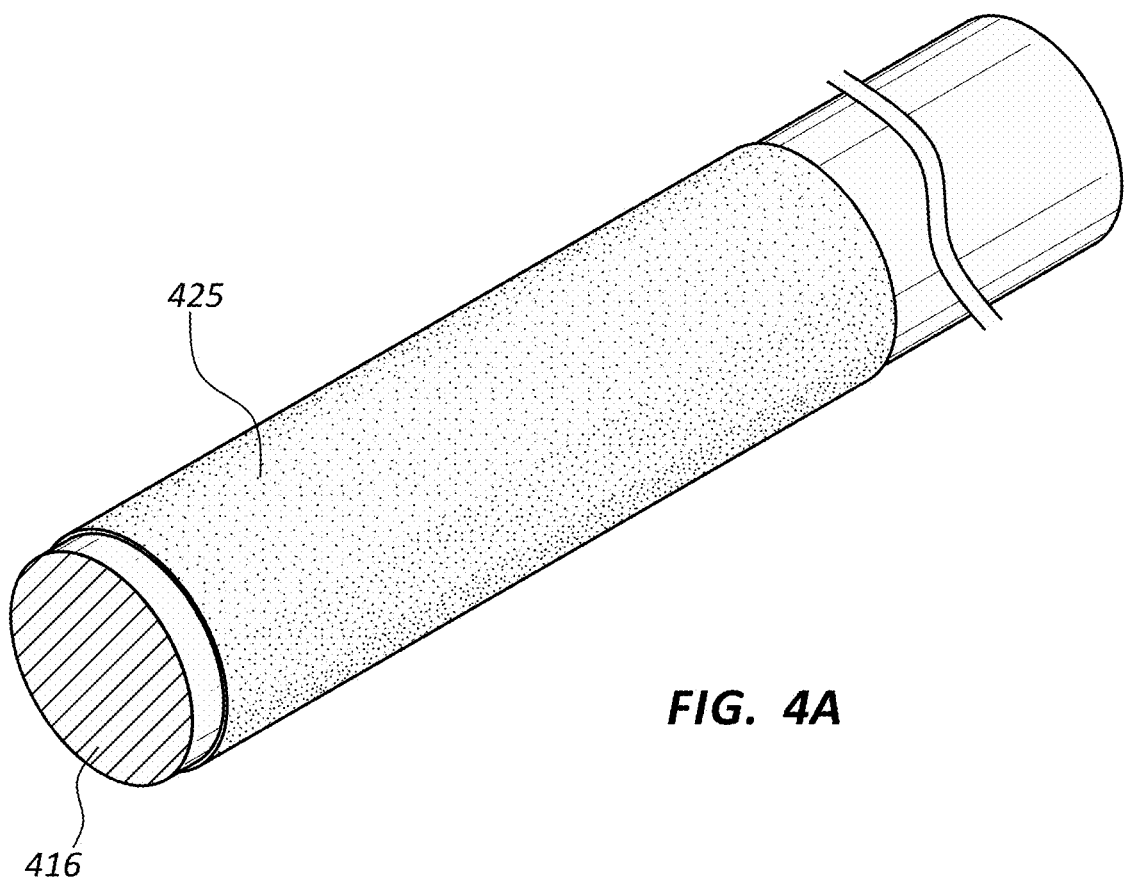
FIG. 4A is a perspective view of an electrospun covering on a mandrel.
Figure 5:
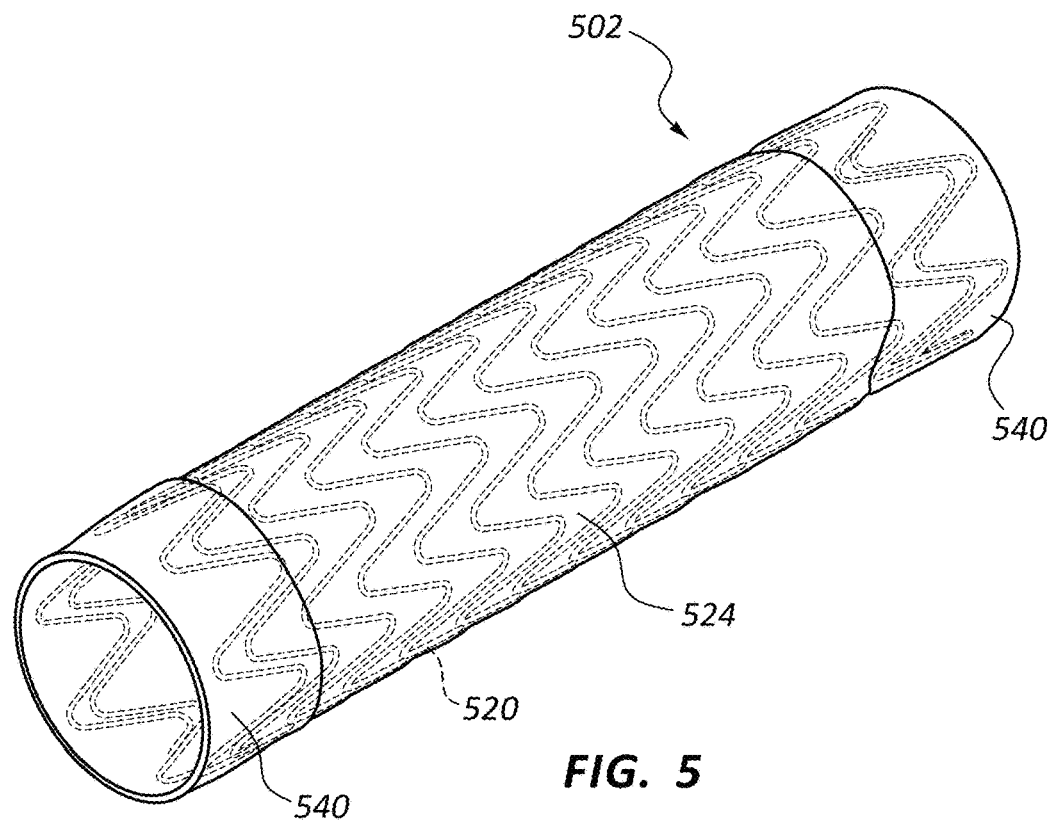
FIG. 5 is a perspective view of a covered stent including cuffs.

FIG. 4A illustrates a covering inner layer 425 disposed around a mandrel 416. As described above, the inner layer 425 may be electrospun directly onto the mandrel 416, including instances wherein the mandrel 416 was rotating during the process. In the illustrated embodiment, the inner layer 425 was electrospun onto a rotating mandrel 416 such that the resultant tube of material has no seam. After the inner layer 425 is electrospun onto the mandrel 416, the inner layer 425 may then be sintered. In the case of PTFE, the membrane may be sintered at temperatures of about 385 degrees C., including temperatures from about 360 degrees C. to about 400 degrees C. Sintering may tend to set the structure of the PTFE, meaning sintering reduces the softness or flowability of the PTFE. Furthermore, as discussed above, sintering or otherwise heat treating the mat may evaporate any water or PEO mixed with the PTFE, resulting in a material comprised substantially of pure PTFE.

Figure 4B:
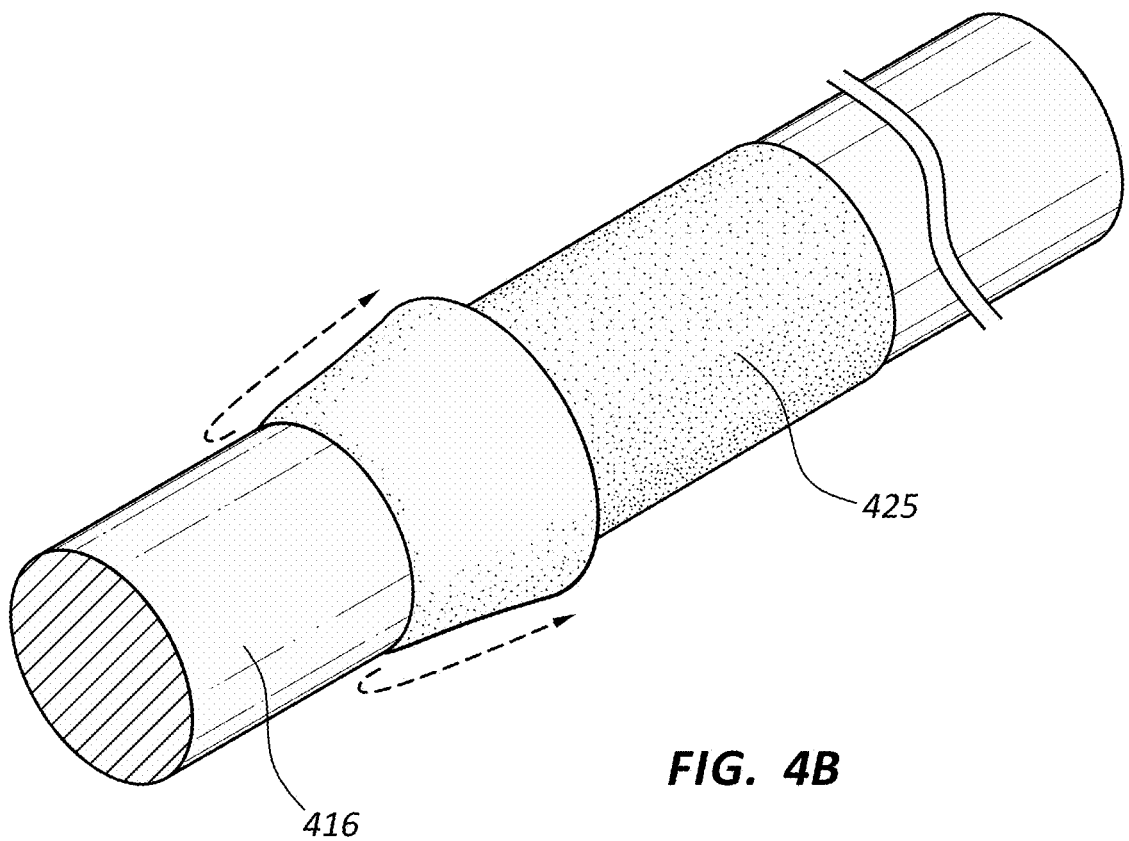
FIG. 4B is a perspective view of the covering of FIG. 4A partially removed from the mandrel.
Figure 4C:
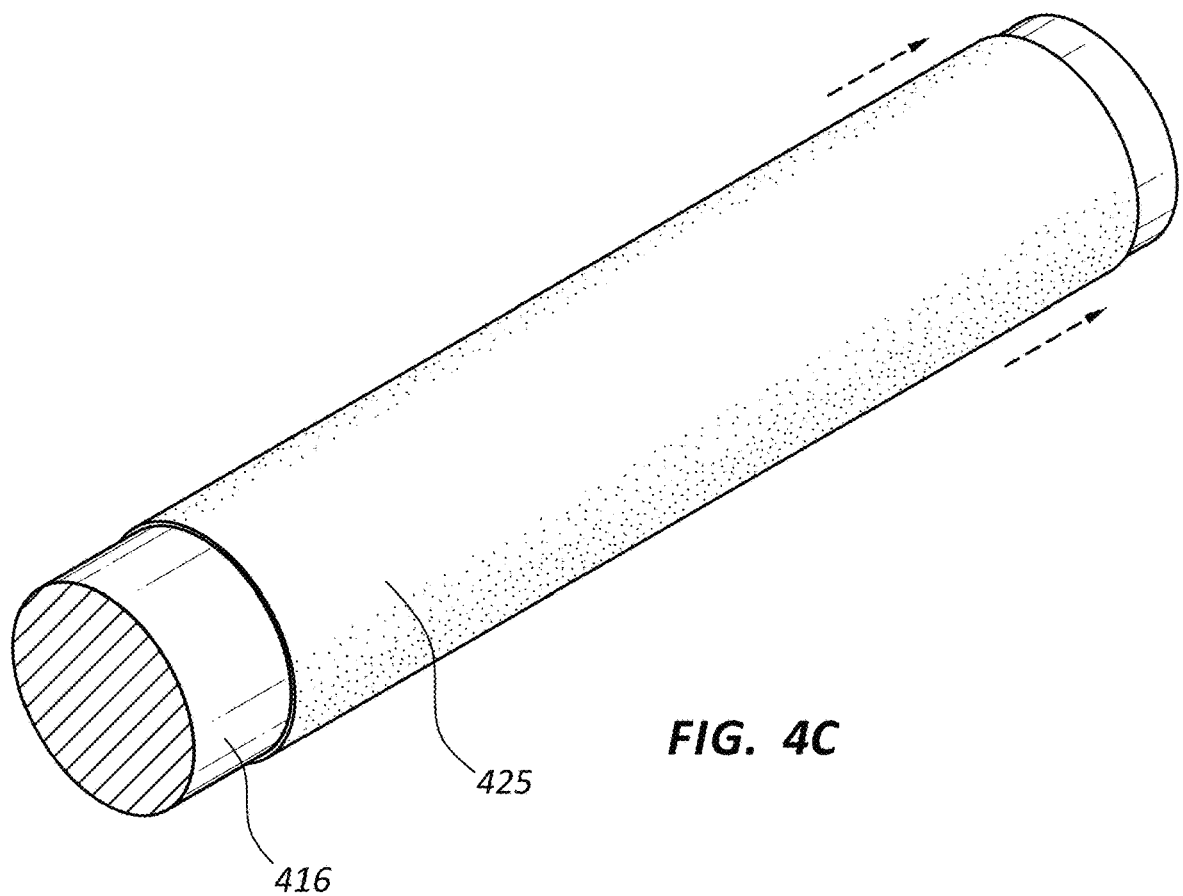
FIG. 4C is a perspective view of the covering of FIG. 4A repositioned on the mandrel.

Once the inner layer 425 is sintered, the tube of material may be removed from the mandrel 416, as illustrated in FIG. 4B. As shown in the illustrated embodiment, the inner layer 425 may be "peeled" from the mandrel 416 to initially break any adherence of the inner layer 425 to the mandrel 416. The inner layer 425 may also be removed by pushing the covering with respect to the mandrel 416, causing the material to bunch as it is removed from the mandrel 416. In some embodiments, low friction coatings may alternatively or additionally be applied to the mandrel 416 before the inner layer 425 is electrospun. The inner layer 425 may then be reapplied to the mandrel 416 by slipping the inner layer 425 over the mandrel 416, as illustrated in FIG. 4C.

Figure 4D:
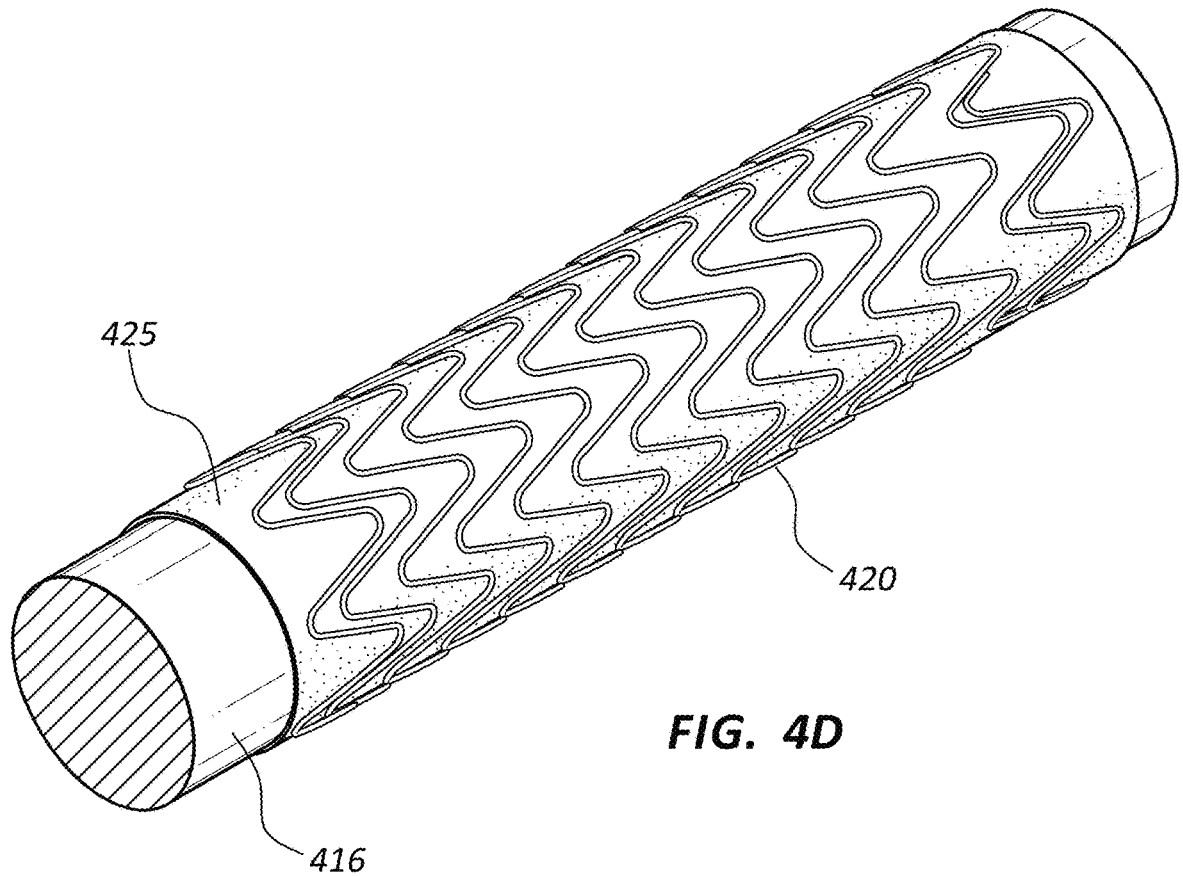
FIG. 4D is a perspective view of a scaffolding structure wound around the covering and mandrel of FIG. 4C.
Figure 4E:
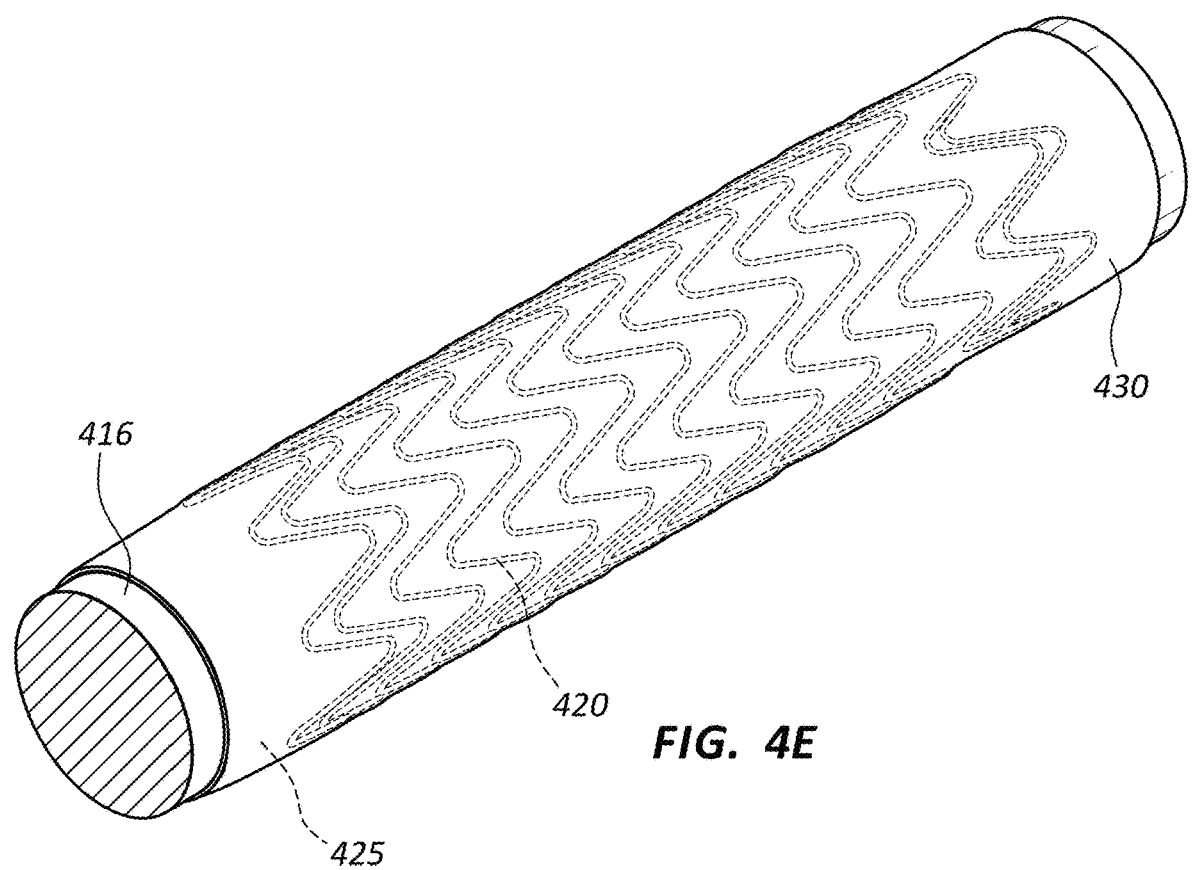
FIG. 4E is a perspective view of the scaffolding structure of FIG. 4D with a second electrospun covering.

Once the inner layer 425 is reapplied to the mandrel 416, a wire scaffolding 420 can be formed over the mandrel 416 and the inner layer 425, as shown in FIG. 4D. FIG. 4E illustrates an outer layer 430 of material that may then be electrospun onto the scaffolding 420 and the inner layer 425. The entire construct may then be sintered. Additional layers may also be added through similar processes.

Many variations to the above-described process are within the scope of the present disclosure. For example, one or more layers may be applied by wrapping strips or mats of material around the mandrel 416 and/or the other layers. Further, some of the layers may be applied by spray or dip coating the mandrel 416 and/or the other layers. It is within the scope of this disclosure to vary the process above to apply to any of the layers, or any additional layers, using any method disclosed herein.

In another example, a stent may be comprised of an inner layer of electrospun PTFE, a tie layer of FEP, and an outer layer of PTFE. The properties of each of these layers, including percent porosity, mat thickness, fiber diameter, and/or average pore size, may be controlled to form a covering layer that inhibits the growth of tissue into or through a particular layer or that permits endothelial growth or attachment on a particular layer.

In some such embodiments, the inner layer of PTFE may be electrospun on a mandrel, sintered, removed from the mandrel, and replaced on the mandrel and then a scaffolding structure applied around the inner layer (analogous to the procedure illustrated in FIGS. 4A-4D). The FEP tie layer may then be applied by dipping, spraying, applying a film layer, electrospinning, rotational spinning, extrusion, or other processing.

In some embodiments, the FEP layer may be heated such that the FEP becomes soft, in some cases flowing into open spaces in adjacent PTFE layers. This may tie the FEP layer to adjacent PTFE layers. In some instances, heating the construct to about 325 degrees C. may allow the FEP to partially flow into openings in adjacent PTFE layers, without the FEP completely flowing through the PTFE mat.

In another particular example, an inner layer of PTFE may be electrospun on a mandrel, sintered, removed, and replaced, and then a scaffolding structure applied around the inner layer. An FEP tie layer may then be applied as a film layer. In some instances this tie layer may be "tacked" into place, for example, by a soldering iron. A tube of PTFE (which may be formed separately by electrospinning onto a mandrel and sintering) may then be disposed over the FEP film layer. The entire construct may then be pressured, for example, by applying a compression wrap. In some embodiments this wrap may comprise any suitable material, including a PTFE-based material. In other embodiments a Kapton film may be wrapped around the construct before the compression wrap, to prevent the construct from adhering to the compression wrap.

The compressed layers may then be heated above the melting temperature of the FEP tie layer, but below the sintering temperature of the PTFE. For example, the melt temperature of the FEP may be from about 264 degrees C. to about 380 degrees C., including about 325 degrees C. PTFE may be sintered at temperatures from about 360 degrees C. to about 400 degrees C. Thus, the entire construct may be heated to an appropriate temperature such as about 325 degrees C. In some embodiments the construct may be held at this temperature for about 15 to about 20 minutes. Heating the FEP layer to about 325 degrees C. may allow the FEP layer to remain substantially impervious to tissue ingrowth and/or attachment, creating a "barrier" layer within the construct, while still adhering the FEP to adjacent layers of PTFE. In other embodiments, heating the construct to higher temperatures, such as about 350 degrees C. or more, may be configured to allow the FEP to flow around the PTFE such that the entire construct has a higher degree of porosity and the FEP layer is not as impervious to ingrowth.

The joining of the FEP tie layer to the PTFE outer and inner cover layers may increase the strength of the finished covering. The construct may then be cooled and the compression wrap and the Kapton film discarded. The construct may then be removed from the mandrel.

A stent formed by the exemplary process described above may be configured with desired characteristics of porosity and strength. In some instances the FEP material may coat the PTFE nanofibers but still allow for sufficient porosity to permit tissue ingrowth and/or endothelial attachment or growth. The degree to which the FEP coats the PTFE may be controlled by the temperature and time of processing. The lower the temperature and/or the shorter the time the construct is held at a certain temperature, the less the FEP may flow. In some instances a tie layer of FEP that is impervious to tissue ingrowth into or through the layer may be formed by heating the construction only to about 270 degrees C.

FIG. 5 illustrates a stent 502 that comprises a scaffolding structure 520 and a covering 524. The covering 524 may be comprised of any combination of layers disclosed herein. Additionally, the stent 502 of FIG. 5 includes a cuff 540 at both ends of the stent 502. In other embodiments a cuff 540 may be located at only one end of the stent 502.

The cuff 540 may comprise an additional covering layer on the outside diameter of the stent 502, disposed adjacent to one or both ends of the stent 502. The cuff 540 may be configured to promote tissue ingrowth, attachment, and/or incorporation into the cuff 540; for example, the cuff 540 may be more porous than an outer layer of the covering 524 of the stent 502. Factors such as porosity, type of covering or coating, type of material, use of organic material, and/or use of composite materials formed of synthetic material and organic material may be used to create a cuff 540 configured for tissue ingrowth. Again, the cuff 540 may be configured to promote tissue ingrowth and/or the growth or attachment of endothelial cells at one or both ends of the stent 502. When implanted in the body, the cuffs 540 may tend to "anchor" the ends of the stent 502 with respect to the vessel walls, reducing the relative movement of the stent ends with respect to the vessel walls. Such a reduction in movement may lessen irritation of the vessel by the stent ends, minimizing complications such as edge stenosis. Cuffs 540 may be configured for use in CV type applications in some instances. Furthermore, a band of porous material analogous to the cuff 540 illustrated may be coupled to any medical appliance to anchor a portion of such a device.

In some embodiments, the outer layer of the covering 524 of the stent 502 may be relatively non-porous to inhibit tissue ingrowth into or through the outer layer, but the cuff 540, disposed about the outer layer, may provide a section near each end at which some tissue ingrowth, attachment, or incorporation may occur.

The cuff 540 may be comprised of an electrospun material, such as PTFE, and may be bonded to the outer covering layer through any method, including methods of multilayer device construction described herein. For example, a layer of FEP may be disposed between the outer covering layer and the cuff 540, and heated to bond the layers. In other embodiments the cuff 540 may comprise a collagen layer that is coupled to the stent. Further, a co-electrospun collagen and PTFE cuff 540 may be utilized.

The current disclosure relates to medical appliances, including stents, which may comprise a frame structure provided in connection with one or more coverings or coatings. It will be appreciated that, though particular structures, coverings, and coatings are described herein, any feature of the frames or coverings and/or coatings described herein may be combined with any other disclosed feature without departing from the scope of the current disclosure. For example, certain Figures referenced below show a metal frame without any covering or coating; the features described and illustrated in those Figures may be combined with any combination of coverings or coatings disclosed herein. Further, as used herein, the term "frame" refers to a support structure for use in connection with a medical appliance. For instance, a scaffolding structure, such as that described in connection with FIGS. 4A-4E, above, is an example of a frame used in connection with a medical appliance. In some embodiments, a medical appliance—such as a stent—may comprise a frame alone, with no covering, coating, or other components.

Moreover, the current disclosure is applicable to a wide variety of medical appliances that may utilize any of the electrospun mats disclosed herein, including medical appliances that comprise multiple layers. For example, a hernia patch may comprise a two-layered construction, with one side of the patch configured to allow tissue ingrowth and/or attachment (for bonding and healing) and the other side configured to resist such ingrowth and/or attachment (to make the second side "slippery" with respect to surrounding tissue). Further, a patch as described above may also comprise a tie layer disposed between the two exterior layers. The tie layer may be configured to resist tissue ingrowth or attachment into or through the patch and/or to provide mechanical properties such as strength to the construct.

Figure 6:
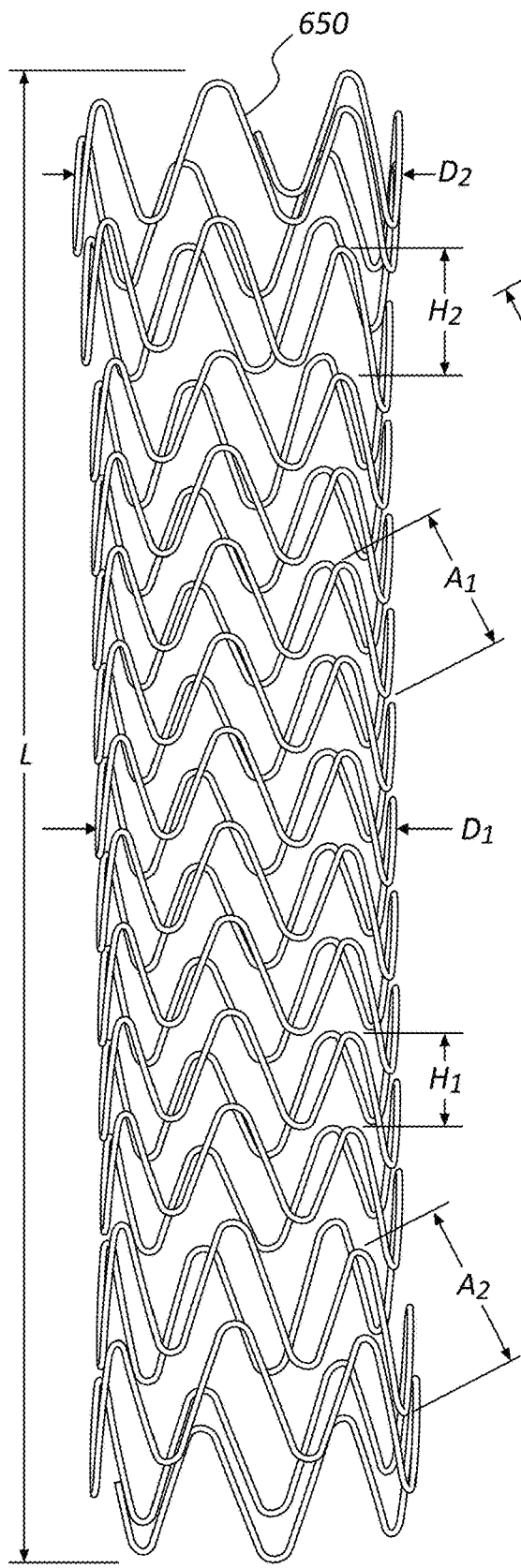
FIG. 6 is a front view of a medical appliance frame structure.
Figure 7A:
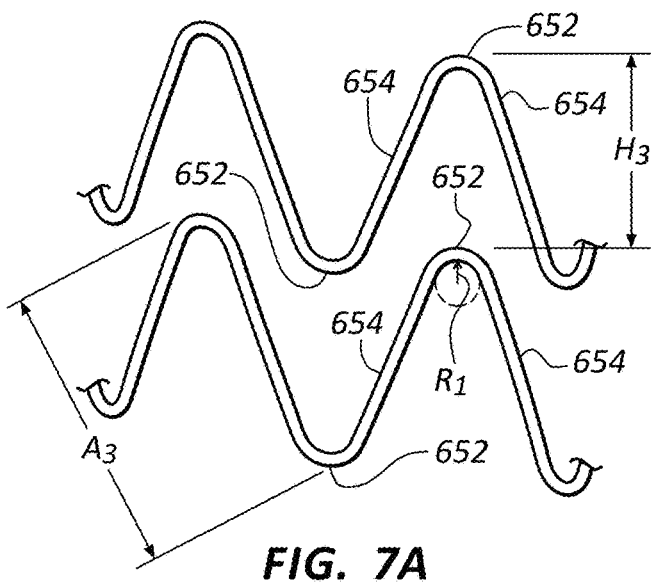
FIG. 7A is a detail view of a portion of the frame of FIG. 6.
Figure 7B:
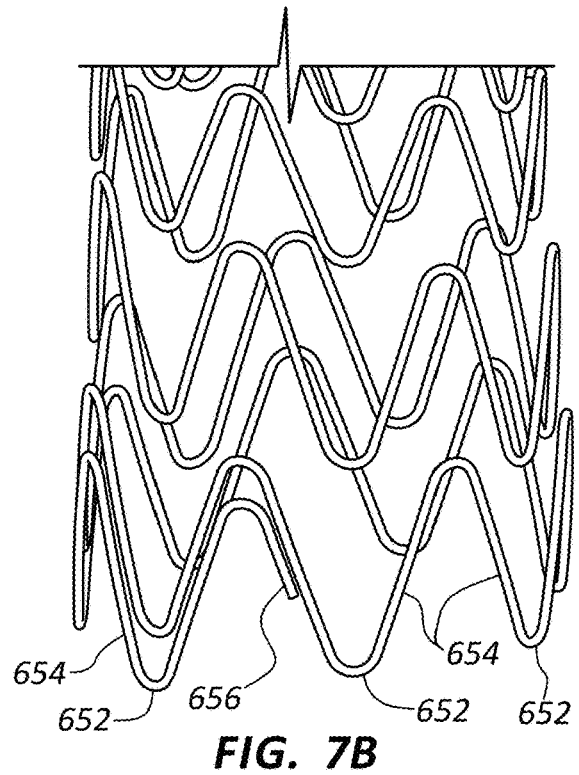
FIG. 7B is a detail view of an end of the frame of FIG. 6.
Figure 7C:
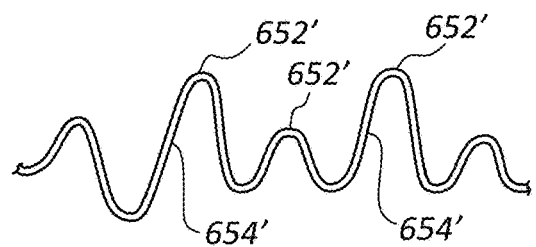
FIG. 7C is an alternative configuration of a portion of the frame of FIG. 6.
Figure 8:
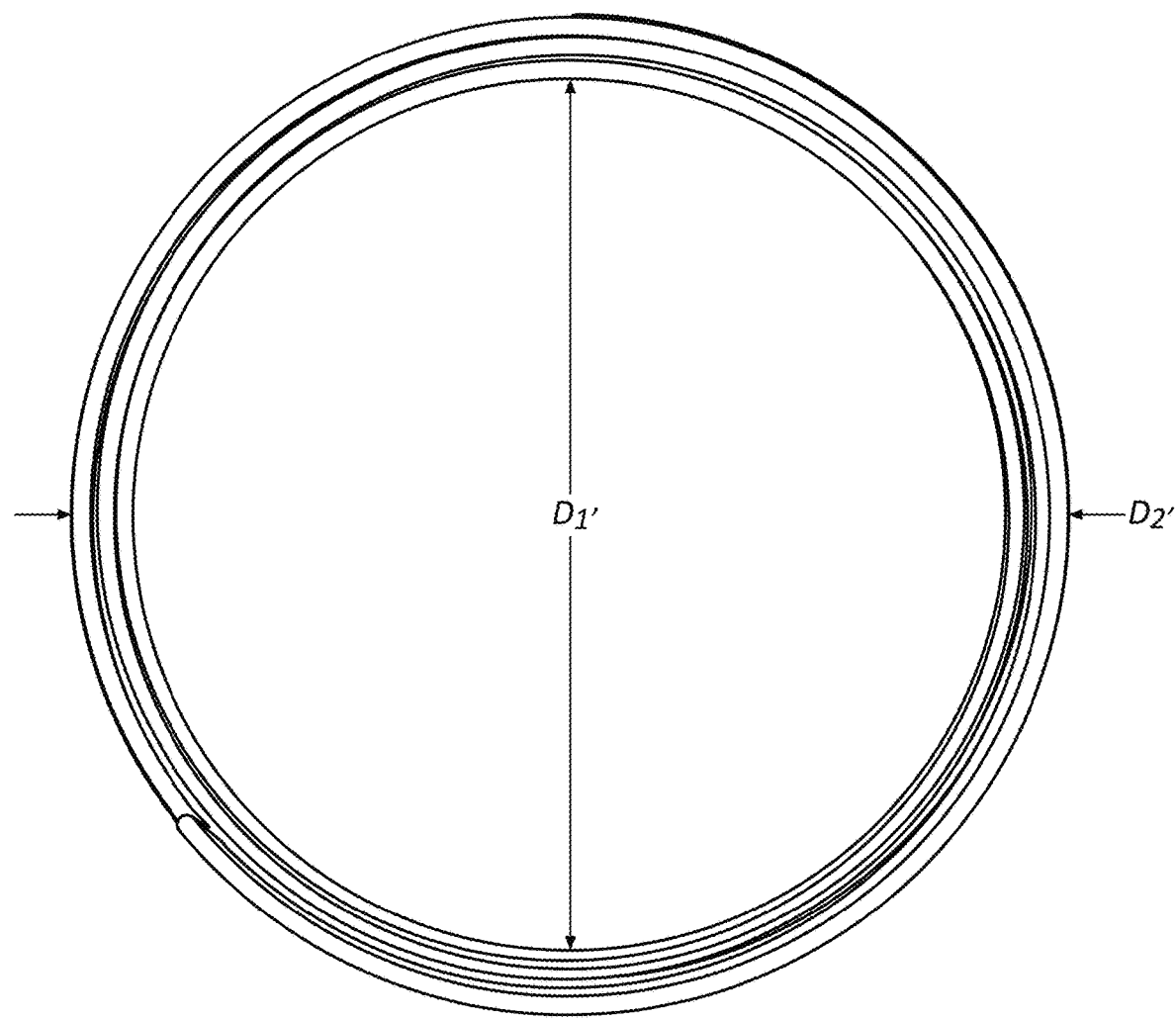
FIG. 8 is an end view of a frame having flared ends.
Figure 9:
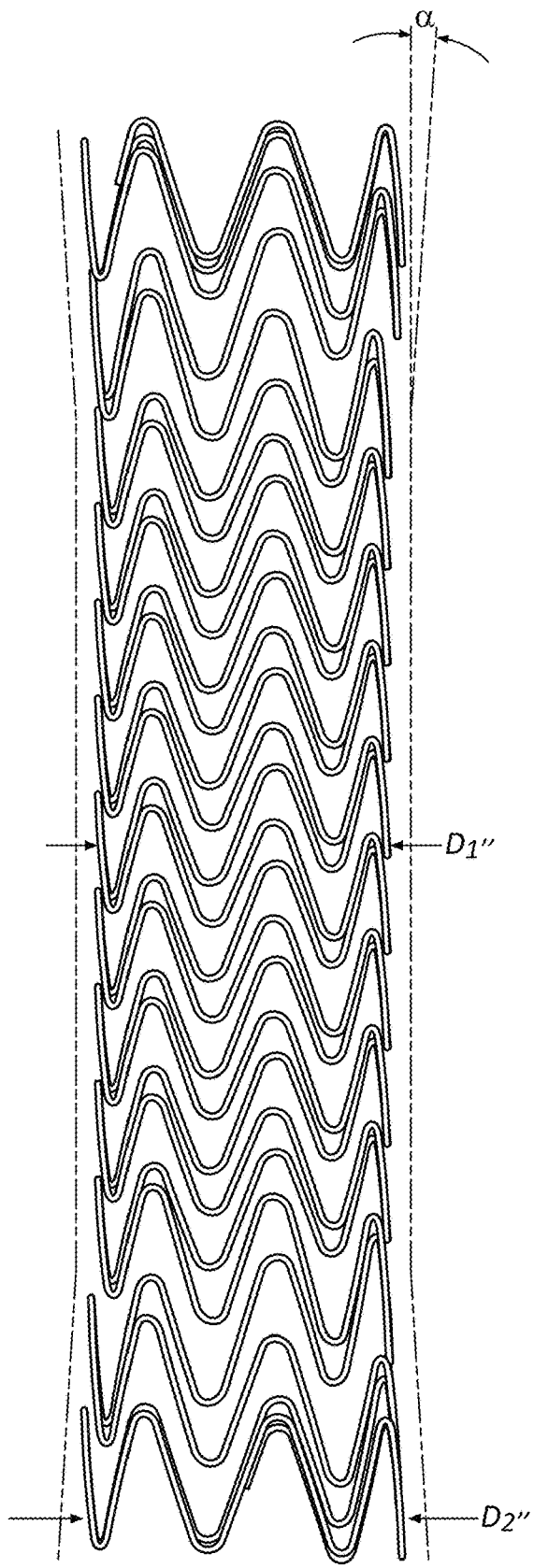
FIG. 9 is a front view of a frame having flared ends.
Figure 10:
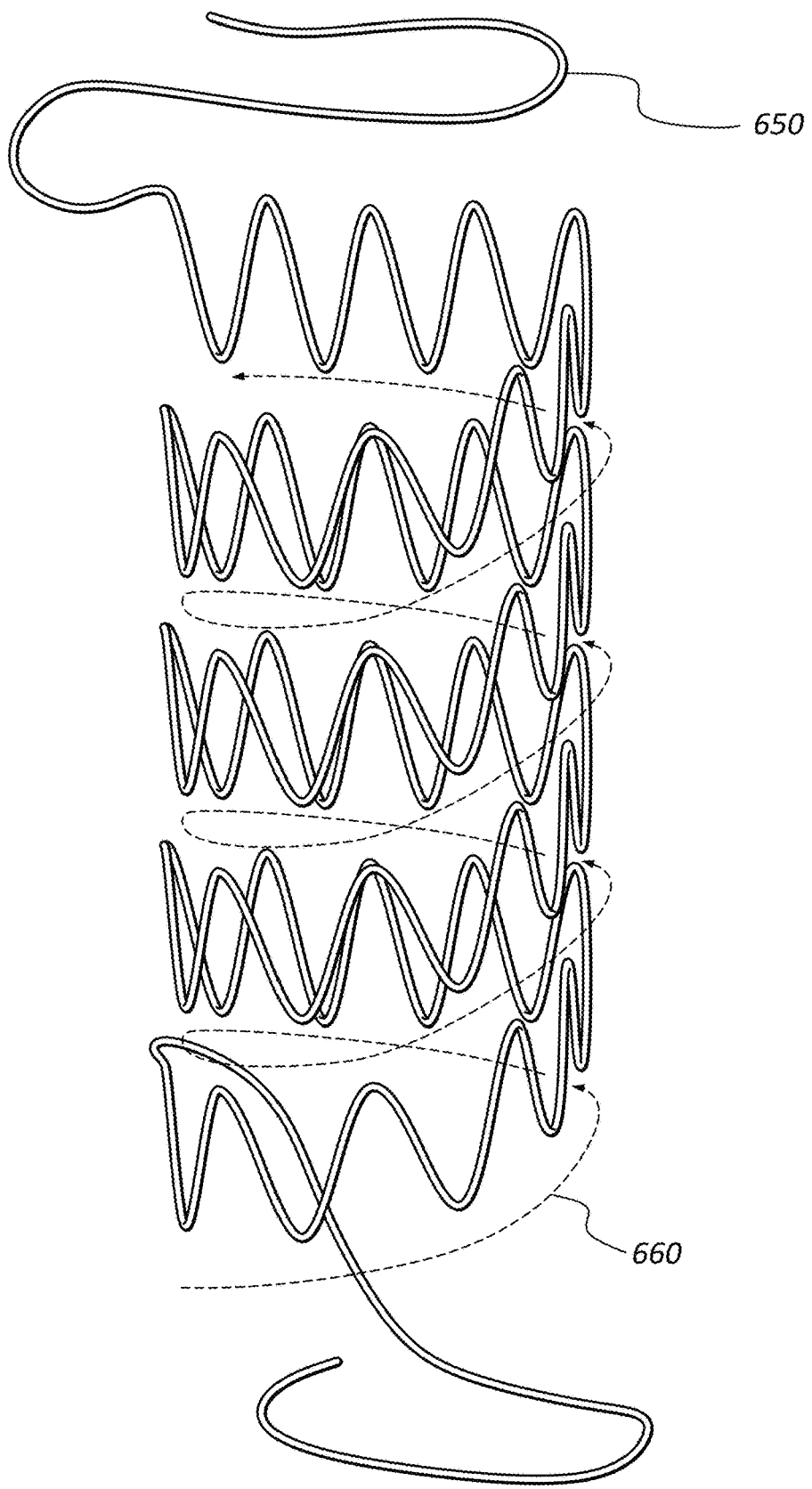
FIG. 10 is a front view of a wire being shaped to form a frame.

FIGS. 6, 7A, and 7B show views of a possible embodiment of a frame for use in connection with a medical appliance such as a stent or graft. FIG. 7C is an alternative configuration of a portion of the frame structure. FIGS. 8 and 9 are views of one embodiment of a frame that includes flared ends. FIG. 10 illustrates one embodiment of how a wire may be shaped to form a frame.

Frames for use in connection with medical appliances may be fabricated or formed into particular geometries through a variety of means. For example, a frame may be cut from a single tube of material, including embodiments wherein the frame is first laser cut, then expanded. In other embodiments, the frame may be molded, including embodiments wherein the frame is molded from a polymeric material. In still other embodiments, powder metallurgical processes, such as powdered compression molding or direct metal laser sintering, may be used.

FIG. 6 illustrates a front elevation view of an embodiment of a frame. The illustrated embodiment depicts one embodiment of a configuration for a metal wire 650 forming a frame. As depicted in FIG. 6, the frame may consist of a single continuous wire.

Referring generally to FIGS. 6, 7A, and 7B, particular features of the illustrated frame structure are indicated. It will be appreciated that the numerals and designations used in any figure apply to analogous features in other illustrated embodiments, whether or not the feature is so identified in each figure. As generally shown in these Figures, the frame structure may consist of a wire 650 shaped to form the frame. The wire 650 may be shaped in a wave-type configuration, the waves defining apexes 652 and arms 654 of the frame structure. The frame may further be coupled to a covering layer (not pictured). Additionally, in some embodiments, any covering as disclosed herein may be applied to any type of frame, for example, laser cut frames, polymeric frames, wire frames, and so forth.

The frame may be designed such that the midsection is "harder" than the ends. The "hardness" of the frame refers to the relative strength of the structure (e.g., its compressibility). A harder portion of the frame will have greater strength (i.e., exert a greater radial outward force) than a softer portion. In one embodiment, the midsection is harder than the proximal and distal end sections, which are relatively softer. Further, a frame may be configured to be flexible to facilitate the ability of the device to conform to the native anatomy at which the device is configured for use. Similarly, covered devices may be configured with covers that conform to the native anatomy at a therapy site.

Additionally, the frame may be configured to allow the entire device to be crimped into a relatively low-profile configuration for delivery. For example, devices of a certain diameter or constrained profile are more feasible for delivery at certain vascular or other access points than others. For example, in many instances a device configured for insertion via the radial artery may be relatively smaller than devices configured for insertion via the generally larger femoral artery. A frame may be configured to be crimped into a particular profile to enable potential access at various or desired access points. Similarly, devices having no frame may be configured to be disposed in a particular profile to facilitate access and delivery. Once a device is positioned within the body it may be expanded or deployed in a number of ways, including use of self-expanding materials and configurations. Additionally, some configurations may be designed for expansion by a secondary device, such as a balloon.

Four basic design parameters may be manipulated to influence the properties (hardness, strength, crush force, hoop force, flexibility, etc.) of the illustrated frame. These properties are (1) apex to apex distance, designated as $H_x$ in FIGS. 6 and 7A; (2) arm length, designated as $A_x$ in FIGS. 6 and 7A; (3) apex radius, designated as $R_x$ in FIG. 7A; and (4) the diameter of the wire 650. These values may or may not be constant at different points on a frame. Thus, the subscript "x" is used generically; that is, each distance identified as "H" refers to an apex to apex distance with subscripts 1, 2, 3, etc., signifying the apex to apex distance at a particular point. It will be appreciated that these subscript designations do not necessarily refer to a specific distance, but may be used relatively (i.e., $H_1$ may be designated as smaller than $H_2$ without assigning any precise value to either measurement). Further, as will be apparent to one skilled in the art having the benefit of this disclosure, an analogous pattern of measurements and subscripts is employed for other parameters described herein, for example $A_x$ and $R_x$.

The overall frame design may be configured to optimize desired radial force, crush profile, and strain profile. The frame design parameters may each be configured and tuned to create desired characteristics. For example, the strain profile may be configured to be less than the failure point for the material being used.

A first parameter, the apex to apex distance, is designated as $H_x$. This measurement signifies the distance between a first apex and a second apex where both apexes substantially lie along a line on the outside diameter of the frame that is co-planar with, and parallel to, the longitudinal axis of the frame. In some embodiments, $H_x$ may be constant along the entire length of the frame. In other embodiments the length of the frame may be divided into one or more "zones" where $H_x$ is constant within a zone, but each zone may have a different $H_x$. In still other embodiments $H_x$ may vary along the entire length of the frame. $H_x$ may be configured, in connection with the other design parameters, to determine the properties of the frame. Generally, regions of the frame with a smaller $H_x$ value will be harder than regions with a larger $H_x$ value.

In the embodiment illustrated in FIG. 6, there are two "flare zones" at either end of the frame and a midbody zone along the remaining length of the frame. In the illustrated embodiment, $H_1$ designates the apex to apex distance in the midbody zone of the frame and $H_2$ designates the apex to apex distance in the flare zones of the frame. In the illustrated embodiment, the apex to apex distance, $H_2$, is the same in both the flare zone near the distal end of the frame and the flare zone near the proximal end of the frame. In some embodiments $H_1$ may be smaller than $H_2$, resulting in a frame that is relatively harder in the midbody and relatively softer on the ends. A frame with such properties may be utilized in applications where strength is necessary along the midbody, for example to treat a tumor or other occlusion, but the ends are configured to rest on healthy tissue where softer ends will minimize trauma to the healthy tissue.

In embodiments where soft ends and a hard midbody are desirable, $H_1$ may be between about 2 mm and 30 mm, and $H_2$ between about 2.1 mm and 30.1 mm. For example, in frames configured for use in connection with stents for CV or PV applications, $H_1$ may be between about 3 mm and 10 mm, and $H_2$ between about 3.1 mm and 10.1 mm, such as 3 mm<$H_1$<8 mm and 3.5 mm<$H_2$<9 mm, 3 mm<$H_1$<6.5 mm and 4 mm<$H_2$<8 mm, or 3 mm<$H_1$<5 mm and 5.5 mm<$H_2$<6.5 mm.

In other embodiments where two or more apex to apex lengths are present in one frame, the change in apex to apex length may be correlated to the displacement of the apexes from the midpoint of the frame. In other words, the apex to apex length may increase incrementally as one moves away from the midpoint of the frame toward the ends in a manner that gives the frame the same geometry, and therefore the same properties, on either side of the midpoint of the length of the frame. In other embodiments, different geometries may be utilized at any point along the length of the frame. It will be appreciated that the ranges of values for $H_x$ disclosed above apply analogously to embodiments where the frame has multiple apex to apex lengths. For example, in one embodiment a frame may have an apex to apex length at midbody within one of the ranges disclosed above for $H_1$, and the value of $H_x$ may vary incrementally, in steps, or some other pattern, along the length of the frame, reaching an apex to apex length at the ends within the complementary range for $H_2$.

Moreover, in some embodiments, the value of $H_x$ may be small enough that adjacent coils are "nested" within each other. In other words, the apexes of a first helical coil may extend up into the spaces just below the apexes of the next adjacent coil. In other words, apexes of lower coils may extend a sufficient amount so as to be disposed between the arms of higher coils. In other embodiments the value of $H_x$ may be large enough that adjacent coils are completely separated. In embodiments wherein adjacent coils are "nested," the number of wires at any particular cross-section of the stent may be higher than a non-nested stent. In other words, cutting the frame along an imaginary plane disposed orthogonally to the longitudinal axis of the frame will intersect more wires if the frame is nested as compared to not nested. The smaller the value of $H_x$, the more the rows may be intersected by such a plane (that is, more than just the next adjacent row may extend into the spaces below the apexes of a particular row). Nested frames may create relatively higher strains in the frame when a stent comprised of the frame is loaded into a delivery catheter. In some instances the delivery catheter for a nested frame may therefore be relatively larger than a delivery catheter configured for a non-nested frame. Further, nested frames may be relatively stiff as compared to non-nested stents with similar parameters.

As will be apparent to those skilled in the art having the benefit of this disclosure, frames with a hard midbody and soft ends may be desirable for a variety of applications. Further, in some instances a basically "symmetric" frame may be desirable; in other words, a frame with certain properties at the midbody section and other properties at the ends, where the properties at both ends are substantially identical. Of course, other embodiments may have varied properties along the entire length of the frame. It will be appreciated that while the effect of changing variables, for instance the difference between $H_1$ and $H_2$, may be described in connection with a substantially symmetric stent (as in FIG. 6), the same principles may be utilized to control the properties of a frame where the geometry varies along the entire length of the frame. As will be appreciated by those skilled in the art having the benefit of this disclosure, this applies to each of the variable parameters described herein, for example $H_x$, $A_x$, and $R_x$.

A second parameter, arm length, is designated as $A_x$ in FIGS. 6 and 7A. As with $H_x$, $A_x$ may be constant along the length of the frame, be constant within zones, or vary along the length of the frame. Variations in the length of $A_x$ may be configured in conjunction with variations in the other parameters to create a frame with a particular set of properties. Generally, regions of the frame where $A_x$ is relatively shorter will be harder than regions where $A_x$ is longer.

In some embodiments, the arm length $A_1$ near the midsection of the frame will be shorter than the arm length $A_2$ near the ends. This configuration may result in the frame being relatively harder in the midsection. In embodiments where soft ends and a hard midbody are desirable, $A_1$ may be between about 2 mm and 30 mm, and $A_2$ between about 2.1 mm and 30.1 mm. For example, in frames for CV or PV applications, $A_1$ may be between about 2 mm and 10 mm, and $A_2$ between about 2.1 mm and 10.1 mm, such as 2.5 mm$<A_1<$8 mm and 3 mm$<A_2<$9 mm, 3 mm$<A_1<$6 mm and 4 mm$<A_2<$7.5 mm, or 4 mm$<A_1<$5 mm and 5 mm$<A_2<$6 mm.

In other embodiments where two or more arm lengths are present in one frame, the change in arm length may be correlated to the displacement of the arm from the midpoint along the frame. In other words, the arm length may increase incrementally as one moves away from the midpoint of the frame toward the ends in a manner that gives the frame the same geometry, and therefore the same properties, on either side of the midpoint of the length of the frame. In other embodiments, different geometries may be utilized at any point along the length of the frame. It will be appreciated that the ranges of values for $A_x$ disclosed above apply analogously to embodiments where the frame has multiple arm lengths. For example, in one embodiment a frame may have an arm length at midbody within one of the ranges disclosed above for $A_1$, and the value of $A_x$ may vary incrementally, in steps or some other pattern, along the length of the frame reaching an arm length at the ends within the complementary range for $A_2$.

A third parameter, the apex radius, is designated as $R_1$ in FIG. 7A. As with $H_x$ and $A_x$, $R_x$ may be configured in order to create desired properties in a frame. In some embodiments, the inside radius of each apex may form an arc that has a substantially constant radius. As shown by a dashed line in FIG. 7A, this arc can be extended to form a circle within the apex. The measurement $R_x$ refers to the radius of the arc and circle so described. Further, in some embodiments the arms and apexes of the frame are formed by molding a wire around pins protruding from a mandrel. The radius of the pin used gives the apex its shape and therefore has substantially the same radius as the apex. In some embodiments $R_x$ will be constant along the entire length of the frame, be constant within zones along the length of the frame, or vary along the entire length of the frame. Variations in the magnitude of $R_x$ may be configured in conjunction with variations in the other parameters to create a frame with a particular set of properties. Generally, regions of the frame where $R_x$ is relatively smaller will be harder than regions where $R_x$ is larger.

Furthermore, in some instances, smaller values of $R_x$ may result in relatively lower strain in the wire frame when the frame is compressed, for example when the frame is disposed within a delivery catheter. Moreover, wires of relatively larger diameters may result in relatively lower strain at or adjacent to the radius measured by $R_x$ when compressed, as compared to wires of smaller diameters. Thus, in some instances, the strain may be optimized for a particular design by varying the value of $R_x$ and the diameter of the wire forming the frame.

Like the other variables, $R_x$ may take on a range of values depending on the application and the desired properties of the frame. In some embodiments $R_x$ may be between about 0.12 mm and 1.5 mm, including from about 0.12 to about 0.64 mm. For example, in frames configured for use with stents for CV or PV applications, $R_x$ may be between about 0.35 mm and 0.70 mm, such as 0.35 mm$<R_x<$0.65 mm, 0.35 mm$<R_x<$0.6 mm, or 0.4 mm$<R_x<$0.5 mm.

It will be appreciated that the disclosed ranges for $R_x$ apply whether the value of $R_x$ is constant along the length of the frame, whether the frame is divided into zones with different $R_x$ values, or whether $R_x$ varies along the entire length of the frame.

The fourth parameter, wire diameter, is discussed in detail in connection with FIG. 10 below.

FIG. 7A illustrates a cutaway view of the front portions of two adjacent coils of a frame. The portions of the coils depicted are meant to be illustrative, providing a clear view of the three parameters $H_x$, $A_x$, and $R_x$. It will be appreciated that all three of these parameters may be configured in order to create a frame with particular properties. Any combination of the values, ranges, or relative magnitudes of these parameters disclosed herein may be used within the scope of this disclosure. As an example of these values taken together, in one embodiment of a CV or PV frame with a relatively hard midbody and softer ends, $H_1$ may be about 4 mm and $H_2$ about 5.9 mm, $A_1$ may be about 4.5 mm and $A_2$ about 5.6 mm, and $R_1$ about 0.5 mm.

FIG. 7B is a close-up view of one end of a frame. In embodiments where the frame is formed by a single continuous wire, FIG. 7B illustrates one way in which the end 656 of the wire may be coupled to the frame. As illustrated, the wire may be disposed such that the final coil approaches and runs substantially parallel to the previous coil. This configuration results in the apex to apex distance between the two coils decreasing near the end 656 of the wire. In some embodiments this transition will occur along the distance of about 4 to 8 apexes along the length of the wire. For example, if a frame is configured with an apex to apex spacing of $H_2'$ along the region of the frame nearest to the ends, the apex to apex distance will decrease from $H_2'$ to a smaller distance that allows the end 656 of the wire to meet the prior coil (as illustrated in FIG. 7B) over the course of about 4 to 8 apexes.

FIG. 7C illustrates an alternative configuration of a portion of a frame. In the embodiment of FIG. 7C, apexes 652' alternate in relative height along the length of the wire. In particular, in the embodiment shown, the apexes form a pattern comprising a higher apex, a shorter apex, a higher apex, a shorter apex, and so on, around the helical coil. In some instances, a frame may be configured with alternating apexes at one or both ends of the frame. For example, a frame as shown in FIG. 6 may be configured with the pattern of apexes 652' and arms 654' shown in FIG. 7C at one or both ends of the frame. Such an alternating pattern of apexes may distribute the force along the vessel wall at the ends of the frame, thus creating relatively a-traumatic ends.

The end 656 may be attached to the frame in a variety of ways known in the art. The end 656 may be laser welded to the frame or mechanically crimped to the frame. In embodiments where the frame is an element of a medical appliance further comprising a polymer cover, the end 656 may be secured by simply being bound to the cover. In other instances, a string may be used to bind or tie the end 656 to adjacent portions of the frame. Similarly, in some instances, a radiopaque marker may be crimped around the end 656 in such a manner as to couple the end 656 to the frame. Additionally, other methods known in the art may be utilized.

Furthermore, in some embodiments the frame may be configured with radiopaque markers at one or more points along the frame. Such markers may be crimped to the frame. In other embodiments a radiopaque ribbon, for example a gold ribbon, may be threaded or applied to the frame. In some embodiments these markers may be located at or adjacent to one or both ends of the frame. Any radiopaque material may be used, for example gold, bismuth, or tantalum. Radiopaque elements may be configured to facilitate the delivery and placement of a device and/or to facilitate viewing of the device under fluoroscopy.

Referring again to FIG. 6 as well as to FIGS. 8 and 9, the frame may be configured with flared ends. It will be appreciated that in certain embodiments a frame may have a flare at both the proximal and distal ends, only at the proximal end, only at the distal end, or at neither end. In certain of these embodiments the frame may have a substantially constant diameter in the midbody zone of the frame, with the ends flaring outward to a larger diameter. It will be appreciated that the geometry of the flares at the proximal and distal ends may or may not be the same.

In the embodiment illustrated in FIG. 6, the frame has a diameter, $D_1$, at the midbody of the frame. This diameter may be constant along the entire midbody of the frame. The illustrated embodiment has a second diameter, $D_2$, at the ends. This change in diameter creates a "flare zone" at the end of the frame, or an area in which the diameter is increasing and the frame therefore may be described as including a "flared" portion. In some embodiments the flare zone will be from about 1 mm to 60 mm in length. For example, in certain frames configured for use with stents designed for CV or PV applications, the flare zone may be from about 3 mm to about 25 mm in length, such as from about 4 mm to about 15 mm or from about 5 mm to about 10 mm in length.

The diameter of the stent at the midbody, the diameter at one or both flares, or all of these dimensions may be configured to be slightly larger than the body lumen in which the device is configured for use. Thus, the size of the device may cause interference with the lumen and reduce the likelihood the device will migrate within the lumen. Further, active anti-migration or fixation elements such as barbs or anchors may also be used.

FIGS. 8 and 9 also illustrate how a frame may be flared at the ends. Diameters $D_1'$ and $D_1''$ refer to midbody diameters, analogous to $D_1$, while $D_2'$ and $D_2''$ refer to end diameters analogous to $D_2$. Further, as illustrated in FIG. 9, the flared end may create an angle, alpha, between the surface of the frame at the midbody and the surface of the flare. In some instances the flare section will uniformly flare out at a constant angle, as illustrated in FIG. 9. In some embodiments angle alpha will be from about 1 degree to about 30 degrees. For example, in some frames configured for use with stents designed for CV or PV applications, alpha will be from about 2 degrees to about 8 degrees, such as from about 2.5 degrees to about 7 degrees or from about 3 degrees to about 5 degrees. In one exemplary embodiment, alpha may be about 3.6 degrees.

The frame of FIG. 6 also has a length L. It will be appreciated that this length can vary depending on the desired application of the frame. In embodiments where the frame has flare zones at the ends, longer frames may or may not have proportionally longer flare zones. In some embodiments, this flare zone may be any length described above, regardless of the overall length of the frame.

The disclosed frame may be formed in a variety of sizes. In some embodiments, L may be from about 10 mm to about 200 mm. For example, in CV applications the frame may have a length, L, of from about 40 mm to 100 mm or any value between, for example, at least about 50 mm, 60 mm, 70 mm, 80 mm, or 90 mm. In PV applications the frame may have a length, L, of from about 25 mm to 150 mm or any value between, for example, at least about 50 mm, 75 mm, 100 mm, or 125 mm. The frame may also be longer or shorter than these exemplary values in other applications.

Likewise the frame may be formed with a variety of diameters. In some embodiments the midbody diameter of the frame may be from about 1 mm to about 45 mm, including from about 4 mm to about 40 mm. For example, in CV or PV applications the frame may have a midbody inside diameter of about 3 mm to 16 mm, or any distance within this range such as between about 5 mm and about 14 mm or between about 7 mm and about 10 mm. Moreover, in some instances, the diameter, or a diameter-like measurement of the frame, may be described as a function of other components. For example, the frame may be configured with a particular number of apexes around a circumference of the frame. For example, some frames may be configured with between about 2 and about 30 apexes around a circumference of the frame.

The frame may or may not be configured with flared ends regardless of the midbody diameter employed. In some CV embodiments the maximum diameter at the flared end will be between about 0.5 mm and about 2.5 mm greater than the midbody diameter. For example, the maximum diameter at the flared end may be between about 1 mm and about 2 mm, or alternatively between about 1.25 mm and about 1.5 mm, such as about 1.25 mm or about 1.5 mm greater than the midbody diameter.

Referring now to FIG. 10, the frame may be formed from a single continuous wire. In some embodiments the wire may be comprised of Nitinol (ASTM F2063) or other suitable materials. In some embodiments the wire will have a diameter between about 0.001 inch and about 0.05 inch, including from about 0.005 inch and about 0.025 inch. For example, in some frames designed for CV or PV applications, the wire diameter may be from about 0.008 inch to about 0.012 inch in diameter including certain embodiments where the wire is from about 0.009 inch to about 0.011 inch in diameter or embodiments where the wire is about 0.010 inch in diameter. Furthermore, frames configured for the thoracic aorta may be formed of wires up to 0.020 inch in diameter, including wires between about 0.010 inch and 0.018 inch in diameter.

FIG. 10 illustrates how, in some embodiments, the wire 650 may be wound in a helical pattern creating coils that incline along the length of the stent. The waves of the wire that form the arms and apexes may be centered around this helix, represented by the dashed line 660.

In some embodiments, a stent, graft, or other tubular device may comprise a tapered segment along the length of the device. A taper may be configured to reduce the velocity of fluid flow within the device as the fluid transitions from a smaller diameter portion of the device to a larger diameter portion of the device. Reducing the fluid velocity may be configured to promote laminar flow, including instances wherein a tubular member is tapered to promote laminar flow at the downstream end of the device.

Figure 11A:
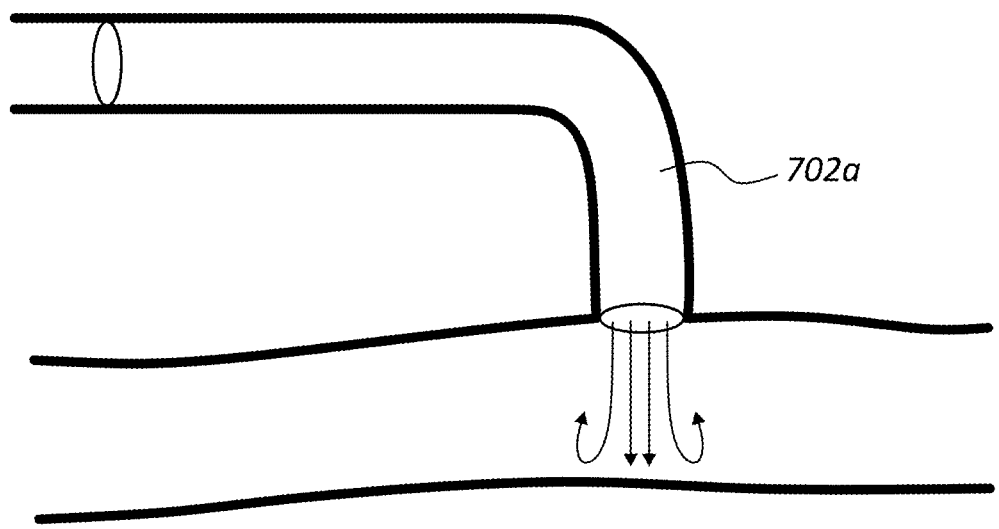
FIG. 11A is a cross-sectional view of two body lumens with a stent disposed therein.

Further, in some embodiments, a stent or other tubular member may be positioned at a junction between two or more body lumens. For example, FIG. 11A illustrates a stent 702a disposed at an intersection between two body lumens. In some embodiments, stent 702a may be configured to promote laminar flow at the intersection of the lumens.

Figure 11B:
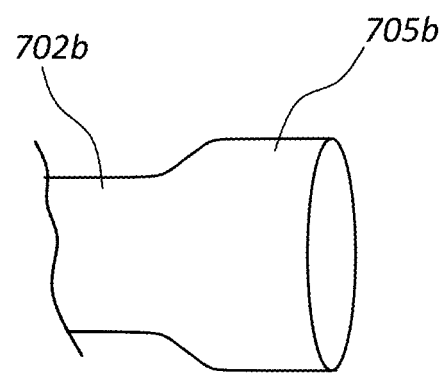
FIG. 11B is a side view of a portion of a stent comprising a tapered segment.
Figure 11C:
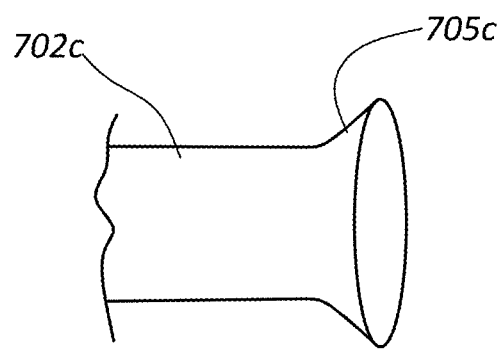
FIG. 11C is a side view of another embodiment of a stent comprising a tapered segment.

FIG. 11B illustrates a portion of a stent 702b having a tapered segment 705b which may be configured to reduce flow velocity within the stent 702b. In some embodiments, such as that of FIG. 11B, the tapered segment 705b may be positioned upstream of the downstream end of the stent 702b. FIG. 11C illustrates another exemplary embodiment of a portion of a stent 702c having a tapered segment 705c adjacent the downstream end of the stent 702c. Either tapered segment (705b, 705c) may be used in connection with any stent, including embodiments wherein the tapered segment is configured to promote laminar flow in and around the stent. For example, the stent 702a of FIG. 11A may be configured with either tapered portion (705b, 705c) to promote laminar flow out of the stent 702a and at the junction between the body lumens of FIG. 11A.

Use of electrospun coatings may facilitate application of a covering of uniform thickness along a tapered stent. For example, in some embodiments, electrospun coatings may be configured to evenly coat devices comprised of various geometries. An electrospun coating may deposit a substantially even coating along various geometries such as tapers, shoulders, and so forth.

Additionally, various additional processing steps, methods, procedures, and systems for serially deposited fiber mats, such as electrospun or rotational spun mats, are within the scope of this disclosure. Materials comprising serially deposited fiber mats which have been processed by any of the methods or systems described below are likewise within the scope of this disclosure. These processes and materials may be used to create multilayered constructs having one or more layers of serially deposited fiber material which has been post processed as described below and/or having one or more layers of serially deposited fiber material which has not been post processed. The post processing methods and related materials described below describe various methods of modifying the material properties of serially deposited fiber layers to, for example, change the strength of the material, change the surface characteristics of the material, change the porosity of the material, set the material in a particular geometry or shape, and so forth.

Serially deposited fiber mats may comprise a membrane in the form of a sheet, a sphere, a strip, or any other geometry. As used herein, the term "membrane" refers to any structure comprising serially deposited fibers having a thickness which is smaller than at least one other dimension of the membrane. Examples of membranes include, but are not limited to, serially deposited fiber mats or lattices forming sheets, strips, tubes, spheres, covers, layers, and so forth. Additionally, any material which can be serially deposited as fibers may be processed as described below.

Further, as used herein, references to heating a material "at" a particular temperature indicate that the material has been disposed within an environment which is at the target temperature. For example, placement of a material sample in an oven, the interior of the oven being set at a particular temperature, would constitute heating the material at that particular temperature. While disposed in a heated environment, the material may, but does not necessarily, reach the temperature of the environment. The term "about," as used herein in connection with temperature, is meant to indicate a range of ±5 degrees C. around the given value. The term "about" used in connection with quantities or values indicates a range of ±5% around the value.

Serially deposited membranes may be processed to alter the strength or other characteristics of the material by stretching the membrane in one or more directions. In some embodiments the membrane may initially be sintered after it is serially deposited. The membrane may then be heated at a particular temperature prior to further processing of the membrane. As further outlined below, heating and stretching a membrane of serially deposited fibers may tend to cause increased strength in the direction the membrane is stretched. In some embodiments, the material may also exhibit increased fiber alignment in the direction of stretching.

Temperatures at which materials may be heated prior to processing may vary depending on the material and depending on the desired characteristics of the material after processing. For example, a polymeric membrane may show more or less fiber alignment after processing depending on various factors, such as the temperature at which the materials are heated. In some instances a membrane may be heated at a temperature at or above the crystalline melt point of the material comprising the membrane, though it is not necessary to heat the material as high as the crystalline melt temperature to stretch process the material.

In the case of polymeric materials which are sintered, the step of heating the membrane may be performed as a separate and distinct step from sintering the membrane, or may be done as the same step. For example, it is within the scope of this disclosure to process a membrane directly after sintering the membrane, while the membrane is at an elevated temperature due to the sintering process. It is likewise within the scope of this disclosure to obtain a previously sintered membrane which may have been previously cooled to ambient or room temperature, then heat the membrane as part of a heating and stretching process.

Membranes or any other mat or lattice of serially deposited fibers may be stretched in any direction as part of a heating and stretching process. For example, a tubular membrane may be stretched in the axial/longitudinal direction, the radial direction, or any other direction. Further, it is within the scope of this disclosure to stretch a membrane in multiple directions, either simultaneously or as part of separate steps. For example, a tubular membrane may be stretched both axially and radially after the membrane is initially heated, or the membrane may be stretched in these or other directions as part of distinct and separate steps. Additionally, the membrane may be heated multiple times during such a process.

Various methods, modes, mechanisms, and processes may be utilized to apply forces to stretch materials. For example, force may be applied through mechanical, fluidic, electromagnetic, gravitational, and/or other mechanism or modes. In embodiments wherein force is applied through fluidic interaction, a pressurized gas or liquid could be used to generate the force while the material is at an elevated temperature. The fluid may be stagnant or recirculating. Further, the fluid may be used to heat and/or cool the material. For example, the liquid may be used to rapidly cool the material, locking the microstructure and geometry.

A heated and stretched membrane may be held in a stretched position while the membrane cools. For example, a membrane may be heated at an elevated temperature prior to stretching, stretched while the membrane is at an elevated temperature, then held in the stretched position while the membrane cools to an ambient temperature, such as room temperature. Depending on the process, when the membrane is stretched, it may be at a temperature lower than the temperature at which it was heated, and it may or may not cool completely to the ambient temperature while the position is held.

Processing a mat or lattice of serially deposited fibers as by heating and stretching may alter various material properties of the mat or lattice. For example, and as further outlined below, heating and stretching a fiber mat may increase the durability of the material, increase the smoothness of the material, increase handling characteristics, increase the tensile strength of the material, increase resistance to creep, or otherwise alter the material. Further, in some embodiments, heating and stretching the material tends to align a portion of the fibers which comprise the mat in the direction the material is stretched. This alignment of the microstructure and/or nanostructure of the material may impact microscale and/or nanoscale interactions between the mat and other structures, such as body cells. Fiber alignment may likewise alter the flow characteristics of a fluid flowing in contact with the mat. For example, a tubular membrane configured to accommodate blood flow may exhibit different flow conditions through the tube if the fibers are aligned by heating and stretching as compared to randomly disposed fibers.

Additionally, heating and stretching a mat may or may not tend to align the fibers in the direction the material is stretched. In some embodiments, the degree of fiber alignment may be related to the temperature at which the mat was heated prior to stretching. Further, stretching a mat in multiple directions may tend to maintain random fiber disposition of a mat in embodiments wherein the original mat exhibited generally random fiber disposition.

Regardless of whether heating and stretching tend to align the fibers in the direction the mat was stretched, the mat may exhibit different properties in a stretched direction as compared to a non-stretched direction. For example, the mat may exhibit increased tensile strength and/or increased resistance to creep in the stretched direction while these properties may be generally unchanged or decreased in a non-stretched direction. Further, stretching may increase the porosity of a mat of serially deposited fibers. In some embodiments, stretching may increase the porosity of a mat by up to 10 times the original porosity, including up to eight times, up to six times, up to four times, and up to two times the original porosity. In some embodiments, a mat may be stretched while at room temperature to increase porosity, to increase strength, or to modify other properties of the mat.

Additionally, in some embodiments, a tubular membrane heated and stretched in the axial direction may exhibit greater tensile strength in the axial direction as compared to the properties of the membrane prior to heating and stretching. In this example, the tensile strength in the radial direction, however, may be similar to the tensile strength of the membrane in that direction prior to heating and stretching. Thus, the membrane may have similar properties in both these directions prior to heating and stretching, but may exhibit greater tensile strength in the axial direction after heating and stretching. In some embodiments, the tensile strength of the membrane is 150%-300% that of the membrane prior to heating and stretching in the direction of stretching. For example, the tensile strength of the membrane is at least 150%, at least 200%, at least 250% or at least 300% that of the membrane prior to heating and stretching in the direction of stretching. In some embodiments, a mat may exhibit decreased tensile strength or other changes in properties in a non-stretched direction disposed perpendicular to the direction of stretching, as compared to those properties prior to stretching.

In some embodiments, a material is stretched in multiple directions to increase strength or otherwise alter the properties in those directions. In other embodiments, heating and stretching change the properties in only one direction. For example, a tube may be configured to be bolstered against creep in the radial direction, without substantially affecting the material properties in the axial direction. Again, in some instances an increase in particular properties in a first direction is correlated with a decrease in one or more of the same properties in a second direction.

Additionally, materials having different properties in different directions may be combined to create a composite construct. For example, a composite construct comprising at least one layer of axially stretched material and at least one layer of radially stretched material may exhibit increased strength in both directions. Various layers having various properties may be combined to tailor the properties of the resultant construct. It is within the scope of this disclosure to bond adjacent layers through various processes, including use of tie layers disposed between layers and bonded to each layer, heating adjacent layers to create fiber entanglement, use of adhesives, and so forth. FEP may be used as a tie layer in some embodiments. Further, ePTFE may be used as a tie layer in some embodiments. One embodiment of a composite tube can be created by helically or cigar wrapping a tube of serially deposited fibers (un-stretched) with a film of heat and stretch processed material, creating a porous luminal layer and a strong creep resistant reinforcement layer. Additionally, layers (such as an impervious layer and/or a porous abluminal layer) may be added to the construct as well. Each layer may be configured to optimize a physiologic interaction, for example.

Multilayered constructs may further comprise reinforcing structures, such as metal scaffolds or frames. In some embodiments, a reinforcing structure may comprise one of: Nitinol, stainless steel, or titanium. Any layer of a construct may be configured to be a blood contacting layer. Blood contacting layers may be configured to interact with the blood or other biological elements and may be configured with certain flow characteristics at the blood interface. Further, any layer of a multilayered construct may be configured to be impermeable to tissue or fluid migration. For example an impermeable tie layer may be disposed between porous inner and outer layers of a construct.

Single layer devices or multilayered constructs within the scope of this disclosure may comprise tubes, grafts, stents, stent grafts, vascular grafts, patches, prosthetics, or any other medical appliance. Medical appliances configured for oral surgery and/or plastic surgery are also within the scope of this disclosure.

Again, heat and stretch processing may increase strength in the stretched direction while decreasing strength in a direction perpendicular to the stretched direction. For example, a tubular membrane stretched in the axial direction may exhibit greater strength in the axial as opposed to the radial direction. Further, a membrane so processed may exhibit greater elasticity or "spring" in the non-stretched direction oriented perpendicular to the stretched direction.

Heating and stretching a mat or lattice of serially deposited fibers may tend to decrease the thickness of the mat or lattice. For example, a tubular mat stretched in the range from 200% to 450% may exhibit a decrease in material thickness of between 10% and 90%, including from 20% to 80% and from 40% to 60%. Embodiments within these ranges may not exhibit holes or defects from the stretching process, and the overall surface quality of the material may be maintained after stretching. Further, these ranges are intended to correlate the degree of stretching and the decrease in material thickness, not to constitute upper or lower bounds. Materials may be stretched further than the given range to further decrease the material thickness, for instance.

As stated above, it is within the scope of this disclosure to heat and stretch various serially deposited fiber mats comprising various materials. Many of the examples discussed below refer particularly to PTFE fiber mats which have been processed in a variety of ways. These examples, or any other example referencing PTFE, may analogously apply to other materials as well. Specific temperatures for heating or otherwise processing a material may be analogously applied to other materials by considering the material properties (such as melting point) of such materials and analogizing to the examples below.

Generally, serially deposited PTFE fiber mats may be heated at temperatures between about 65 degrees C. and about 400 degrees C. while heating and stretching the mats. For example, serially deposited PTFE fiber mats may be heated at temperatures above about 65 degrees C., above about 100 degrees C., above about 150 degrees C., above about 200 degrees C., above about 250 degrees C., above about 300 degrees C., above about 350 degrees C., above about 370 degrees C., and above about 385 degrees C. Additionally, serially deposited PTFE fiber mats may be stretched at room temperature (22 degrees C.) without heating.

Serially deposited PTFE mats may be stretched from 150% to 500% of the initial length of the mat in the direction of stretching, including stretching mats to between 200% and 350%, between 250% and 300%, and between 300% and 500% of the original length of the mats in the direction of stretching. The amount of length change may be related to the temperature at which the mat is heated, the force applied when the mat is stretched, the original thickness of the mat, and the rate at which the mat is stretched.

Processing serially deposited fiber mats or lattices through heating and stretching may impact various properties of the mats. Tensile strength, resistance to creep, elasticity, and so forth may all be impacted. In some embodiments, processed mats are used as layers of multilayered constructs to provide particular properties in a particular direction.

The temperature at which mats of serially deposited PTFE fibers are heated may affect the tendency of the fibers of the mats to align after the mats are stretched. Higher temperatures generally correlate with increased fiber alignment. Generally, PTFE mats heated at or above 370 degrees C. exhibit more fiber alignment than mats heated at temperatures lower than 370 degrees C. Additionally, an increase in tensile strength is correlated with heating and stretching PTFE, whether or not the mat was heated at 370 degrees C. or more. The amount of the increase in tensile strength may be affected by the temperature at which the mat was heated and the amount the material was stretched.

Serially deposited fibers may be set in various geometries by constraining the fibers in a particular geometry and heating the fibers. For example, in some embodiments, constraining a previously sintered (or otherwise structurally set) mat or lattice of serially deposited fibers in a particular configuration, softening the material of the mat or lattice (for example by heating), and allowing the material to reset may result in a "memory" effect wherein the material retains at least a portion of the constrained geometry. Materials may be shape-set as described herein whether or not the materials have been heated and stretched as described above.

In embodiments comprising serially deposited polymeric fibers, heating the material at about the crystalline melt point of the material may facilitate setting of the geometry.

In one exemplary embodiment, a tubular membrane may be serially deposited on a mandrel, sintered, and removed from the mandrel. Though this specific example includes a tubular membrane, the present disclosure also applies to sheets, spheres, and other geometries of serially deposited fiber mats. The tubular membrane of sintered serially disposed polymeric fibers may then be constrained in a variety of configurations. For example, the membrane may be compressed onto a mandrel such that the tubular membrane is compressed along a shorter length, tending to create annular ridges or corrugations along the length of the membrane.

Once the membrane is constrained into the desired shape, the membrane may be heated while constrained. After heating and cooling, the membrane may tend to retain the constrained shape. A tubular membrane set in a corrugated shape may exhibit elasticity between the ends of the membrane due to the corrugation. When pulled in the axial direction (opposite the direction the membrane was compressed prior to heat-setting) then released, the membrane will tend to return to the heat-set corrugated configuration.

Furthermore, in the case of a corrugated tubular membrane, corrugations may facilitate bending of the membrane. Specifically, the annular corrugations may both reinforce the membrane and provide elasticity such that the membrane can bend in a variety of configurations without kinking.

Multilayered constructs comprising corrugated or otherwise heat-set components are within the scope of this disclosure. For example, a tubular graft may comprise a corrugated tube coupled to a second tube having a relatively smooth wall (with respect to the corrugated tube). The tubes may overlap and be coaxial. In some embodiments a construct will be configured with a smooth wall tube defining an inside diameter (which may be a blood contacting surface) and a corrugated tube defining an outside diameter (to provide support to the construct). As used herein, a smooth wall component refers to a component without visually apparent surface defects or irregularities.

EXAMPLES

Figure 15:
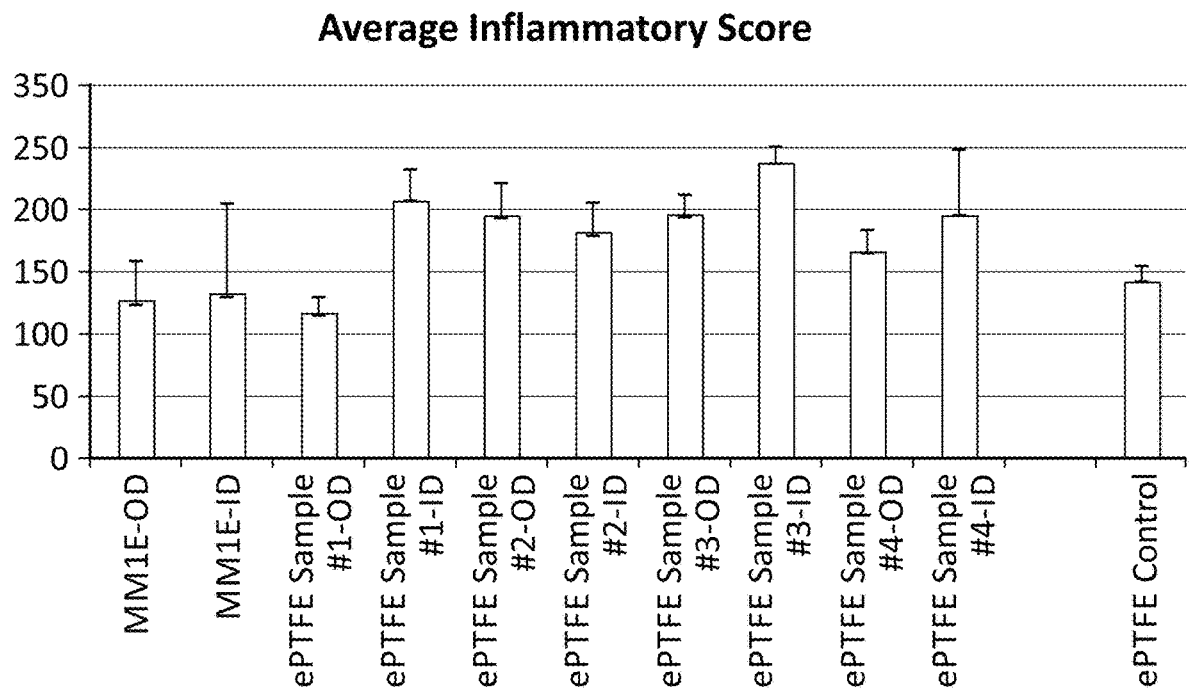
FIG. 15 is a graph showing average inflammatory score (H-Score=0-300) of various PTFE materials following 2 weeks of subcutaneous implantation in a mouse model.
Figure 16:
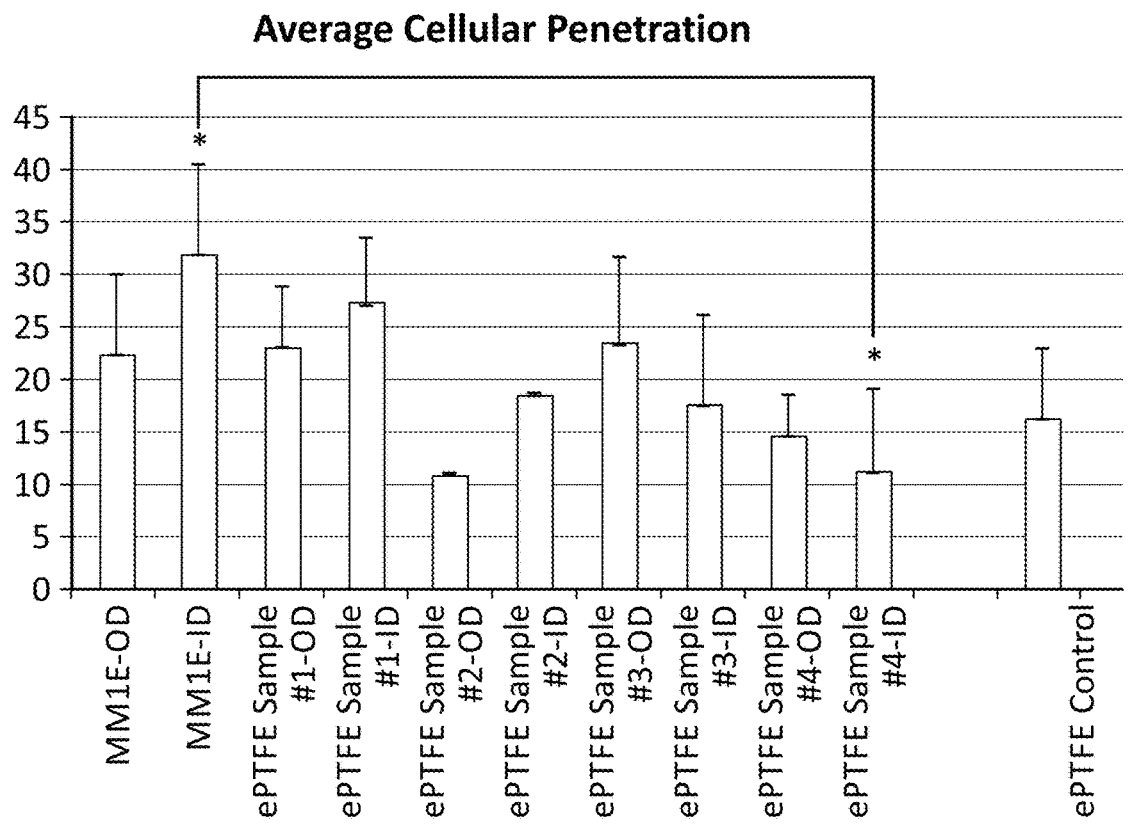
FIG. 16 is a graphical representation of the differences in cellular penetration between electrospun PTFE and expanded PTFE (ePTFE) materials. Percent of cellular penetration is shown on the y-axis.
Figure 17:
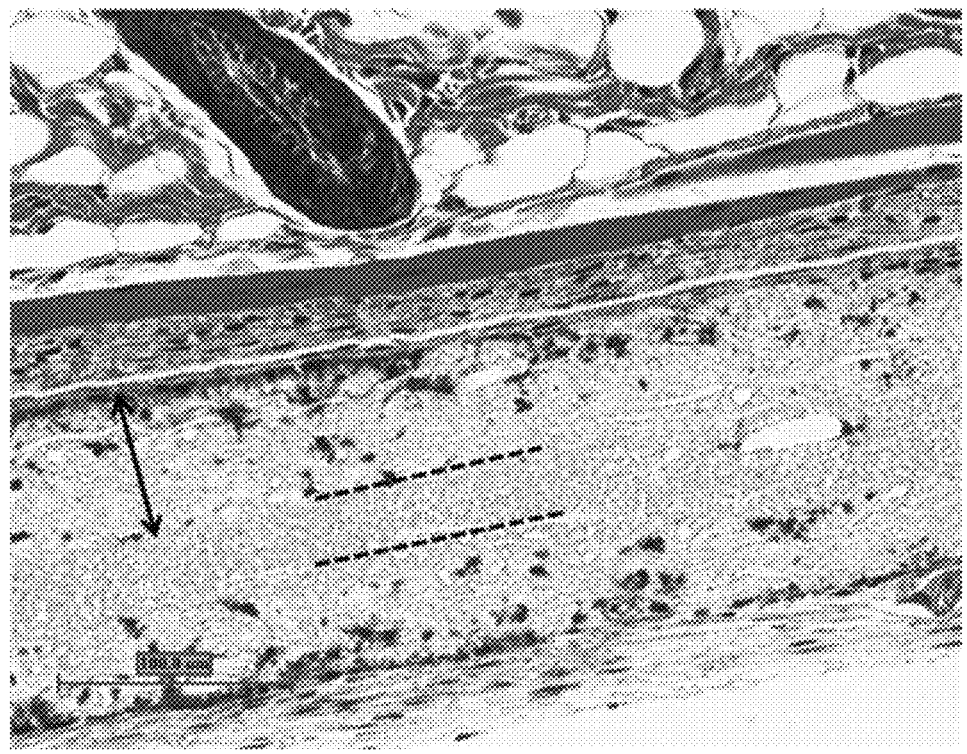
FIG. 17 is a representative trichrome-stained histology light microscopy image of electrospun PTFE material (MM1 E-OD). Relative distance of cell penetration is marked by the double black arrow. The dashed lines circumscribe the middle layer of the electrospun PTFE material. (Scale bar=100 um.)

A number of exemplary PTFE mats were produced according to the electrospinning disclosure above. FIGS. 12A-14B are SEMs of the PTFE mats produced in each exemplary process. FIGS. 15-16 are graphs comparing materials electrospun according to the present disclosure with other materials. Finally, FIG. 17 is a trichrome-stained histology light microscopy image of an electrospun PTFE material. The following examples are intended to further illustrate exemplary embodiments and are not intended to limit the scope of the disclosure.

Example 1

An experimental apparatus was assembled inside a ventilated hood. The experimental apparatus comprised a KD Scientific motorized syringe pump, a 10 ml syringe fitted with a 25 gauge metal syringe tip, and a Spellman CZE 1000R high voltage source. The positive lead of the high voltage source was connected to the metal syringe tip. The negative lead of the high voltage source was connected to a metal collector mounted about 7 inches from the syringe tip.

Polymer solution was prepared by obtaining a 60 wt % PTFE aqueous dispersion. Crystalline PEO with an average chain molecular weight of approximately 300,000 was used. The PEO was mixed with water in an approximately 30 wt % concentration and mixed until substantially homogeneous. The 60 wt % PTFE dispersion was added to the PEO/water mixture to create five concentrations: a 0.016 g/ml mixture of PEO to PTFE dispersion, a 0.02 g/ml mixture of PEO to PTFE dispersion, a 0.032 g/ml mixture of PEO to PTFE dispersion, a 0.04 g/ml mixture of PEO to PTFE dispersion, and a 0.048 g/ml mixture of PEO to PTFE dispersion. (Additionally, 35 ml of a 0.05 g/ml mixture of PEO to PTFE dispersion was obtained by adding 5 ml of water to 1.4 grams of PEO which was then mixed with 30 ml of PTFE dispersion. This concentration was not directly tested.) The PTFE/PEO/water combination was then mixed until substantially homogeneous. The resulting mixture was strained through a 70 micrometer nylon cell strainer to remove any remaining clumps in the mixture.

Each polymer solution was separately loaded into the syringe, and the syringe pump configured to dispense 0.01 ml of solution per minute. The syringe pump was activated and the high voltage power source turned on at 15,000 kV. The solution was forced through the syringe tip, where it was electrically charged and pulled in a small diameter fiber toward the collector. The process was run for approximately 15 minutes for each polymer solution, and the collector removed and sintered after running each solution. The collector and thin mat of fibers was sintered in an oven at 385 degrees C. for about 10 minutes. The resulting mat was removed and the collector used for the next solution. Each sintered mat was analyzed using a JEOL JSM-6510LV Scanning Electron Micrograph.

Figure 12A:
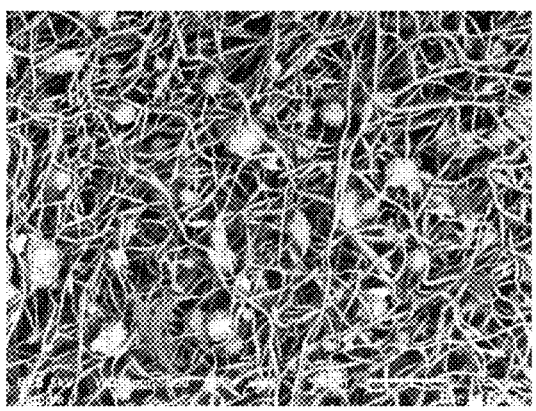
FIG. 12A is an SEM (scanning electron micrograph) (950×) of a mat electrospun from a first polymer dispersion.
Figure 12B:
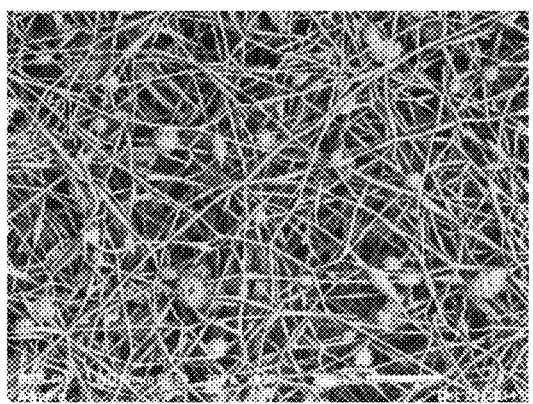
FIG. 12B is an SEM (950×) of a mat electrospun from a second polymer dispersion.
Figure 12C:
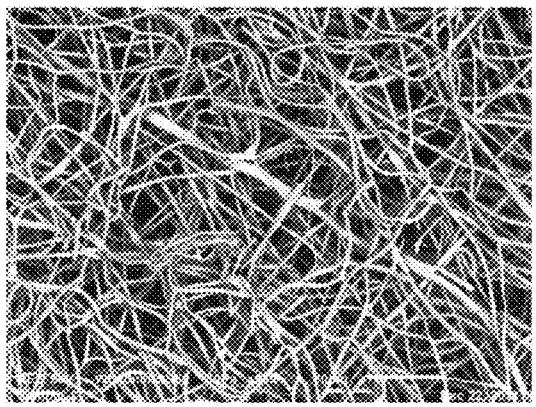
FIG. 12C is an SEM (950×) of a mat electrospun from a third polymer dispersion.
Figure 12D:
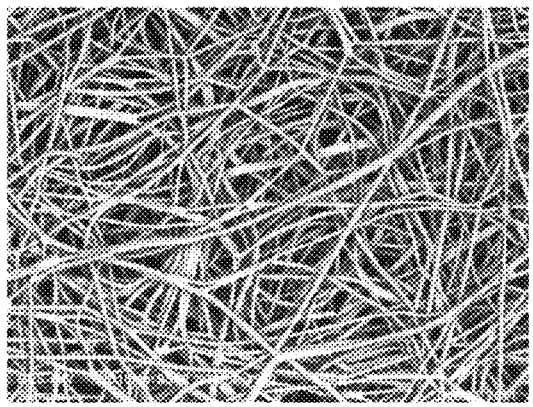
FIG. 12D is an SEM (950×) of a mat electrospun from a fourth polymer dispersion.
Figure 12E:
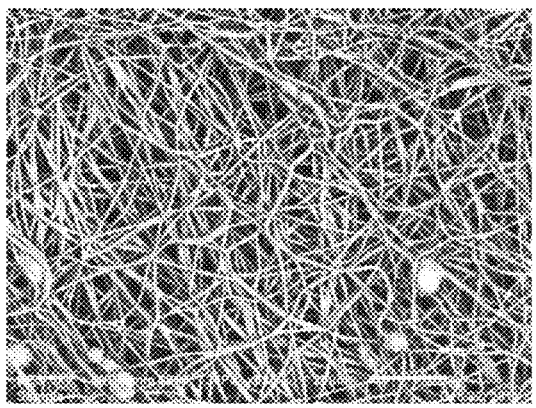
FIG. 12E is an SEM (950×) of a mat electrospun from a fifth polymer dispersion.

FIGS. 12A-12E are SEMs of the five fiber mats corresponding to the five polymer solutions spun in this example. Each SEM is at 950× magnification. FIG. 12A corresponds to the 0.016 g/ml mixture, FIG. 12B to the 0.02 g/ml mixture, FIG. 12C to the 0.032 g/ml mixture, FIG. 12D to the 0.04 g/ml mixture, and FIG. 12E to the 0.048 g/ml mixture.

It was observed that, in this example, the concentration of PEO to PTFE dispersion appeared to affect fiber formation on the mat. Both fiber diameter and the presence of "beads" within the fibers appeared affected by the concentration. Solutions with low concentrations (less than about 0.02 g/ml) produced beading that may have been due to "sputtering" as the solution left the syringe. Again, the resultant fiber mats are shown in FIGS. 12A-12E. Additionally, it was observed that solutions with less than about 0.015 g of PEO per ml of PTFE dispersion did not tend to form fibers, and solutions with greater than 0.06 g/ml concentrations tended to dry in the syringe prior to electrospinning, creating macroscopic defects in the mats.

In some embodiments, a construction comprised at least partially of beaded fibers may be incorporated into a stent covering or graft. For example, beaded fibers may increase endothelial attachment in some instances. Thus, electrospun PTFE beaded fibers, such as those shown in FIGS. 12A and 12B, may be utilized in some constructions. As discussed above, beading may occur with mixtures from about 0.010 g/ml to about 0.018 g/ml of PEO per ml of PTFE.

Example 2

Figure 13A:
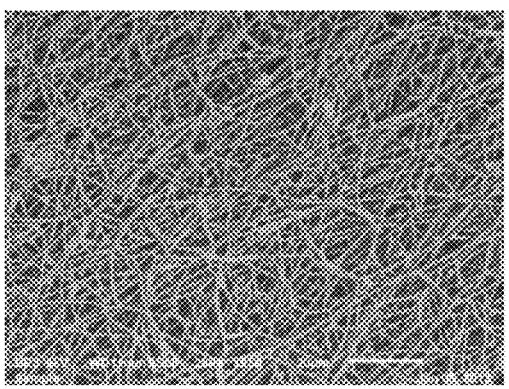
FIG. 13A is an SEM (950×) of a mat electrospun from a first polymer dispersion-water mixture.
Figure 13B:
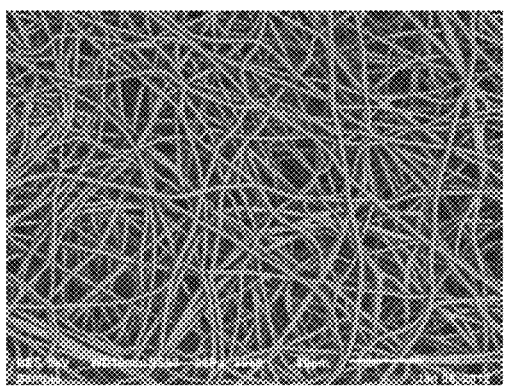
FIG. 13B is an SEM (950×) of a mat electrospun from a second polymer dispersion-water mixture.

The apparatus described in Example 1 was again utilized to electrospin eight additional solutions in connection with this Example. Substantially the same procedures described above were followed. However, additional water was added to the PEO-water mixture prior to mixing with the PTFE dispersions. The additional water appeared to facilitate electrospinning of a greater range of PEO to PTFE dispersion concentrations, while minimizing beading and sputtering. FIGS. 13A-13H are SEMs corresponding to eight different concentrations with additional water added. Each SEM is at 950× magnification. FIG. 13A corresponds to a concentration of 0.0256 g/ml of PEO to PTFE dispersion, FIG. 13B to a concentration of 0.030 g/ml, FIG. 13C to a concentration of 0.035 g/ml, FIG. 13D to a concentration of 0.040 g/ml, FIG. 13E to a concentration of 0.045 g/ml, FIG. 13F to a concentration of 0.050 g/ml, FIG. 13G to a concentration of 0.060 g/ml, and FIG. 13H to a concentration of 0.070 g/ml.

Figure 13C:
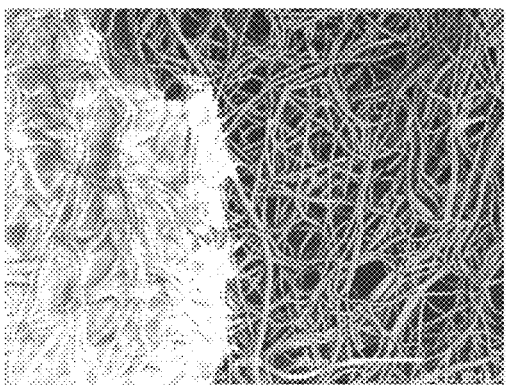
FIG. 13C is an SEM (950×) of a mat electrospun from a third polymer dispersion-water mixture.
Figure 13D:
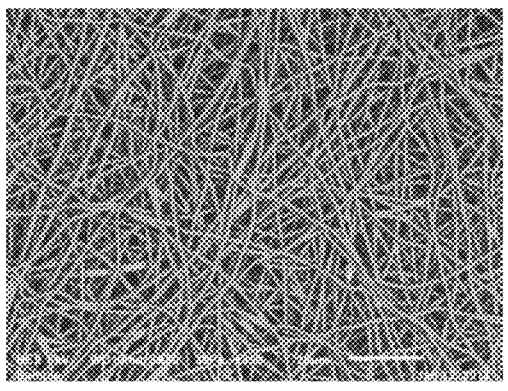
FIG. 13D is an SEM (950×) of a mat electrospun from a fourth polymer dispersion-water mixture.
Figure 13E:
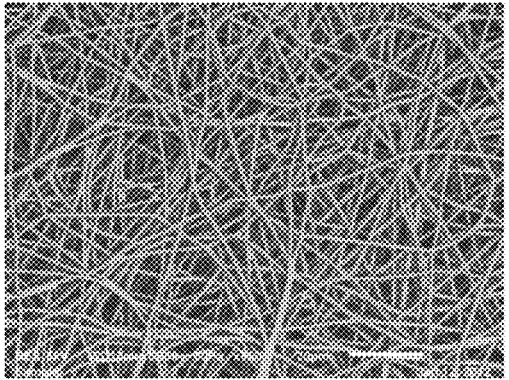
FIG. 13E is an SEM (950×) of a mat electrospun from a fifth polymer dispersion-water mixture.
Figure 13F:
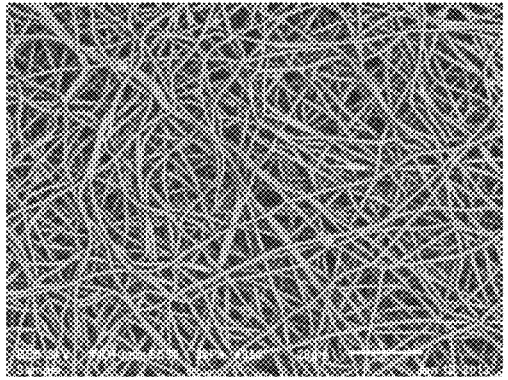
FIG. 13F is an SEM (950×) of a mat electrospun from a sixth polymer dispersion-water mixture.
Figure 13G:
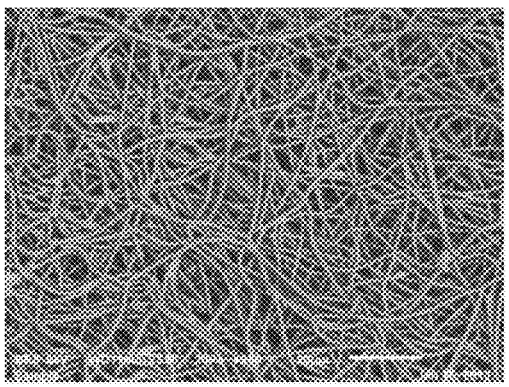
FIG. 13G is an SEM (950×) of a mat electrospun from a seventh polymer dispersion-water mixture.
Figure 13H:
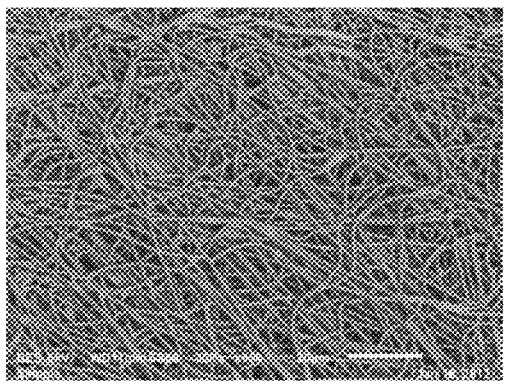
FIG. 13H is an SEM (950×) of a mat electrospun from an eighth polymer dispersion-water mixture.

It was observed that the additional water enabled bead-free electrospinning of a wider range of concentrations than was seen in Example 1. In the solution of FIG. 13C, it was observed that the PEO did not fully evolve during the sintering process.

This effect was not seen in connection with the solutions of Example 1; however, it was rare in connection with the solutions of Example 2.

Example 3

The apparatus described in Example 1 was again utilized to electrospin an FEP/PEO dispersion. The polymer solution was prepared by obtaining a 55 wt % FEP aqueous dispersion. Crystalline PEO with an average chain molecular weight of approximately 300,000 was used. The PEO was mixed with water in an approximately 30 wt % concentration and mixed until substantially homogenous. The 55 wt % FEP dispersion was added to the PEO/water mixture to create a 0.06 g/ml mixture of PEO to FEP dispersion. The FEP/PEO/water combination was then mixed until substantially homogeneous. The resulting mixture was strained through a 70 micrometer nylon cell strainer to remove any remaining clumps in the mixture.

The polymer solution was loaded into the syringe and the syringe pump was configured to dispense 0.01 ml of solution per minute. A sintered tube of electrospun 0.048 g/ml PTFE to PEO from Example 1 was placed over the collector. The syringe pump was activated and the high voltage power source turned on at 15,000 kV. The solution was forced through the syringe tip, where it was electrically charged and pulled in a small diameter fiber toward the collector. The electrospun FEP fibers were collected on top of the sintered PTFE tube. The process was run for approximately 15 minutes and the collector was removed and heated to 325 degrees C. for 10 minutes. The collection and the heating processes were repeated one time to increase the thickness of the covering. The resulting mat was removed from the collector. The cooked FEP mat was analyzed using a JEOL JSM-6510LV Scanning Electron Micrograph.

Figure 14A:
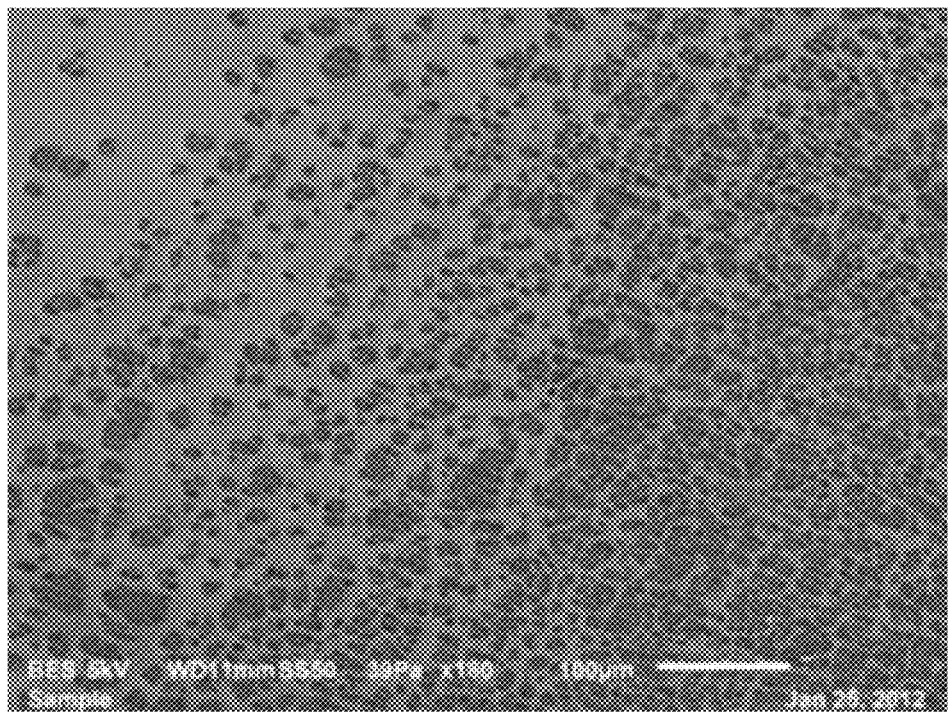
FIG. 14A is an SEM (180×) of a cooked, electrospun fluorinated ethylene propylene (FEP) coating over an electrospun PTFE layer.
Figure 14B:
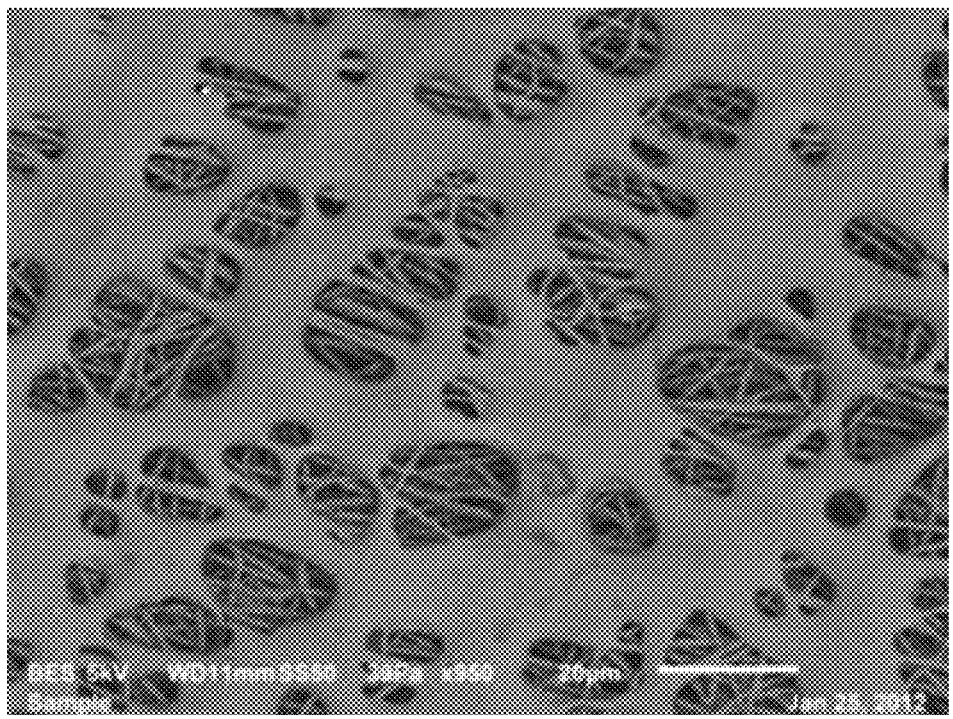
FIG. 14B is an SEM (950×) of the construct of FIG. 13A.

FIGS. 14A and 14B are SEMs of the cooked electrospun FEP over the electrospun PTFE. FIG. 14A is at 180× magnification and FIG. 14B is at 950× magnification.

It was observed in this example that upon heating, the electrospun FEP fibers would melt, creating a semi-porous coating over the electrospun PTFE fibers. In other examples, the porosity could be increased or decreased by increasing or decreasing, respectively, the amount of time the FEP is electrospun onto the PTFE fibers. Additionally, changing the heating temperature may also affect the porosity of the cooked FEP layer. For example, the higher the temperature, the more the FEP may tend to flow and fill in voids. In some embodiments, an impervious layer may be created by repeated electrospinning of an FEP layer. This type of coating could additionally be used to create a secondary porosity for hydrophobic or hydrophilic properties as well as a porous coating configured to screen for ingrowth cells based on cell size. Furthermore, the construct of this example exhibited an increase in tensile strength as well as elasticity over the electrospun PTFE alone.

Example 4

Dip Coating

Multilayered constructs may be formed in some embodiments by dip coating an electrospun or other material. In some embodiments, cracking of the dip coating may be reduced by reducing the thickness of the dip solution.

For example, a PTFE layer was dip coated on a construct by adding 20 ml of water to 50 ml of a 60 wt % PTFE dispersion to thin the dispersion. A fiber mat was then dipped in the solution to coat the mat. The dip coat was then sintered at 385 degrees C. for 15 minutes.

An FEP layer was dip coated on a construct by adding 20 ml of water to 50 ml of a 55 wt % dispersion to thin the dispersion. A fiber mat was then dipped in the solution to coat the mat. The dip coat was then cooked at 325 degrees C. for 15 minutes.

In other embodiments, more or less water, for example from about 10 ml to about 50 ml, may be added to similar amounts and concentrations of dispersion to thin the dispersion. Additionally, substances other than, or in addition to, water may be used to thin a dispersion for dip coating. For example, a surfactant or a solvent may be used. In some such cases the surfactant or solvent may later be removed from the construct, including embodiments where it is allowed to evaporate when the coat is sintered or cooked. Alcohols, glycols, ethers, and so forth may be so utilized.

Example 5

Endothelial Cell Attachment Assay

In some embodiments, the degree of endothelial cell attachment to a material may be determined according to the following assay. As used herein, values for "in vitro endothelial cell attachment" are determined by following the procedure disclosed below.

In this assay, the capacity of PTFE sample materials were tested to determine their ability to support the growth and/or attachment of porcine aortic endothelial cells. The PTFE materials comprised electrospun PTFE fiber mats spun from a 0.032 g/ml solution similar to that described in connection with FIG. 12C and Example 1. A standard curve with a range of endothelial cell seeding densities was generated to correlate cell attachment with PTFE materials.

First, the PTFE materials and Beem capsules were ethylene oxide (ETO) sterilized. The Beem capsules were assembled with PTFE materials in an aseptic field.

An endothelial cell standard curve was prepared in a 96 well plate with duplicate wells for 0, 2.5K, 5K, 10K, 20K, 40K, 60K, and 80K endothelial cells per well in 200 µl total volume of media. The endothelial cells were allowed to attach 90 minutes at 37° C. in 5% $CO_2$. At 90 minutes, 20 µl of 5 mg/ml MTT (3-(4,5-Dimethylthiazol-2-yl)-2,5-Diphenyltetrazolium Bromide) was added to each well and incubated at 37° C. in 5% $CO_2$ for 3 hours. The assembly was inverted and the 96 well was gently rapped on an absorbent bench coat to remove media and unattached cells.

Actively respiring cells convert the MTT to an intracellular purple formazan product. Thus, after the incubation period, intracellular formazan must be solubilized by isopropanol. 200 µl of 100% isopropanol was added to wells in the 96 well plate, which was incubated at room temperature for 30 minutes. The solution in each well was then mixed by pipeting. 100 µl of supernatant from the endothelial cell standard wells were transferred to clean wells in 96-well clear-bottomed plate. The optical density (OD) was read at 560 nm and 650 nm. The background absorbance at 650 nm was subtracted from the 560 nm absorbance and the results, minus control, were graphed.

As used herein, "optical density" (OD) measures the absorbance of light in the solution. In this example, the greater the number of cells which attach to the material, and are available to react with the MTT, the greater the amount of formazan generated within the cell, the darker the color of purple formazan extracted into the supernatant, and, therefore, the higher the OD (or absorbance of light). Assuming that all the cells in the experiment convert MTT to its formazan derivative at the same rate, the OD measurement is directly proportional to the number of attached cells.

The PTFE materials in Beem capsules were pre-wet with 200 µl of D-PBS (Dulbecco's phosphate buffered saline) and incubated at 37° C. in 5% CO2 for 50 minutes. The D-PBS was removed from the Beem capsules. The Beem capsules were then seeded with 50K endothelial cells in 200 µl of complete media, with the exception of a Beem control capsule for each test material, which contained complete media only (no cells). The media-only Beem capsule controls were processed identically as the Beem capsules seeded with endothelial cells. The endothelial cells were allowed to attach 90 minutes at 37° C. in 5% $CO_2$. At 90 minutes, 20 µl of 5 mg/ml MTT ((3-(4,5-Dimethylthiazol-2-yl)-2,5-diphenyltetrazolium bromide) was added to each Beem capsule, including controls, and incubated at 37° C. in 5% $CO_2$ for 3 hours. The Beem capsules were inverted and gently rapped on an absorbent bench coat to remove media and unattached cells.

The PTFE materials were carefully removed from Beem assemblies and placed in a microcentrifuge tube containing 200 µl of 100% isopropanol for 30 minutes. The microcentrifuge tubes were then vortexed with the PTFE materials and isopropanol for 3-5 minutes to release formazan into the supernatant. 100 µl of supernatant from the microcentrifuge tubes were transferred to clean wells in 96-well clear-bottomed plate (the same plate with the standards, described above). The OD was read at 560 nm and 650 nm. The background absorbance at 650 nm was subtracted from the 560 nm absorbance and the results, minus control were analyzed. The number of cells attached to each sample was interpolated from the standard curve results. As described in the standard curve wells outlined above, the MTT formazan was produced in proportion to the number of attached live cells within each capsule.

A standard curve of porcine endothelial cells was prepared for each unique assay of test materials and run in parallel with the materials in Beem capsules. In addition to electrospun samples, commercial expanded PTFE (ePTFE) material samples were also tested to provide a reference or comparison for the electrospun materials. The control ePTFE material used was the commercially available Bard Impra Straight Thinwall Vascular Graft (Cat #80S06TW), which is often used as a control material in relevant literature as it is known to have a favorable biologic response and favorable endothelial cell attachment.

To quantify the measurements obtained for the test materials, a standard curve was generated by measuring the optical density using the wells known to contain 0, 2.5K, 5K, 10K, 20K, 40K, 60K, and 80K endothelial cells per well. Using the generated standard curve, the number of attached cells in the experimental wells was then calculated.

The materials disclosed herein may be configured to achieve various amounts of in vitro endothelial cell attachment as defined by this assay. As described above, changes to the percent porosity of a mat, the thickness of the mat, and/or the diameter of fibers comprising the mat may influence the characteristics of the mat, including the response of the material to this assay. Thus, the number of cells attached to the electrospun materials were compared by normalizing the results to the number of cells attached the ePTFE control material. The endothelial cell attachment for the electrospun material assayed was greater that 170% of the endothelial cell attachment of the ePTFE control material. Materials within the scope of this disclosure may have in vitro endothelial cell attachments of 170%, more than 170%, or less than 170% of an ePTFE control material. For example, from 30% to more than 170% of the endothelial cell attachment of an ePTFE control material, including more than 30%, more than 40%, more than 50%, more than 75%, more than 100%, more than 125%, more than 150%, more than 160%, more than 165%, and more than 170% of the endothelial cell attachment of an ePTFE control material.

Example 6

Rodent Study

In this example, the biocompatibility response of an electrospun polymer fiber-coated material was compared against commercially-available ePTFE grafts and similar constructs. Eleven rodents were each subcutaneously implanted with a pledget of polymer material, the pledget obtained using a 2-4 mm biopsy punch. Two rodents were implanted with an electrospun fiber coated PTFE labeled MM1 E. This material was obtained by electrospinning a 0.032 g/ml solution, similar to that discussed in Example 5. The implanted material comprised a layered construct, with an FEP film disposed between two layers of electrospun PTFE coating. Two rodents were implanted with portions of a commercially available ePTFE stent graft material labeled ePTFE Sample 1, one rodent with the inside diameter (ID) material and one with the outside diameter (OD) material. Likewise, two rodents were implanted with inside and outside diameter materials from a commercially available ePTFE stent graft material labeled ePTFE Sample 2. Two rodents were implanted with inside and outside diameter materials from a commercially available heparin surface-coated ePTFE stent graft material labeled ePTFE Sample 3. Two rodents were implanted with inside and outside diameter materials from an ePTFE vascular graft material labeled ePTFE Sample 4. ePTFE samples 1 to 4 are a representative sampling of commercially available ePTFE stents and vascular grafts. Finally, one rodent was implanted with a portion of an ePTFE stent graft material labeled Control ePTFE. This sample is a commercially available ePTFE material produced by Bard which is often used as a control material in relevant literature.

After two weeks of implantation the implanted samples were analyzed for inflammation and cellular penetration. Specifically, pledgets of each of the above materials were cut or punched prior to surgery. Materials were ETO sterilized. On the day of surgery, subjects were prepped for sterile surgical procedures. Each subject was ear tagged for unique study identification and for the ability to evaluate subjects based on subject number to maintain an investigator-blinded analysis of the data, prior to de-coding the data.

At the end of the two-week implantation period, all subjects were euthanized and implanted materials and surrounding tissue were explanted. The explants were immediately placed into 2% paraformaldehyde fixative for up to 48 hours and then changed into a 70% ethanol solution for subsequent processing for paraffin embedding. Tissue blocks were processed for histology and immunohistochemistry then stained with hematoxylin and eosin or trichrome stain or reacted with antibodies for vWF (an endothelial cell marker) and CD-68 (a marker for activated macrophages). All slides that were subjectively evaluated were digitally scanned using the Aperio ScanScope CS system. Inflammatory response and cellular penetration into the material were quantified as described below.

A. Inflammatory Response

The inflammatory responses towards the various implanted PTFE materials were compared. The outer diameter (OD) and the inner diameter (ID) of the material were separately characterized. To quantify the inflammatory response, an established equation was used to provide weight to staining intensities and provide a quantitative value to the macrophage counts. The equation was based on equations currently used by pathologists in cancer research called the H-score (Nakopoulou et al., Human Pathology vol. 30, no. 4, April 1999). The H-score was obtained by the formula:

(3×percentage of strongly staining nuclei)+(2×percentage of moderately staining nuclei)+(percentage of weakly staining nuclei)=a range of 0 to 300

Strongly staining nuclei were represented by red in a false color mark-up in a digital algorithm, moderately stained nuclei were represented by orange in the false color mark-up, and weakly stained nuclei were represented by yellow. By inserting these counts into the formula above, a quantitative inflammatory response is obtained. A one-way ANOVA analysis with a Tukey post-hoc test (p<0.05) was used to assess statistical differences.

FIG. 15 illustrates the inflammatory response caused by the various materials as quantified by H-Score. Qualitatively, most materials were found to be moderately reactive with an average inflammatory score between 101 to 200, with scores over 250 considered inflammatory. The present electrospun PTFE material (MM1 E), both OD and ID and the ePTFE Sample 1 OD material had inflammatory H-scores measuring below 150. Materials found to be strongly reactive with inflammatory scores well above 150, such as 201 to 300 were the ePTFE Sample 1 ID and ePTFE Sample 3 ID materials. The difference between the lower H-Scores and the higher H-scores was statistically significant. The relatively low response of ePTFE Sample 1 OD was counteracted by the high response seen on the ID of the same sample.

Lower inflammation in response to the MM1 E material indicates that it is less hostile to surrounding biological tissue. MM1 E is the only material that showed significantly lower inflammatory response on both the OD and ID, both of which would be exposed to biological cells and tissue during use as a stent coating. More specifically, the OD is adjacent the endothelial layer of a blood vessel and the ID is in contact with blood cells. These results indicate that MM1 E is more biocompatible than other available materials.

B. Cellular Penetration

The ability of cells to penetrate the material from both the inner to outer surfaces and the outer to inner surfaces was measured and defined as cellular penetration. More specifically, cellular penetration as a percentage of PTFE material thickness was determined by performing measurements of the material thickness at 100 µm intervals and measuring the depth of cellular penetration from the superficial surface towards the midline. The percent of cellular penetration was measured from the superficial sides (from inner surface and from outer surface) of the material. A one-way ANOVA analysis with a Tukey post-hoc test (p<0.05) was used to assess statistical differences between groups.

This analysis demonstrated that all materials tested had some degree of cellular penetration meaning that cells were able to migrate into the architecture of the PTFE construct. As shown in FIG. 16, the MM1 E-ID and VT-ID materials were found to be statistically different from each other. However, relevant trends were observed from the remainder. This graph demonstrates that various PTFE materials/devices may have different cellular ingrowth. For example, both the MM1 E and Fluency PTFE materials (both OD and ID) demonstrated a tendency towards promoting a greater amount of cellular penetration.

Of particular relevance, the MM1 E material was unique in that it appeared to encourage the greatest cellular penetration when characterized from the edge of the material (superficial side) across to the middle layer. Both the MM1 E-OD and MM1 E-ID constructs had greater than 80% migration of cells to the relatively impermeable middle layer. FIG. 17 shows how cells migrate through the outer (OD) and inner (ID) layers, but most cannot penetrate the middle layer. Specifically, the dotted lines in FIG. 17 indicate the middle layer of the construct. The lack of dark spots (stained cells) in this zone reflects a lack of cellular migration or cellular penetration into this zone. The areas immediately adjacent the middle zone are the outer and inner layers, one of which is indicated by the double headed arrow. The dark spots in these zones reflect cellular penetration into these more porous portions of the construct.

EXEMPLARY EMBODIMENTS

The following embodiments are illustrative and exemplary and not meant as a limitation of the scope of the present disclosure in any way.

I. Medical Appliance

In one embodiment a medical appliance comprises a first layer of electrospun polytetrafluoroethylene (PTFE), having an average percent porosity between about 30% and about 80%.

The electrospun PTFE may comprise a mat of PTFE nanofibers.

The electrospun PTFE may comprise a mat of PTFE microfibers.

The medical appliance may further comprise a second layer of electrospun PTFE nanofibers, wherein the first layer of electrospun PTFE is disposed such that it defines a first surface of the medical appliance, and the second layer of electrospun PTFE is disposed such that it defines a second surface of the medical appliance.

In some embodiments, the first layer of electrospun PTFE has an average percent porosity between about 35% and about 70%.

In other embodiments, the first layer of electrospun PTFE has an average percent porosity of between about 40% and about 60%.

The first layer of electrospun PTFE may have an average pore size configured to permit tissue ingrowth on the first surface of the medical appliance.

The first layer of electrospun PTFE may permit tissue ingrowth.

The second layer of electrospun PTFE may have an average percent porosity of about 50% or less.

The second layer of electrospun PTFE may have an average pore size configured to resist tissue ingrowth into or through the second surface of the medical appliance.

The medical appliance may also further comprise a cuff adjacent to an end of the medical appliance, the cuff configured to permit tissue ingrowth into or tissue attachment to the cuff.

The medical appliance may further include a tie layer disposed between the first layer of electrospun PTFE and the second layer of electrospun PTFE.

The tie layer may be configured to inhibit tissue ingrowth into or through the tie layer.

The first and second layers of electrospun PTFE and the tie layer may be configured to inhibit an unfavorable inflammatory response.

The first and second layers of electrospun PTFE material may have inflammatory H-scores measuring below about 150.

The first and second layers of electrospun PTFE material may be configured to allow an average cellular penetration of over 20%.

The first and second layers of electrospun PTFE and the tie layer may be configured to inhibit hyperplastic tissue growth including neointimal or pseudointimal hyperplasia.

The tie layer may comprise PTFE.

The tie layer may comprise a thermoplastic polymer.

The tie layer may comprise fluorinated ethylene propylene (FEP).

The tie layer may comprise electrospun FEP.

The electrospun FEP layer may be cooked.

The electrospun FEP layer may be configured to resist cellular ingrowth.

The electrospun FEP layer may be substantially impervious to cellular ingrowth.

The electrospun FEP layer may be substantially non-porous.

The electrospun FEP layer may be substantially porous.

The FEP may partially bond to the nanofibers of the first and second layers of electrospun PTFE.

The FEP may flow into and coat the nanofibers of the first and second layers of electrospun PTFE.

The FEP may coat the nanofibers of the first and second layers while maintaining the porosity of the layers.

The electrospun PTFE may be formed from a mixture comprising PTFE, polyethylene oxide (PEO), and water.

The mixture may be formed by combining a PTFE dispersion with PEO dissolved in water.

The mixture may comprise between about 0.02 and about 0.070 grams of PEO per ml of 60 wt % PTFE aqueous dispersion.

The medical appliance may further comprise a main lumen extending to a bifurcation and two branch lumens extending from the bifurcation.

The medical appliance may further comprise a main lumen and one or more branch lumens extending from a wall of the main lumen.

The electrospun PTFE may comprise a mat of beaded PTFE fibers.

At least one of the first and second layers of electrospun PTFE may have been heated and stretched after sintering.

The medical appliance may further comprise a reinforcing layer.

The reinforcing layer may comprise electrospun PTFE.

The reinforcing layer may have greater tensile strength in a first direction of the layer than in a second direction perpendicular to the first direction.

The medical appliance may comprise a tubular construct.

The reinforcing layer may comprise a tube disposed such that the first direction is in the axial direction of the tubular construct.

The reinforcing layer may comprise a strip wrapped helically around a portion of the tubular construct.

The medical appliance may have increased resistance to creep in the radial direction as compared to the axial direction.

II. Stents

In one embodiment, a stent comprises a frame configured to resist radial compression when disposed in a lumen of a patient, and a covering disposed on at least a portion of the scaffolding structure, the covering comprising a first layer of electrospun polytetrafluoroethylene (PTFE), the first layer having a percent porosity between about 30% and about 80%.

The electrospun PTFE may comprise a mat of PTFE nanofibers and/or PTFE microfibers.

The stent may further comprise a second layer of electrospun PTFE nanofibers, wherein the stent is generally tubular in shape and the first layer of electrospun PTFE is disposed such that it defines an inside surface of the stent and the second layer of electrospun PTFE is disposed such that it defines an outside surface of the stent.

In such an embodiment, the first layer of electrospun PTFE may have an average percent porosity between about 35% and about 70%.

The first layer of electrospun PTFE may have an average percent porosity of between about 40% and about 60%.

The first layer of electrospun PTFE may have an average pore size configured to permit tissue ingrowth on the inside surface of the stent.

The first layer of electrospun PTFE may permit tissue ingrowth.

The second layer of electrospun PTFE may have an average percent porosity of about 50% or less.

The second layer of electrospun PTFE may have an average pore size configured to resist tissue ingrowth into or through the second layer of electrospun PTFE.

The stent may further comprise a cuff adjacent to an end of the stent, the cuff configured to permit tissue ingrowth into the cuff.

A tie layer may be disposed between the first layer of electrospun PTFE and the second layer of electrospun PTFE.

The tie layer may be configured to inhibit tissue ingrowth into the tie layer.

The tie layer may comprise PTFE.

The tie layer may be a thermoplastic polymer.

The tie layer may be fluorinated ethylene propylene (FEP).

The tie layer may be electrospun FEP.

The electrospun FEP layer may be cooked.

The electrospun FEP layer may be configured to resist cellular ingrowth.

The electrospun FEP layer may be substantially impervious to cellular ingrowth.

The electrospun FEP layer may be substantially nonporous.

The electrospun FEP layer may be porous.

The FEP may partially bond to the nanofibers of the first and second layers of electrospun PTFE.

The second layer of electrospun PTFE material may be configured to permit tissue ingrowth into the second layer to reduce device migration.

The first and second layers of electrospun PTFE and the tie layer may be configured to inhibit hyperplastic tissue growth such as neointimal or psuedointimal hyperplasia.

The first and second layers of electrospun PTFE and the tie layer may be configured to inhibit an unfavorable inflammatory response.

The first and second layers of electrospun PTFE material have inflammatory H-scores measuring below about 150.

The first and second layers of electrospun PTFE material may be configured to allow an average cellular penetration of over 20%.

The FEP may flow into and coat the nanofibers of the first and second layers of electrospun PTFE.

The FEP may coat the nanofibers of the first and second layers while maintaining the porosity of the layers.

The electrospun PTFE may be formed from a mixture comprising PTFE, polyethylene oxide (PEO), and water.

The mixture may be formed by combining a PTFE dispersion with PEO dissolved in water.

The electrospun PTFE may be electrospun onto a rotating mandrel.

The mixture may comprise between about 0.02 and about 0.070 grams of PEO per ml of 60 wt % PTFE aqueous dispersion.

The frame of the stent may be comprised of a single wire.

The wire may be helically wound around a central axis of the stent.

The wire may have a wave-like pattern defining apexes and arms.

Alternating apexes adjacent an end of the stent may have different relative heights.

Each apex may have a radius of between about 0.12 mm and 0.64 mm.

The stent may have a first portion disposed near the midbody of the stent and second and third portions disposed near the ends of the stent, and wherein the arms disposed within the second and third portions are relatively longer than the arms disposed within the first portion.

Moreover, a distance, apex to apex length, may be defined as the distance between a first apex and a second apex wherein the first apex lies on a first coil of wire and the second apex lies on a second coil of wire adjacent to the first coil, and wherein the first apex and the second apex lies substantially on a line on the outer surface of the stent, the line being co-planar with and parallel to a central axis of the stent, wherein the apex to apex distance is smaller at the midbody of the stent, relative to the apex to apex distance near the ends of the stent.

The stent may be structured such that a midbody portion of the stent is relatively less compressible than a first and a second end of the stent.

The stent may further comprise a main lumen extending to a bifurcation and two branch lumens extending from the bifurcation.

The stent may further comprise a main lumen and one or more branch lumens extending from a wall of the main lumen.

The electrospun PTFE may comprise a mat of beaded PTFE fibers.

III. Tubular Vascular Prosthesis

In one embodiment, a tubular vascular prosthesis comprises a porous inner layer, a porous outer layer, and a substantially non-porous tie layer disposed between the inner layer and the outer layer.

At least one of the inner layer and the outer layer may comprise an electrospun material.

The tie layer may be substantially impervious to cellular ingrowth.

The inner and outer layers may be configured to permit cellular ingrowth.

IV. Method of Constructing a Medical Appliance

In one embodiment, a method of constructing a medical appliance comprises electrospinning a first tube of polytetrafluoroethylene (PTFE) onto a mandrel, the first tube having a percent porosity between about 30% and about 80%, and sintering the first tube.

The first tube of PTFE may be electrospun onto a rotating mandrel.

The method may further comprise applying a second tube of electrospun PTFE around the first layer.

The method may further comprise applying a scaffolding structure around the first tube, and applying a fluorinated ethylene propylene (FEP) layer around the first tube and the scaffolding structure, prior to applying the second tube of electrospun PTFE.

The FEP layer may be configured to inhibit tissue ingrowth into or through the FEP layer.

The method may further comprise heating the medical appliance such that the FEP layer bonds to the first and second tubes.

The FEP may partially bond to the fibers of the first and second tubes.

The FEP may flow into and coat the fibers of the first and second tubes.

The FEP may coat the fibers of the first and second tubes while maintaining the porosity of the tubes.

The second tube of electrospun PTFE may be formed by a method comprising electrospinning the second tube of PTFE onto a rotating mandrel and sintering the second tube.

A compressive wrap may be applied around the second tube before the medical appliance is heat treated.

Electrospinning the first tube of PTFE may comprise mixing a PTFE dispersion with polyethylene oxide (PEO), wherein the PEO is dissolved in water to form a mixture; and discharging the mixture from an orifice onto the rotating mandrel.

The mixture may comprise between about 0.02 and about 0.07 grams of PEO per ml of 60 wt % PTFE aqueous dispersion.

The mixture comprises between about 0.03 and about 0.04 grams of PEO per ml of 60 wt % PTFE aqueous dispersion.

The method may further comprise coupling a cuff to an end of the medical appliance, the cuff configured to permit tissue ingrowth into the cuff.

V. Method for Promoting Endothelial Cell Growth

In one embodiment, a method for promoting endothelial cell growth on an implantable medical appliance comprises implanting the medical appliance into a patient, the medical appliance coated with at least one electrospun polymer layer having a percent porosity of between about 35% and about 70%, such that endothelial cells grow on or attach to the surface of the at least one electrospun polymer layer.

The implantable medical appliance may comprise a stent.

The implantable medical appliance may comprise a graft.

The at least one electrospun polymer layer may comprise an electrospun PTFE layer.

The medical appliance may be coated with a second polymer layer that inhibits tissue or fluid migration through the second polymer layer.

The second polymer layer may comprise an FEP layer.

The electrospun fibrous PTFE may comprise randomized microfibers or nanofibers.

The at least one polymer layer of the implanted medical appliance may be configured to permit at least 30% in vitro endothelial cell attachment, compared to an expanded PTFE control material.

The at least one polymer layer of the implanted medical appliance may be configured to permit at least 40% in vitro endothelial cell attachment, compared to an expanded PTFE control material.

The at least one polymer layer of the implanted medical appliance may be configured to permit at least 50% in vitro endothelial cell attachment, compared to an expanded PTFE control material.

The at least one polymer layer of the implanted medical appliance may be configured to permit at least 75% in vitro endothelial cell attachment, compared to an expanded PTFE control material.

The at least one polymer layer of the implanted medical appliance may be configured to permit at least 100% in vitro endothelial cell attachment, compared to an expanded PTFE control material.

The at least one polymer layer of the implanted medical appliance may be configured to permit at least 125% in vitro endothelial cell attachment, compared to an expanded PTFE control material.

The at least one polymer layer of the implanted medical appliance may be configured to permit at least 150% in vitro endothelial cell attachment, compared to an expanded PTFE control material.

The at least one polymer layer of the implanted medical appliance may be configured to permit at least 160% in vitro endothelial cell attachment, compared to an expanded PTFE control material.

The at least one polymer layer of the implanted medical appliance may be configured to permit at least 165% in vitro endothelial cell attachment, compared to an expanded PTFE control material.

The at least one polymer layer of the implanted medical appliance may be configured to permit at least 170% in vitro endothelial cell attachment, compared to an expanded PTFE control material.

The percent porosity of the electrospun polymer layer may be between about 40% and about 60%.

The mandrel may comprise a main portion and two leg portions, the main portion configured to coincide with a main lumen of a bifurcated medical appliance and the two leg portions configured to coincide with the leg portions of the bifurcated medical appliance.

The two leg portions of the mandrel may be removable from the main portion of the mandrel.

The first tube may be electrospun by rotating the mandrel about an axis of the leg portions of the mandrel while electrospinning fibers and rotating the mandrel about an axis of the main portion of the mandrel while electrospinning fibers.

VI. Method for Promoting Cellular Growth into an Implantable Medical Appliance

In one embodiment, a method for promoting cellular growth into an implantable medical appliance comprises: obtaining a medical appliance coated with at least one electrospun polymer layer having a percent porosity of between about 30% and about 80% and at least one layer that is substantially impervious to cellular growth; and implanting the medical appliance into a patient such that the electrospun polymer layer of the medical appliance is in direct contact with body fluid or body tissue.

The at least one electrospun polymer layer may comprise electrospun PTFE.

The electrospun PTFE material may be configured to permit at least 20% cellular penetration, in vivo two weeks after murine implantation.

V. Method for Inhibiting a Neointimal Hyperplasia Response

In one embodiment, a method for inhibiting a neointimal hyperplasia response to an implantable medical appliance comprises implanting the medical appliance into a patient, the medical appliance coated with a first electospun PTFE layer comprising a porous mat and a second polymer layer that inhibits tissue ingrowth into or through the second polymer layer.

The first electrospun polymer layer may permit endothelial cell growth or attachment on the surface of the first electrospun polymer layer.

The first electrospun polymer layer may comprise a fibrous PTFE layer and the second polymer layer may comprise an FEP layer.

The medical appliance may also be coated with a third polymer layer comprising an electrospun PTFE layer, such that the FEP layer is disposed between the first and third polymer layers.

The first and third polymer layers may comprise an electrospun microfiber or nanofiber PTFE mat.

The second polymer layer may comprise an electrospun FEP mat.

VIII. Method for Inhibiting an Inflammatory Response

In one embodiment, a method for inhibiting an inflammatory response to an implantable medical appliance comprises implanting the medical appliance into a patient, the medical appliance coated with a first electrospun polymer layer comprising a porous PTFE mat and a second polymer layer comprising FEP that inhibits tissue ingrowth into or through the second polymer layer.

The first electrospun polymer layer, when placed in vivo, may have an H-score of less than 150 two weeks after murine implantation.

While specific embodiments of stents and other medical appliances have been illustrated and described, it is to be understood that the disclosure provided is not limited to the precise configuration and components disclosed. Various modifications, changes, and variations apparent to those of skill in the art having the benefit of this disclosure may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A method for inhibiting a neointimal hyperplasia response to an implantable medical appliance, comprising implanting the medical appliance into a patient, the medical appliance coated with a first electrospun polytetrafluoroethylene (PTFE) layer comprising a porous mat and a second non electrospun polymer layer of fluorinated ethylene propylene (FEP) that is impervious to tissue ingrowth into the second polymer layer, wherein:
   the implantable medical appliance comprises a tubular medical device;
   the second polymer layer is disposed around the first electrospun PTFE layer;
   the first electrospun PTFE layer defines an inside surface of the tubular medical device;
   wherein the first electrospun PTFE layer is sintered,
   wherein the second polymer layer is nonporous and non-fibrous,
   wherein the medical appliance is coated with a third polymer layer comprising electrospun PTFE, such that the FEP is disposed between the first and third layers, and
   wherein the combined thickness of the layers is between about 20 micrometers and 100 micrometers.

2. The method of claim 1, wherein the first electrospun PTFE layer permits endothelial cell growth or attachment on the surface of the first electrospun PTFE layer.

3. The method of claim 1, wherein the second polymer layer is a dip coating of FEP.

4. The method of claim 1, wherein the second polymer layer is a spray coating of FEP.

5. The method of claim 1, further comprising an ePTFE layer disposed around the second polymer layer.

6. The method of claim 1, furthing comprising an ePTFE layer.

7. The method of claim 1, wherein the second polymer layer partially coats of the first electrospun PTFE layer.

8. The method of claim 1, wherein the first electrospun PTFE layer is produced by depositing PTFE fibers on a vertically oriented, rotating mandrel.

9. A method for inhibiting a neointimal hyperplasia response to an implantable medical appliance, comprising implanting the medical appliance into the vasculature of a patient, the medical appliance comprising a first electrospun PTFE layer, wherein the first electrospun PTFE layer is sintered, and a second non-electrospun polymer layer of fluorinated ethylene propylene (FEP) that is impervious to tissue ingrowth into the second polymer layer, wherein the implantable medical appliance is implanted such that the first electrospun PTFE layer is in contact with blood flowing through the patient's vasculature, wherein the second polymer layer is nonporous and non-fibrous, wherein the medical appliance is coated with a third polymer layer comprising electrospun PTFE, such that the FEP is disposed between the first and third layers, and wherein the combined thickness of the layers is between about 20 micrometers and 100 micrometers.

10. The method of claim 9, wherein the first electrospun PTFE layer permits endothelial cell growth.

11. The method of claim 9, wherein the second polymer layer is a dip coating of FEP.

12. The method of claim 9, wherein the second polymer layer is a spray coating of FEP.

13. The method of claim 9, wherein the second polymer layer is disposed around the first electrospun PTFE layer.

14. The method of claim 13, wherein the first electrospun PTFE layer defines an inside surface of a tubular medical device.

15. The method of claim 14, further comprising an ePTFE layer disposed around the first electrospun deposited PTFE layer.

16. The method of claim 9, further comprising an ePTFE layer.

17. The method of claim 9, wherein the second polymer layer partially coats of the first electrospun PTFE layer.

18. A method for inhibiting a neointimal hyperplasia response to an implantable medical appliance, comprising:
    implanting the medical appliance into a patient, the medical appliance coated with a first electrospun polytetrafluoroethylene (PTFE) layer comprising a porous mat and a second non- electrospun polymer layer of fluorinated ethylene propylene (FEP) that is impervious to tissue ingrowth into the second polymer layer;
    wherein the second polymer layer is disposed around the first electrospun PTFE
    wherein the first electrospun PTFE layer defines an inside surface of the tubular medical device;
    wherein the first electrospun PTFE layer is stretched,
    wherein the second polymer layer is nonporous and non-fibrous,
    wherein the medical appliance is coated with a third polymer layer comprising electrospun PTFE, such that the FEP is disposed between the first and third layers, and
    wherein the combined thickness of the layers is between about 20 micrometers and 100 micrometers.

* * * * *